(12) United States Patent
Ezrin et al.

(10) Patent No.: US 6,706,892 B1
(45) Date of Patent: Mar. 16, 2004

(54) PULMONARY DELIVERY FOR BIOCONJUGATION

(75) Inventors: Alan M. Ezrin, Moraga, CA (US); Angelica Fleser, Montreal (CA); Martin Robitaille, Terrasse-Vaudreuil (CA); Peter G. Milner, Los Altos Hills, CA (US); Dominique P. Bridon, Outremont (CA)

(73) Assignee: Conjuchem, Inc., Montreal (CA)

( * ) Notice: Subject to any disclaimer, the term of this patent is extended or adjusted under 35 U.S.C. 154(b) by 0 days.

(21) Appl. No.: 09/656,121

(22) Filed: Sep. 6, 2000

Related U.S. Application Data
(60) Provisional application No. 60/152,681, filed on Sep. 7, 1999.

(51) Int. Cl.[7] ............... A61K 31/4015; A61K 47/42; A61P 7/06; A61P 9/06; A61P 11/08
(52) U.S. Cl. .............. 548/548; 544/269; 544/372; 546/93; 546/208; 548/520; 514/254.02; 514/290; 514/422; 514/423; 514/265; 514/326; 514/776; 424/45; 424/489; 424/78.17; 424/78.37
(58) Field of Search ............... 544/274, 372, 544/269; 546/93, 208; 548/520, 548; 514/254.02, 290, 422, 423, 265, 326, 776; 424/45–46, 489, 78.17, 78.37

(56) References Cited

U.S. PATENT DOCUMENTS

| | | |
|---|---|---|
| 4,361,553 A | 11/1982 | Loh et al. |
| 4,462,941 A | 7/1984 | Lee et al. |
| 4,507,234 A | 3/1985 | Kato et al. |
| 4,981,979 A | 1/1991 | Sivam |
| 5,017,689 A | 5/1991 | Hruby et al. |
| 5,087,616 A | 2/1992 | Myers et al. |
| 5,135,736 A | 8/1992 | Anderson et al. |
| 5,140,013 A | 8/1992 | Gaudreault et al. |
| 5,169,933 A | 12/1992 | Anderson et al. |
| 5,306,809 A | 4/1994 | Boon et al. |
| 5,376,662 A | 12/1994 | Ockert et al. |
| 5,482,930 A | 1/1996 | Wei et al. |
| 5,493,007 A | 2/1996 | Burnier et al. |
| 5,547,667 A | 8/1996 | Angelucci et al. |
| 5,580,853 A | 12/1996 | Sytkowski |
| 5,612,034 A | 3/1997 | Pouletty et al. |
| 5,614,487 A | 3/1997 | Battersby et al. |
| 5,654,276 A | 8/1997 | Barret et al. |
| 5,807,827 A | 9/1998 | Lee et al. |
| 5,945,033 A | 8/1999 | Yen |
| 6,013,263 A | 1/2000 | Barney et al. |
| 6,017,536 A | 1/2000 | Barney et al. |
| 6,103,236 A | 8/2000 | Suzawa et al. |

FOREIGN PATENT DOCUMENTS

| | | | |
|---|---|---|---|
| CA | 2265861 | 3/1998 | |
| DE | 41 22 210 | 1/1993 | ......... A61K/37/02 |
| EP | 0554708 A1 | 8/1993 | |
| EP | 0602290 | 4/1994 | |
| WO | 9108220 | 6/1991 | |
| WO | 9325217 | 12/1993 | |
| WO | 9501806 | 1/1995 | |
| WO | 9510302 | 4/1995 | |
| WO | 9606626 | 3/1996 | |
| WO | 97/23243 | 7/1997 | ......... A61K/47/48 |
| WO | 9800171 | 1/1998 | |
| WO | 9924074 | 5/1999 | |
| WO | 9924075 | 5/1999 | |
| WO | 9924462 | 5/1999 | |
| WO | 9948536 | 9/1999 | |
| WO | 0076550 A2 | 12/2000 | |
| WO | 00/76550 | 12/2000 | ......... A61K/47/48 |
| WO | 0076551 A2 | 12/2000 | |
| WO | 00/76551 | 12/2000 | ......... A61K/47/48 |

OTHER PUBLICATIONS

U.S. patent application Ser. No. 09/445,986, filed Dec. 16, 1999.
U.S. patent application Ser. No. 09/623,533, filed Sep. 5, 2000.
U.S. patent application Ser. No. 09/623,548, filed Sep. 5, 2000.
U.S. patent application Ser. No. 09/657,276, filed Sep. 7, 2000.
U.S. patent application Ser. No. 09/657,295, filed Sep. 7, 2000.
Cancer Research, 1986, 46, 467–473.
Bioog. & Med. Chem. Lett., 1997, 7, (5), 617–622.
J. Med. Chem., 1998, 41, 2701–2708.
Chem. Pharm. Bull., 1997, 45, (2), 399–401.
J. Pharm. Sci., 1998, 87 (3), 338–346.
Anticancer Drugs, 1999, 10, 785–790.
Clinical Cancer Research, 1999, 5, 753–759.
European J. Cancer, 1995, 31A (2), 283–284.
J. Pharm. & Experimental Therapeutics, 1981, 219 (2), 389–393.
Ann. NY Acad. Sciences, 1971, 186, 284–286.
International J. Pharmaceutics, 1991, 67, 177–184.
International J. Pharmaceutics, 1993, 89, 91–102.
Proc. Natl. Acad. Sci., 1996, 93 (5), 2186–2191.
Anti–Cancer Drugs, 1997, 8, 677–685.
Anti–Cancer Research, 1994, 14, 1943–1950.
Neoplasma, 1988, 35, (3), 329–342.
Neoplasma, 1988, 35, (3), 343–349.
Anti–Cancer Drugs, 1997, 8, 835–844.
J. Surgical Research, 1991, 50, 156–162.

(List continued on next page.)

Primary Examiner—Edward J. Webman
(74) Attorney, Agent, or Firm—Morrison & Foerster LLP

(57) ABSTRACT

Methods of and compositions for pulmonary delivery of therapeutic agents which are capable of forming covalent bonds with a site of interest or which have formed a covalent bond with a pulmonary solution protein are disclosed. Therapeutic agents useful in the invention include wound healing agents, antibiotics, anti-inflammatories, antioxidants, anti-proliferatives, immunosupressants, anti-infective and anti-cancer agents.

34 Claims, No Drawings

OTHER PUBLICATIONS

*Anti–Cancer Drugs,* 1999, 10, 405–411.
*European J. Nucl. Med.,* 1995, 22 (9), 989–996.
*Biol. Pharm. Bull.,* 1998, 21, (1), 56–61.
*Br. J. Cancer,* 1993, 67, 274–278.
*Nucl. Med. Biol.,* 1992, 19 (6), 685–695.
*Drug Delivery,* 1999, 6, 89–95.
*Cancer Research,* 1993, 53, 4238–4242.
*Science,* 1993, 261, 212–215.
Biotech Report, 1994/1995, 106–107.
Proceedings of the 8th American Peptide Symposium, 1983, 409–412.
Int. J. Biochem. Cell. Biol. 1998, 30, 1281–1284.
Endocrinology, 1982, 110 (3), 1049–1051.
J. Biol. Chem. 1995, 270 (43), 25344–25347.
J. Dev. Physiol., 1989, 12, 55–62.
Biopolymers (Peptide Science), 1998, 47, 451–463.
Ann. Rev. Neurosci, 1984, 7, 223–255.
Chem. Pharm. Bull. 1979, 27, (8), 1942–1944.
Proc. Natl. Acad. Sci. 1986, 83, 265–269.
TINS, 1993, 16, 403–409.
Methodological Surveys in Biochemistry and Analysis, 15, 1985.
Metodol. Surv. Biochem Anal., vol. 15, 1985, pp. 109–114.
Indian Journal of Biochemistry & Biophysics, 30, 4/93.
Indian J. Biochem. Biophys., vol. 30, No. 2, 1993, pp. 117–122.
J. of Histochemistry and Cytochemistry, 32, (9), 1984.
J. Histochem. Cytochem, vol. 32, No. 9, 1984, pp. 945–957.
Cell Tissue Res. 215 (3), 1981.
Cell Tissue Res., vol. 215, No. 3, 1981, pp. 577–589.
Int. Congr. Ser. Excerpta Medica, vol. 471, 1978, pp. 177–186.
Febs Letters, vol. 70, No. 1, 1976.
Analytical Biochemistry, vol. 215, No. 1, 1993, pp. 1–8.
Filho, Pharm Sci. 2, 1996, pp. 199–201.
Correa, Pharm Sci. 3, 1997, pp. 67–71.
Peptide Research 8 (3) 1995, pp. 124–137.
The J. of Pharm & Experimental Therapeutics, 280, 1997, pp. 1210–1214.
Blood Cells, Molecules and Diseases 23 (3), 1997, pp. 58–68.
Abstract JP 59138958, 1984, Mitsubishi Chemical Industries Co. JP.
Database Biosis, Accession No. XP–002172298.
Patent Abstracts of Japan No. 62138430.
Biol. Pharm. Bull., 1998, 21(1), 56–61.
Biochimica et Biophysica Acta, 1991, 1118, 83–90.
J. Med. Chem., 2000, 43, 1253–1256.
J. Med. Chem., 1998, 41, 853–863.
Allergie et Immunologie, 1996, 28, 186–191.
European J. Pharmaceutical Sciences, 1996, 4, 307–319.

PULMONARY DELIVERY FOR BIOCONJUGATION

This application claims the benefit of Provisional Application Ser. No. 60/152,681 filed Sep. 7, 1999.

FIELD OF THE INVENTION

This invention relates to the therapeutic and diagnostic agents in medicine. In particular, this invention relates to the field of delivery, in particular, pulmonary delivery, of therapeutic and diagnostic agents wherein the agents are capable of covalently bonding to a site of interest in vivo, to provide increased bioavailability and pharmacodynamic duration of therapeutic and diagnostic benefit for the given agent.

BACKGROUND OF THE INVENTION

Peptide and protein drugs are being used increasingly in major research and development programs in the pharmaceutical industry and are also an important class of therapeutic agents due to advances in genetic engineering and biotechnology. Systemic delivery of these macromolecular drugs and other therapeutic and diagnostic agents, however, has been limited to the parenteral route largely because of their extensive presystemic elimination when taken orally. Faced with this dilemma concerning the systemic delivery of these macromolecules with their unique conformational complexity for therapeutic activity, pharmaceutical scientists are continually evaluating the potential of various non-oral routes of administration as alternatives.

Despite the tremendous efforts that have been devoted to this problem, only limited success has been achieved—mostly with small peptides. An alternative, non-invasive means for systemic delivery of therapeutic and diagnostic agents is via the pulmonary system. Delivery via the pulmonary system is advantageous because the lungs provide a large but extremely thin absorptive mucosal membrane for increased absorption and delivery to the blood stream. However, pulmonary delivery of therapeutic and diagnostic agents is complicated by the complexity of the anatomic structure of the human respiratory system; the effect of respiration on drug deposition and an instability of the drugs resulting from degradation in either the lungs or plasma.

There is thus a need to improve and enhance delivery of therapeutic and diagnostic agents, especially pulmonary delivery of therapeutic and diagnostic agents through increasing the stability and blood absorption of the agents.

SUMMARY OF THE INVENTION

In order to meet these needs, the present invention is directed to therapeutic and diagnostic agents capable of forming covalent bonds to blood and pulmonary fluid proteins or other components ex vivo or in vivo. The therapeutic agents of this invention have a long duration of action for the management of disease. The invention relates to ex vivo and in vivo bioconjugation of therapeutic agents to protein (e.g. albumin), as well as an intrapulmonary in vivo bioconjugation of therapeutic agents to endogenous pulmonary fluid proteins or other components to dramatically increase the half life of the therapeutic agents and avoid the need for parenteral administration.

The present invention reflects the ability to bioconjugate selected therapeutic agents to blood and pulmonary pulmonary fluid proteins, including albumin, for processing as a particulate for intrapulmonary drug delivery. The pulmonary fluid protein conjugate is targeted to provide a stable drug substance that retains biological activity for prolonged periods of time. This invention provides prolonged local retention of therapeutic agent activity in the airways for use with selected therapeutic agents in managing pulmonary disease.

The invention is further directed to methods of facilitating systemic drug delivery of protein-therapeutic agent bioconjugates and to agents capable of forming bioconjugates to protein in vivo via pulmonary delivery with subsequent transcytosis across the alveolar and pulmonary mucosa. The invention is further directed to methods of facilitating systemic drug delivery of protein-therapeutic agent bioconjugates via pulmonary delivery of agents capable of forming bioconjugates in vivo, the agents crossing the epithelium of the alveolar or pulmonary mucosa, either through diffusion or receptor mediated transport, to conjugate with blood proteins. The methods of this invention result in long acting, systemic therapeutics that are stabilized by ex vivo or in vivo conjugation to pulmonary fluid proteins and/or blood proteins.

This invention is further directed to site-specific and protein-specific bioconjugation of a therapeutic agent to albumin. Albumin possesses a unique nucleophilic moiety, specifically, the thiol functionality on cysteine 34 that is capable of undergoing a nucleophilic attack on an electrophile present on a therapeutic agent modified according to the invention. This selective covalent bonding enables bioconjugation to extracellular as well as intracellular albumin for prolonged retention and bioavailabilty of the therapeutic agent.

This invention is further directed to the use of reactive chemistries including: N-hydroxy sulfosuccinimide, maleimide-benzoyl-succinimide, gamma-maleimidobutyryloxy succinimide ester, maleimidopropionic acid, isocyanate, thiolester, thionocarboxylic acid ester, imino ester, and carbodiimide anhydride. Maleimidopropionic acid is the preferred reactive chemistry, but the invention also contemplates the selection of the above and like reactive chemistries as an electrophilic moeity for bioconjugations with albumin or other proteins.

This invention is further directed to the use of a composition for the manufacture of a medicament where the composition comprises a derivative of an antihistamine and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an an histamine effect.

The modified antihistamine may be cetirizine, loratidine and analogs thereof.

This invention is further directed to the use of a composition for for the manufacture of a medicament where the composition comprises a derivative of an anti-angina agent and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an anti-angina effect.

The modfed anti-angina agent may be tirofiban or analogs thereof.

This invention is further directed to the use of a composition for the manufacture of a medicament where the composition comprises a derivative of an anti-hypertensive agent and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an anti-hypertensive effect.

The anti-hypetensive agent may be enalapril or analogs thereof.

This invention is further directed to the use of a composition for the manufacture of a medicament where the composition comprising a derivative of an anti-arrhythmic agent and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an anti-arrhythmic effect.

The anti-arrhythmic agent may be capobenic acid or analogs thereof. This invention is further directed to the use of a composition for the manufacture of a medicament where the composition comprising a derivative of an anti-depressant agent and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxy-sulfosuccinimide and a maleimide group for use in the treatment of the human body to provide an anti-depressant effect.

The anti-depressant agent may be fluoxetine or analogs thereof.

This invention is further directed to the use of a composition for the manufacture of a medicament said composition comprising a derivative of a bronchodilator and analogs thereof wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide a bronchodilation effect.

The bronchodilator may be theobromine acetamineor analogs thereof. This invention is further directed to the use of a composition for the manufacture of a medicament said composition comprising a derivative of an opioid and analogs thereof, wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an analgesic effect.

The opioid may be fentanyl or analogs thereof. This invention is further directed to the use of a composition for the manufacture of a medicament said composition comprising a derivative of an anti-inflammatory agent and analogs thereof, wherein the derivative includes a reactive functional group which reacts with amino groups, hydroxyl groups, or thiol groups on blood components to form stable covalent bonds, said reactive functional group being selected from N-hydroxysuccinimide, N-hydroxysulfosuccinimide and a maleimide group for use in the treatment of the human body to provide an anti-inflammatory effect.

The anti-inflammatory agent may be loxoprofen or analogs thereof.

This invention is further directed to the use of a composition for the manufacture of a medicament where the composition comprising a derivative of n an anti-thyroid deficiency agent and analogs thereof, wherein the derivative includes a reactive functional group which reacts with amino groups, hydroxyl groups, or thiol groups on blood components to form stable covalent bonds, said reactive functional group being selected from N-hydroxysuccinimide, N-hydroxy-sulfosuccinimide and a maleimide group for use in the treatment of the human body to provide an anti-thyroid deficiency effect.

the anti-thyroid deficiency agent may be thyroxine or analogs thereof.

This invention is further directed to composition comprising one or more compounds selected from the group consisting of 2-[2-[4-[(4-chlorophenyl)phenylmethyl[-1-piperazinyl] ethoxy]-maleimido-ethylacetamide;11-(N-maleimidopropionyl-4-piperidylidene)-8-chloro-6,11-dihydro-5H-benzo-[5,6]-cyclohepta-[1,2-b]-pyridine;

N-(2-maleimidoethyl)-(1(S)-Ethoxycarbonyl-3-phenylpropyl)-L-alanyl-L-prolinylamide;

N-[2-maleimidoethyl-ϵ-(3,4,5-trimethoxybenzamido)-caproic amide; Maleimidoethyl-1-theobromineacetamide;

N-(2-maleimidoethyl)-2-[4-(2-oxocyclopentan-1-ylmethyl) phenyl]-propionamide;

N-maleimidopropionyl-N-methyl-3-(p-trifluoromethylphenoxy)-3-phenylpropylamine; 4-[N-phenyl-3-maleimidopropionamido]-1-(2-phenylethyl) piperidine; and N-(2-maleimidoethyl-3,5-3',5' tetraiodothyroninamide This invention is further directed to the an aerosol composition for delivery of a therapeutic agent to the pulmonary system of a host comprising an aerosolized aqueous solution containing a modified therapeutic agent conjugated to a blood protein.

This invention is further directed to the use of a particulate formulation for delivery of a therapeutic agent to the pulmonary system of a host comprising:

a dispersable dry powder containing a modified therapeutic agent, the modified therapeutic agent comprising a therapeutic agent and a reactive group which reacts with amino groups, hydroxyl groups or thiol groups on pulmonary components to form a stable covalent bond wherein said therapeutic agent is covalently bonded to a blood protein.

DETAILED DESCRIPTION OF THE INVENTION

Definitions

To ensure a complete understanding of the invention the following definitions are provided:

Therapeutic Agents

Therapeutic agents are agents that have a therapeutic effect and include peptides and non-peptide organic molecules. Therapeutic agents include but are not limited to wound healing agents, antibiotics, anti-infectives, antioxidants, chemotherapeutic agents, anti-cancer agents, antiinflammatory agents, and antiproliferative drugs. Therapeutic agents also include abortifacients, ace-inhibitor, α-adrenergic agonists, β-adrenergic agonists, α-adrenergic blockers, β-adrenergic blockers, adrenocortical steroids, adrenbcortical supressants, adrenocorticotrophic hormones, alcohol deterrents, aldose reductase inhibitors, aldosterone antagonists, 5-alpha reductase inhibitors, anabolics, analgesics, analgesics, analgesics, androgens, anesthetics, anesthetics, angiotensin coverting enzyme inhibitors, anorexics, antacids, anthelmintics, antiacne agents, antiallergic agents, antialopecia agents, antiamebic agents, antiandrogen agents, antianginal agents, antiarrhythmic agents, antiarteriosclerotic agents, antiarthritic/antirheumatic agents, antiasthmatic agents, antibacterial agents, aminoglycosides, amphenicols, ansamycins, β-lactams, lincosamides, macrolides, polypeptides, tetracyclines, antibacterial agents, 2,4-diaminopyrimidines, nitrofurans, quinolones and analogs, sulfonamides, sulfones, antibiotics, anticholelithogenic agents, anticholesteremic agents, anticholinergic agents, anticoagulant agents, anticonvulsant agents, antidepressant agents, hydrazides/hydrazines, pyrrolidones, tetracyclics, antidiabetic agents, biguanides, hormones, sulfonylurea derivatives, antidiarrheal agents, antiduretic agents, antidotes, antidote, antidote, antidote, antidote, antidyskinetic, antieczematic, antiemetic agents, antiepileptic agents, antiestrogen agents, antifibrotic agents, antiflatulent agents, antifungal agents, polyenes, allylamines, imidazoles, triazoles and antiglaucoma agents.

Other therapetic agents include anti-viral agents, antifusogenic agents, blood brain barrier peptides (BBB peptides), RGD peptides, glucagon-like peptides, antigonadotropin, antigout, antihemorrhagic and antihistaminic agents; alkylmaine derivatives, aminoalkyl ethers, ethylenediamine derivatives, piperazines and tricyclics, antihypercholesterolemic, antihyperlipidemic, anthyperlipidemic and antihyperlipoproteinemic agents, aryloxyalkanoic acid derivatives, bile acid sequesterants, hmg coa reductase inhibitors, nicotine acid derivatives, thyroid hormones/analogs, antihyperphosphatemic, antihypertensive agents, arlethanolamine derivatives, arloxypropanolamine derivatives, benzothiadiazine derivatives, n-carboxyalkyl derivatives, dihydropyridine derivatives, guanidine derivatives, hydrazines/phthalazines, imidazole derivatives, quaternary ammonium compounds, quinazolinyl piperazine derivatives, reserpine derivatives, sulfonamide derivatives, antihyperthyroid agents, antihypotensive agents, antihypothyroid agents, anti-infective agents, antiinflammatory agents, anti-inflammatory agents, aminoarylcarboxylic acid derivatives, arylacetic acid derivatives, arylbutyric acid derivatives and arylcarboxylic acids.

Therapeutic agents also include arylpropionic acid derivatives, pyrazoles, pyrazolones, salicylic acid derivatives, thiazinecarboxamides, antileprotic, antileukemic, antilipemic, antilipidemic, antimalarial, antimanic, antimethemoglobinemic, antimigraine, antimycotic, antinauseant, antineoplastic and alkylating agents, antimetabolites, enzymes, androgens, antiadrenals, antiandrogens, antiestrogens, Ih-rh analogs, progestogens, adjunct, folic acid replenisher, uroprotective and antiosteporotic agents Therapeutic agents also include antipagetic, antiparkinsonian, antiperistaltic, antipheochromocytoma, antipneumocystis, antiprostatic hypertrophy, antiprotozoal, antiprozoal, antipruritic, antipsoriatic and antipsychotic agents, butyrophenes, phenothiazines, thioxanthenes, antipyretic, antirheumatic, antirickettsial, antiseborreheic and antiseptic/disinfectant agents, alcohols, aldehydes, dyes, guanidines, halogens/halogen compounds, mercurial compounds, nitrofurans, peroxides/permanganates, phenols, quinolines, silver compounds, others, antispasmodic, antisyphilitic, antithrombotic, antitubercular, antitumor, antitussive, antiulcerative, antiurolithic, antivenin, antivertigo and antiviral agents, purines/pyrimidinomes, anxiolytic, arylpiperazines, benzodiazepine derivatives, carbamates, astringent, benzodiazepine antagonist, beta-blocker, bronchodilator, ephedrine derivatives, calcium channel blockers, arylalkylamines, dihydropyridine derivatives, piperazine derivatives, calcium regulators, calcium supplements, cancer chemotherapy agents, capillary protectants, carbonic anhydrase inhibitors, cardiac depressants, cardiotonic, cathartic, cation-exchange resin, cck antagonists, central stimulants,cerebral vasodilators, chelating agents, cholecystokinn antagonists, choleitholytic agents, choleretic agents, cholinergic agents, cholinesterase inhibitors, cholinesterase reactivators, cns stimulants, cognition activators, contraceptives, agents to control intraocular pressure, converting-enzyme inhibitors, coronary vasodilators, cytoprotectants, debriging agenta, decongestanta, depigmentora, dermatitis herpretiformis suppresanta, diagnostic aids, digestive aids, diuretics, benthothiadiazine derivatives, organomercurials, pteridines, purines, steroids, sulfanamide derivatives, uracils, others, dopamine and receptor agonists.

Therapeutic agents also include dopamine receptor antagonists, ectoparasiticides, electrolyte replenishers, emetics, enzymes, digestive agents, mucolytic agents, penicillin inactivating agents, proteolytic agents, enzyme inducers, estrogen antagonists, expectorant gastric and pancreatic secreation stimulantd, gastric proton pump inhibitor, gastric secretion inhibitord, glucocorticoidd, α-glucosidase inhibitord, gonad-stimulating principled, gonadotrophic hormoned, gout suppressant, growth hormone inhibitor, growth hormone releasing factor, growth stimulant, hematinic, hemolytic, demostatic, heparin antagonist, hepatoprotectant, histamine $h_1$-receptor antagonists, histamine $h_2$-receptor antagonists, hmg coa reductase inhibitor, hypnotic, hypocholesteremic and hypolipidemic agents.

Therapeutic agents also include hypotensive, immunomodulators, immunosuppressants, inotrophic agents, keratolytic agents, lactation stimulating hormone, laxative/cathargic, Ih-rh agonists, lipotrophic agents, local anesthetics, lupus erythematosus suppressants, major tranquilizers, mineralocorticoids, minor tranquilizers, miotic agents, monoamine oxidase ihibitors, mucolytic agents, muscle relaxants, mydriatic agents, narcotic agents; analgesics, narcotic antagonists, nasal decongestants, neuroleptic agents, neuromuscular blocking agents, neuroprotective agents, nmda antagonists, nootropic agents, nsaid agents, opioid analgesics, oral contraceptives and ovarian hormones.

Therapeutic agents also include oxytocic agents, blood brain barrier protiens, GP-41 peptides, insulinotropic peptides parasympathomimetic agents, pediculicides, pepsin inhibitors, peripheral vasodilators, peristaltic stimulants, pigmentation agents, plasma volume expanders, potassium channel activators./openers, pressor agents, progestogen, prolactin inhibitors, prostaglandin/prostaglandin analogs, protease inhibitors, proton pump inhibitors, 5α-reductase inhibitors, replenishers/supplements, respiratory stimulants, reverse transcriptase inhibitors, scabicides, sclerosing agents, sedative/hypnotic agents, acyclic ureides, alcohols, amides, barbituric acid derivatives, benzodiazepine derivatives, bromides, carbamates, chloral derivatives, quinazolone derivatives and piperidinediones.

Therapeutic agents also include serotonin receptor agonists, serotonin receptor antagonists, serotonin uptake inhibitors, skeletal muscle relaxants, somatostatin analogs, spasmolytic agents, stool softeners, succinylcholine synergists, sympathomimetics, thrombolytics, thyroid hormone, thyroid inhibitors, thyrotrophic hormone, tocolytic, topical protectants, uricosurics, vasodilators, vasopressors, vasoprotectants, vitamin/vitamin sources, antichitic, antiscorbutic and antixerophthalmic agents, enzyme co-factors, hematopoietic, prombogenic agents and xanthene oxidase inhibitors.

Diagnostic Imaging Agents

Diagnostic imaging agents are agents useful in imaging the mammalian vascular system and include such agents as position emission tomography (PET) agents, computerized tomography (CT) agents, magnetic resonance imaging (MRI) agents, nuclear magnetic imaging agents (NMI), fluroscopy agents and ultrasound contrast agents. Diagnostic agents of interest include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, etc.

Wound Healing Agents

Wound healing agents are agents that promote wound healing. Wound healing agents include integrins, cell adhesion molecules such as ICAM, ECAM, ELAM and the like, antibiotics, growth factors such as EGF, PDGF, IGF, bFGF, aFGF and KGF, fibrin, thrombin, RGD peptides and the like.

Antiproliferatives

Antiproliferatives include antimetabolites, topoisomerase inhibitors, folic acid antagonists like methotrexate, purine antagonists like mercaptopurine, azathioprine, and pyrimidine antagonists like fluorouracil, cytarabine and the like.

Antioxidants

Antioxidants are agents that prevents oxidative damage to tissue and include aspartate, orotate, tacophenol derivative (vitamin E), and free radical scavengers such as SOD, glutathione and the like.

Mammalian cells are continuously exposed to activated oxygen species such as superoxide, hydrogen peroxide, hydroxyl radical, and singlet oxygen. These reactive oxygen intermediates are generated in vivo by cells in response to aerobic metabolism, catabolism of drugs and other xenobiotics, ultraviolet and x-ray radiation, and the respiratory burst of phagocytic cells (such as white blood cells) to kill invading bacteria such as those introduced through wounds. Hydrogen peroxide, for example, is produced during respiration of most living organisms especially by stressed and injured cells.

Active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5,6-double bond, which reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material.

Antioxidants have been shown to inhibit damage associated with active oxygen species. For example, pyruvate and other alpha-ketoacids have been reported to react rapidly and stoichiometrically with hydrogen peroxide to protect cells from cytolytic effects, O'Donnell-Tormey et al., J. Exp. Med., 165, pp. 500–514 (1987).

Anti-infective Agents

Anti-infective agents are agents that inhibit infection and include anti-viral agents, anti-fungal agents and antibiotics.

Anti-Viral Agents

Anti-viral agents are agents that inhibit virus and include vidarabine, acyclovir and trifluorothymidine.

Anti-Fungal Agents

Anti-fungal agents are agents that inhibit fungal growth. Anti-fungal agents include anphoterecin B, myconazole, terconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine and fluconazole.

Antibiotics

Antibiotics are natural chemical substances of relatively low molecular weight produced by various species of microorganisms, such as bacteria (including Bacillus species), actinomycetes (including Streptomyces) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the beta-lactams, including the penicillins, cephalosporins and monobactams; (2) the aminoglycosides, e.g. gentamicin, tobramycin, netilmycin, and amikacin; (3) the tetracyclines; (4) the sulfonamides and trimethoprim; (5) the fluoroquinolones, e.g. ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Anti-Cancer Agents

Anti-cancer agents (chemotherapeutic agents) are natural or synthetic molecules which are effective against one or more forms of cancer. This definition includes molecules which by their mechanism of action are cytotoxic (anti-cancer chemotherapeutic agents), those which stimulate the immune system (immune stimulators) and modulators of angiogenesis. The outcome in either case is the slowing of the growth of cancer cells.

Anti-cancer therapy include radioactive isotopes such as $^{32}$P used in the treatment of polycythemia vera and in chronic leukemia. Radioactive phosphorus has a biological half-life of about 8 days in humans. It emits beta rays that exert a destructive effect on the rapidly multiplying cells. $^{32}$P is usually administered in doses of about 1 mc daily for 5 days. Either the oral or intravenous route may be used and the doses are not greatly different. Radioactive iodine $^{131}$I, radioactive gold $^{198}$Au, and other isotopes are not as useful as $^{32}$P. Nevertheless, $^{131}$I has some limited applications in metastatic thyroid carcinoma. Other radioactive isotopes can be used with our technology either as complexes of radioactive metal such as $^{51}$Cr, $^{52}$Mn, $^{52}$Mg, $^{57}$Ni, $^{55}$Co and $^{56}$P, $^{55}$Fe, $^{103}$Pd, $^{192}$Ir, $^{64}$Cu and $^{67}$Cu or as chelates of these metals using bifunctional chelating agents like (BFCs), 6-[p-(bromoacetamido)benzyl]-1,4,8,11-tetraazacyclotetradecane-1,4,8,11-tetraacetic acid (BAT), 6-[p-(isothiocyanato)benzyl]-1,4,8,11-tetraazacyclotetradecane-1,4,8,11-tetraacetic acid (SCN-TETA), 4-[(1,4,8,11-tetraazacyclotetradec-1-yl)methyl]benzoic acid (CPTA), and 1-[(1,4,7,10,13-pentaazacyclopentadec-1-yl)methyl]benzoic acid (PCBA).

Numerous drugs fall into the category of chemotherapeutic agents useful in the treatment of neoplastic disease that are amenable to the embodiment of this application. Such agents derivitized with this technology can include antimetabolites such as metotrexate (folic acid derivatives), fluoroaucil, cytarabine, mercaptopurine, thioguanine, petostatin (pyrimidine and purine analogs or inhibitors), a variety of natural products such as vincristine and vinblastine (vinca alkaloid), etoposide and teniposide, various antibiotics such as miotomycin, plicamycin, bleomycin, doxorubicin, danorubicin, dactomycin; a variety of biological response modifiers including interferon-alpha; a variety of miscellaneous agents and hormonal modulators including cisplatin, hydroxyurea, mitoxantorne, procarbozine, aminogultethimide, prednisone, progestins, estrogens, anti-estorgens such as tamoxifen, androgenic steroids, antiadrogenic agents such as flutamide, gonadotropin releasing hormones analogs such as leuprolide, the matrix metalloprotease inhibitors (MMPIs) as well as anti-cancer agents including Taxol (paclitaxel) and related molecules collectively termed taxoids, taxines or taxanes.

Included within the definition of "taxoids" are various modifications and attachments to the basic ring structure (taxoid nucleus) as may be shown to be efficacious for reducing cancer cell growth and which can be constructed by organic chemical techniques known to those skilled in the art.

Chemotherapeutics include podophyllotoxins and their derivatives and analogues. Another important class of chemotherapeutics useful in this invention are camptothecins.

Another preferred class of chemotherapeutics useful in this invention are the anthracyclines (adriamycin and daunorubicin).

Another important class of chemotherapeutics are compounds which are drawn from the following list: Taxotere, Amonafide, Illudin S, 6-hydroxymethylacylfulvene Bryostatin 1, 26-succinylbryostatin 1, Palmitoyl Rhizoxin, DUP 941, Mitomycin B, Mitomycin C, Penclomedine, angiogenesis inhibitor compounds, Cisplatin hydrophobic complexes such as 2-hydrazino-4,5-dihydro-1 H-imidazole with platinum chloride and 5-hydrazino-3,4-dihydro-2H-pyrrole with platinum chloride, vitamin A, vitamin E and its derivatives, particularly tocopherol succinate.

Other compounds useful in the invention include: 1,3-bis(2-chloroethyl)-1-nitrosurea ("carmustine" or "BCNU"), 5-fluorouracil, doxorubicin ("adriamycin"), epirubicin, aclarubicin, Bisantrene(bis(2-imidazolen-2-ylhydrazone)-9, 10-anthracenedicarboxaldehyde, mitoxantrone, methotrexate, edatrexate, muramyl tripeptide, muramyl dipeptide, lipopolysaccharides, vidarabine and its 2-fluoro derivative, resveratrol, retinoic acid and retinol, carotenoids, and tamoxifen.

Other chemotherapeutic agents useful in the application of this invention include: Decarbazine, Lonidamine, Piroxantrone, Anthrapyrazoles, Etoposide, Camptothecin, 9-aminocamptothecin, 9-nitrocamptothecin, camptothecin-11 ("Irinotecan'), Topotecan, Bleomycin, the Vinca alkaloids and their analogs [Vincristine, Vinorelbine, Vindesine, Vintripol, Vinxaltine, Ancitabine], 6-aminochrysene, and Navelbine.

Other compounds useful in the application of the invention are mimetics of taxol, eleutherobins, sarcodictyins, discodermolides and epothiolones.

Antineoplastic Agents

Antineoplastic agents are anti-cancer agents such as fluoropyrimidines, pyrimidine nucleosides, purines, platinum analogs, anthracyclines/anthracenediones, podophyllotoxins, camptothecins, hormones and hormonal analogs, enzymes, proteins and antibodies, vinca alkaloids, taxanes, atihormonal agents, antifolates, antimicrotubule agents, alkylating agents (classical and non-classical), antimetabolites, antibiotics, topoisomerase inhibitors, antivirals, and miscellaneous cytotoxic agents, for example hydroxyurea, mitotane, fusion toxins, PZA, bryostatin, retinoids, butyric acid and derivatives, pentosan, fumagillin, and others. The objective of all antineoplastic drugs is to eliminate (cure) or to retard the growth and spread (remission) of cancer cells. The majority of the above listed antineoplastic agents pursue this objective by possessing primary cytotoxic activity, effecting a direct kill on the cancer cells. Other antineoplastic drugs stimulate the body's natural immunity to effect cancer cell death.

Matrix Metalloprotease Inhibitors (MMPIS)

Also known as matrix metalloproteinase inhibitors, MMPIs are inhibitors of the matrix metalloproteases. The metalloproteases are a family of enzymes containing zinc at the active site, which facilitate the catalytic hydrolysis of various protein substrates. A subfamily of the metalloprotease family is known as the matrix metalloproteases (MMPs) because these enzymes are capable of degrading the major components of articular cartilage and basement membranes. The matrix metalloproteases include stromelysin, collagenase, matrylisin and gelatinase, among other. The action of matrix metalloptoreases is inhibited by MMPIs used in the preparation of the derivatized MMPIs of the present invention. Some characterized MMPs and their preferred substrates are illustrated in the following table.

The nomenclature used to describe the interaction of proteases and their substrates is widely used in the protease literature. In this system, the binding site for a polypeptide substrate on a protease is envisioned as a series of subsites; each subsite interacts with one amino acid reside of the substrate. By convention, the substrate amino acid residues are called P (for peptide); the subsites on the protease that interact with the substrate are called S (for subsite). The subsites are in the catalytic or active site of the protease. The amino acid residues on the amino-terminal side of the scissile bond (bond that is cleaved on the substrate) are numbered $P_1$, $P_2$, $P_3$, etc., and the residues on the carboxy-terminal side of the scissile bond are numbered $P_1'$, $P_2'$, $P_3'$, etc. The residues can be numbered up to $P_6$ on each side of the scissile bond. The subsites on the protease are termed $S_3$, $S_2$, $S_1$, $S_1'$, $S_2'$, $S_3'$, etc. to complement the substrate residues that interact with the enzyme.

Characterized MMPs and their preferred substrates.

| MATRIX METALLO-PROTEINASE | MMP NUMBER | PREFERRED SUBSTRATE |
|---|---|---|
| CLASS I | | |
| Interstitial collagenase | 1 | Fibrillar collagens, type I, II, III |
| Neutrophil (PMN) collagenase | 8 | Fibrillar collagens, type I, II, III |
| Collagenase-3 | 13 | Fibrillar collagens, type I, II, III |
| Collagenase 4 | 18 | |
| CLASS II | | |
| Gelatinase A (72 kDa) | 2 | Collagen types IV, V, gelatin |
| Gelatinase B (92 kDa) | 9 | Collagen types IV, V, gelatin |
| Metalloelastase | 12 | Elastin |
| CLASS III | | |
| Stromelysin-1 | 3 | Laminin, fibronectin, proteoglycans |
| Stromelysin-2 | 10 | Laminin, fibronectin, proteoglycans |
| Matrylisin (pump) | 7 | Laminin, fibronectin, proteoglycans |
| NON-CLASSIFIED | | |
| Stromelysin-3 | 11 | 1-antitrypsin |
| Membrane-type MMP | 14–17 | Pro-gelatinase A |

In this application, the term MMPI should be understood to include matrix metalloprotease inhibitors as well as analogs thereof. In addition, the term MMPI includes optical isomers and diastereomers; as well as the racemic and resolved, enantiomerically pure R and S stereoisomers; as well as other mixtures of the R and S stereoisomers and pharmaceutically acceptable salts thereof.

Oxytocin

Oxytocin is a hormone involved in the enhancement of lactation, contraction of the uterus, and relaxation of the pelvis prior to childbirth. Oxytocin secretion in nursing women is stimulated by direct neural feedback obtained by stimulation of the nipple during suckling. Its physiological effects include the contraction of mammary gland myoepithelial cells, which induces the ejection of milk from mammary glands, and the stimulation of uterine smooth muscle contraction leading to childbirth. Oxytocin causes myoepithelial cells surrounding secretory acini of mammary glands to contract, pushing milk through ducts. In addition, it stimulates the release of prolactin, and prolactin is trophic on the breast and stimulates acinar formation of milk.

Cholecystokinin (CCK)

CCK is a polypeptide of 33 amino acids originally isolated from pig small intestine that stimulates gallbladder contraction and bile flow and increases secretion of digestive enzymes from pancreas. It exists in multiple forms, including CCK-4 and CCK-8, with the octapeptide representing the dominant molecular species showing the greatest activity. It belongs to the CCK/gastrin peptide family and is distributed centrally in the nervous system and peripherally in the gastrointestinal system. It has many biological roles, including stimulation of pancreatic secretion, gall bladder contraction and intestinal mobility in the GI tract as well as the possible mediation of satiety and painful stimuli.

Antihypertensive Agents

Antihypertensive agents are various agents that can be used to treat hypertension, including but not limited to enalapril, acebutolol, and doxazosin. Enarlapril is a pro-drug that is activated to the angiotensin-converting enzyme (ACE) inhibitor, enalaprilat. This pro-drug inhibits the conversion of angiotensin I to angiotensin II and exerts an antihypertensive effect by suppressing the renin-angiotensin-aldosterone system. Acebutolol is in a class of drugs called beta-blockers, which affect the heart and circulatory system. Acebutolol is used to lower blood pressure, lower heart rate, and reduce angina (chest pain). Doxazosin is a member of the alpha blocker family of drugs used to lower blood pressure in people with hypertension. Doxazosin is also used to treat symptoms of benign prostatic hyperplasia (BPH). Doxazosin works by relaxing blood vessels so that blood passes through them more easily, which helps to lower blood pressure.

Methylprednisolone

Methylprednisolone is a synthetic steroid that suppresses acute and chronic inflammation. In addition, it stimulates gluconeogenesis, increases catabolism of proteins and mobilization of free fatty acids. In addition, it potentiates vascular smooth muscle relaxation by beta adrenergic agonists, and may alter airway hyperactivity. It is also a potent inhibitor of the inflammatory response.

GP-41 Peptides

GP-41 is an HIV transmembrane protein which has been shown to be essential for the virus to fuse with and infect healthy cells.

Anti-viral and Antifusogenic Peptides

Anti-viral peptides refers to peptides that inhibit viral infection of cells, by, for example, inhibiting cell-cell fusion or free virus infection. The route of infection may involve membrane fusion, as occurs in the case of enveloped viruses, or some other fusion event involving viral and cellular structures. Peptides that inhibit viral infection by a particular virus may be referenced with respect to that particular virus, e.g., anti-HIV peptide, anti-RSV peptide, etc. Antifusogenic peptides are peptides demonstrating an ability to inhibit or reduce the level of membrane fusion events between two or more entities, e.g., virus-cell or cell-cell, relative to the level of membrane fusion that occurs in the absence of the peptide.

In particular, anti-viral and antifusogenic peptides include the DP107 and DP178 peptides and analogs thereof, as well as peptides comprised of amino acid sequences from other (non-HIV) viruses that correspond to the gp41 region of HIV from which DP107 and DP178 are derived, and that exhibit anti-viral or anti-fusogenic activity. These peptides can exhibit anti-viral activity against not only HIV, but other viruses including human respiratory syncytial virus (RSV), human parainfluenza virus (HPV), measles virus (MeV) and simian immunodeficiency virus (SIV).

In particular, anti-HIV peptides refer to peptides that exhibit anti-viral activity against HIV, including inhibiting CD4+ cell infection by free virus and/or inhibiting HIV-induced syncytia formation between infected and uninfected CD4+ cells. Anti-SIV peptides are peptides that exhibit anti-viral activity against SIV, including inhibiting of infection of cells by the SIV virus and inhibiting syncytia formation between infected and uninfected cells. Anti-RSV peptides are peptides that exhibit anti-viral activity against RSV, including inhibiting mucous membrane cell infection by free RSV virus and syncytia formation between infection and uninfected cells. Anti-HPV peptides are peptides that exhibit anti-viral activity against HPV, including inhibiting infection by free HPV virus and syncytia formation between infected and uninfected cells. Anti-MeV peptides are peptides that exhibit anti-viral activity against MeV, including inhibiting infection by free MeV virus and syncytia formation between infected and uninfected cells.

Blood Brain Barrier (BBB) Peptides

The "blood-brain barrier" is a layer of cells that controls which substances may penetrate from the general circulation into the brain. BBB proteins can traverse this barrier through protein transduction. Small sections of these proteins (10–16 residues long), i.e. BBB peptides, are responsible for this transduction.

RGD Peptides

The RGD peptide for conjugation to tissues or fixed endogenous proteins in accordance with the present invention includes a sequence of amino acids, preferably naturally occurring L-amino acids and glycine, having the following formula:

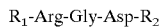

$R_1$-Arg-Gly-Asp-$R_2$

In this formula, $R_1$ and $R_2$ represent an amino acid or a sequence of more than one amino acid or a derivatized or chemically modified amino acid or more than one derivatized or chemically modified amino acids.

Insulinotropic Peptides

Insulinotropic peptides (ITPs) are peptides with insulinotropic activity. Insulinotropic peptides stimulate, or cause the stimulation of, the synthesis or expression of the hormone insulin. Such peptides include precursors, analogues, fragments of peptides such as Glucagon-like peptide, exendin 3 and exendin 4 and other peptides with insulinotropic activity.

Glucagon-Like Peptide

Glucagon-Like Peptide (GLP) and GLP derivatives are intestinal hormones which generally simulate insulin secretion during hyperglycemia, suppresses glucagon secretion, stimulates (pro) insulin biosynthesis and decelerates gastric emptying and acid secretion. Some GLPs and GLP derivatives promote glucose uptake by cells but do not simulate insulin expression as disclosed in U.S. Pat. No. 5,574,008 which is hereby incorporated by reference.

Pulmonary Condition

A pulmonary condition is a disease which affects lung function. Such conditions may result from a defect in a gene or genes associated with lung function (e.g., cystic fibrosis), asthma, allergies, an immune or autoimmune disorder, a microbial infection (e.g. bacterial, viral, fungal or parasitic infection), or a mechanical injury to the lungs.

Exemplary pulmonary conditions contemplated by the subject invention include cystic fibrosis, asthmatic bronchitis, tuberculosis, bronchitis, bronchiectasis, laryngotracheobronchitis, bronchiolitis, emphysema, bronchial pneumonia, allergic bronchopneumonia, viral pneumonia, pertussis, diphtheria, spasmodic croup, pulmonary phthisis, encephalitis with retained secretions, and pulmonary edema. Other pulmonary conditions, such as those which develop as a result of injury or surgery (e.g., after tracheotomy), as well as those associated with insufficient surfactant secretion in the lungs of premature infants, are also contemplated by the subject invention. Pulmonary conditions amenable to treatment by the subject method may also develop as a result of activity associated with inhalation of particulate matter e.g. smoking, exposure to construction areas or other high dust areas, occupational hazards associated with inhalation of particulates, exposure to environmental particulates (e.g. smog, pollen, asbestos, siliconis), pulmonary delivery of pharmaceutical agents (e.g. bronchodilators) or inhalation of cocaine.

Other pulmonary conditions include diffuse parenchymal lung disease from infectious cases, such as cytomegaloviral pneumonia or miliary tuberculosis, drug-induced lung disease (after administration of penicillin, nitrofurantoin), neoplastic lung disease having lymphangitic spread pattern or bronchoalveolar cell carcinoma, granulomatous disease (infectious or noninfectious), hypersensitivity pneumonitis, histoplasmosis, tuberculosis, idiophatic pulmonary fibrosis (aka cryptogenic fibrosing alveolitis), hereditary pulmonary disorders, such as alveolar microlithiasis and bronchiectasis, eosinophilic granuloma, lympphangioleimyomatosis, and plumonary alveolar proteinosis disorder.

Symptoms of a Pulmonary Condition

Symptoms of a pulmonary condition are symptoms associated with any of the pulmonary conditions described above. The classic symptoms associated with such pulmonary conditions may include coughing, exertional dyspnea, wheezing, chest pain and purulent sputum production. Other components of the syndrome which may accompany a pulmonary condition include hypoxia, $CO_2$ narcosis, hyperventilation, decreased expiration volume, and decreased lung capacity.

Pulmonary Fluid

Pulmonary fluid is the fluid which bathes the apical surface of the lung epithelium, particularly the alveolar epithelium and contains fixed and mobile pulmonary fluid components.

Pulmonary Delivery Agent

Pulmonary delivery agents are agents that may be delivered to the lungs. Such agents include therapeutic agents.

Fixed Pulmonary Components

Fixed pulmonary components are non-mobile pulmonary components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts.

Mobile Pulmonary Components

Mobile pulmonary components are pulmonary components that do not have a fixed situs for any extended period of time, generally not exceeding 5, more usually one minute. Mobile pulmonary components are components of the pulmonary or lung fluid and include such soluble proteins such as immunoglobulins, serum albumin, ferritin, transferrin and the like.

Blood Components

Blood components may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5, more usually one minute. These blood components are not membrane-associated and are present in the blood for extended periods of time and are present in a minimum concentration of at least 0.1 µg/ml. Mobile blood components include serum albumin, transferrin, ferritin and immunoglobulins such as IgM and IgG. The half-life of mobile blood components is at least about 12 hours.

Inhaler Device

An inhaler device is any device useful in the administration of the inhalable medicament of the invention. Examples of inhaler devices include nebulizers, metered dose inhalers, dry powder inhalers, intermittent positive pressure breathing apparatuses, humidifiers, bubble environments, oxygen chambers, oxygen masks and artificial respirators.

Reactive Groups

Reactive groups are chemical groups capable of forming a covalent bond. Such reactive groups are coupled or bonded to a therapeutic or diagnositic agent. Reactive groups will generally be stable in an aqueous environment and will usually be carboxy, phosphoryl, or convenient acyl group, either as an ester or a mixed anhydride, an imidate or maleimide, thereby capable of forming a covalent bond with functionalities such as an amino group, a hydroxy or a thiol at the target site on pulmonary components. For the most part, the esters will involve phenolic compounds, or be thiol esters, alkyl esters, phosphate esters, or the like. Prefereably, the reactive group will be a maleimide group.

Functionalities

Functionalities are groups on pulmonary components to which reactive groups on modified therapeutic agents react to form covalent bonds. Functionalities include hydroxyl groups for bonding to ester reactive entities; thiol groups for bonding to maleimides, imidates and thioester groups; amino groups for bonding to carboxy, phosphoryl or acyl groups and carboxyl groups for bonding to amino groups.

$IC_{50}$

Concentration of an enzyme inhibitor at which 50% of the enzymatic activity is inhibited.

Protective Groups

Protective groups are chemical moieties utilized to protect reactive entities from reacting with other functionalities. Various protective groups are disclosed in U.S. Pat. No. 5,493,007 which is hereby incorporated by reference. Such protective groups include acetyl, fluorenylmethyloxycarbonyl (FMOC), t-butyloxy carbonyl (BOC), benzyloxycarbonyl (CBZ), and the like. For small organic molecules all protecting groups like tetrahydropyranyl (THP), all silyl derivatives, acetals, thioacetals and the like.

Linking Groups

Linking groups are chemical moieties that link or connect reactive groups to therapeutic agents. Linking groups may comprise one or more alkyl moeities, alkoxy moeity, alkenyl moeity, alkynyl moeity or amino moeity substituted by alkyl moeities, cycloalkyl moeity, polycyclic moeity, aryl moeity, polyaryl moeities, substituted aryl moeities, heterocyclic moeities, and substituted heterocyclic moeities. Linking groups may also comprise poly ethoxy amino acids, such as AEA ((2-amino) ethoxy acetic acid) or a preferred linking group AEEA ([2-(2-amino) ethoxy)]ethoxy acetic acid.

Sensitive functional groups

A sensitive functional group is a group of atoms that represents a potential reaction site on a therapeutic agent. If present, a sensitive functional group may be chosen as the attachment point for the linking group-reactive group modification. Sensitive functional groups include but are not limited to carboxyl, amino, thiol, and hydroxyl groups.

Modified Therapeutic and Diagnostic Agents

Modified therapeutic and diagnostic agents are agents that have been modified by attaching a reactive group. The reactive group may be attached to the therapeutic agent either via a linking group, or optionally without using a linking group. Modified therapeutic and diagnostic agents may be administered in vivo such that conjugation with blood or pulmonary components occurs in vivo, or they may be first conjugated to blood or pulmonary components in vitro and the resulting conjugated therapeutic agent (as defined below) administered in vivo.

Conjugated Therapeutic and Diagnostic Agents

Conjugated therapeutic and diagnostic agents are modified therapeutic and diagnostic agents that have been conjugated to a blood or pulmonary component via a covalent bond formed between the reactive group of the modified therapeutic agent and the functionalities of the pulmonary component, with or without a linking group. As used throughout this application, the term "conjugated therapeutic agent" can be made more specific to refer to particular conjugated therapeutic agents, for example "conjugated antihistamine."

Taking into account these definitions, the present invention is directed to modified therapeutic and diagnostic agents capable of reacting with available functionalities on pulmonary or blood components via covalent linkages. The invention is also directed to methods of making the modified agents and their use. The modified therapeutic agents of the present invention are capable of reacting in vivo to form conjugates with pulmonary and/or blood components, such as pulmonary or blood proteins, thereby extending the half-life and improving bioavailability of the therapeutic agent without deterioiusly altering the agent's therapeutic effect. In preferred embodiments of this invention, the functionality on the protein will be a thiol group and the reactive group on the modified therapeutic agent will be a maleimido-containing group such as gamma-maleimide-butyralamide (GMBA), maleimidopropionic acid (MPA) or maleimide-benzoyl-succinimide (MBS).

The invention in one aspect contemplates delivery of the modified agents to the blood of a host for conjugation to blood components, including blood proteins. While pulmonary administration is further described as such a route of administration, it will be understood that the invention is not limited to such routes of adminstration, and also contemplated administration of the modified agents to a patient's blood stream using other methods, including parenterally, such as intravenously (IV), intraarterially (IA), intramuscularly (IM), subcutaneously (SC) and the like.

For pulmonary delivery, a wide variety of devices and carrier molecules have been utilized to enhance pulmonary drug delivery and can be used with the modified agents of the present invention. These devices and methods include metered dosing, carriers such as liposomes (Meisner et al, 1989) actide/glycolide copolymer (PLGA) nanospheres (Niwa et al., 1995), albumin microspheres (Feinstein et al., 1990), and other physical art forms to created aerosols or nanoparticulates.

A new type of inhalation aerosol, characterized by particles of small mass density and large size, has permitted the highly efficient delivery of inhaled therapeutics (e.g. insulin, testosterone) into the systemic circulation. Particles with mass densities less than 0.4 gram per cubic centimeter and mean diameters exceeding 5 micrometers have been reported to avoid the lungs' natural clearance mechanisms providing higher bioavailability than that. of conventional inhaled therapeutic particles. (Edwards et al., 1997). For most of these therapies, aerosols are designed to comprise small spherical droplets or particles of mass density near 1 $g/cm^3$ and mean geometric diameter between approximately 1 and 3 micron, suitable for particle penetration into the airways or lung periphery.

Studies performed primarily with liquid aerosols have shown that these characteristics of inhaled aerosols lead to optimal therapeutic effect, both for local and systemic therapeutic delivery. Inefficient drug delivery can still arise, owing to excessive particle aggregation in an inhaler, deposition in the mouth and throat, and overly rapid particle removal from the lungs by mucocilliary or phagocytic clearance mechanisms.

To address these problems, particle surface chemistry and surface roughness are traditionally manipulated. Recent data indicate that major improvements in aerosol particle performance may also be achieved by lowering particle mass density and increasing particle size, since large, porous particles display less tendency to agglomerate than (conventional) small and nonporous particles. Also, large, porous particles inhaled into the lungs can potentially release therapeutic substances for long periods of time by escaping phagocytic clearance from the lung periphery, thus enabling therapeutic action for periods ranging from hours to many days. (Edwards et al., 1998)

It has been previously reported that specific transport receptors for albumin (GP-60, albondin) exist in the endothelium that function as unique albumin carriers (U.S. Pat. No. 5,254,342). These transcytosis proteins facilitate the movement of albumin and albumin carriers across the lining of the airway and result in extensive plasma levels of these proteins or protein carriers. As further described, modified agents according to the present invention can be prepared that react with albumin, and upon pulmonary delivery, the resulting conjugates can pass to the bloodstream via such carriers.

Pulmonary drug delivery is also advantageous for local treatment of the lung in that it promotes an increase in drug retention-time in the lung and more importantly, a reduction in extrapulmonary side-effects, invariably resulting in enhanced therapeutic efficacies. (Shek, 1994). A key advantage of pulmonary delivery includes reduced systemic toxicity and increased drug concentration at the site of action (e.g. infection or inflammation site. (Stout and Derendorf, 1987).

The use of in vivo or ex vivo bioconjugation associated with pulmonary drug delivery includes the following non-limited benefits. Retention of the drug at the site of placement is enhanced due to covalently attachment of the drug to the airway site. Additionally, prolonged duration of action of the drug is made possible, both in the lung by in situ attachment to soluble proteins for localized intrapulmonary activity, as well as systemic absorption and conjugation to blood proteins.

Drug stability is improved, both locally and systemically, as conjugation affords protection against enzymatic degradation that occurs in the pulmonary mucosal fluid or in the plasma. Also, in the deep lungs, alveolar macrophages can rapidly deposited particles; the reactivity of the modified agents of the invention with epithelial cells will allow for localized retention of the agent.

Localized delivery to the pulmonary tissues also reduces toxicity and reduces systemic exposure as there is no first-pass liver effect. Systemic delivery also exhibits reduced extravascular side effects through conjugation to, for example, albumin, due to, for example, the limitation of hepatic, central nervous system (CNS) or renal toxicity due to the limited clearance of albumin into these organs.

Pulmonary delivery of the modified agents of the invention also provides advantages of improved patient compliance due to prolonged duration of action of the modified agents. In turn, cost benefits can be achieved through, e.g., reduced costs of goods per course of therapy due to prolonged duration of action, and outpatient use of medications that would otherwise have limited use or complicated dosing titration schedules. Pulmonary delivery can also reduce difficulties associated with oral dosing, including low solubility, interactions with food, and low bioavailability.

A further advantage of pulmonary delivery of modified agents of the present invention is the ability to deliver systemically large macromolecule drugs, such as insulin, growth hormones, beta-interferon, calcitonin, and others that, due to their large size and instability, are typically delivered by injection. The present invention provides an alternative and more convenient route of adminstering these drugs. In addition, many drugs and therapeutic peptides are more stable in solid, dry form, rather than solubilized. Dry pulmonary formulations of such drugs modified according to the present invention provide for a more stable form of the drug, as well as the convenience of pulmonary administration.

1. Therapeutic Agents

A wide variety of therapeutic agents are contemplated for use in the present invention, including peptide therapeutics and small organic molecules, provided they can be modified as described.

In addition to therapeutic agents discussed above, the following therapeutic agents are within the scope of this invention.

Sympathomimetic compounds mimic the action of endogenous catecholamines (adrenalinelike neurotransmitters) at peripheral sympatnetic neurons in addition to CNS effects. Adrenaline systems control important body functions like blood pressure regulation and wakefulness. A vast panoply of compounds has been developed that allows one to selectively tweak these systems. These include agonists, used as decongestants and antiasthmatics and antagonists, used as antihypertensives).

Nonselective adrenergic agents epinephrine phenylpropanolamine ephedrine

Alpha agonist
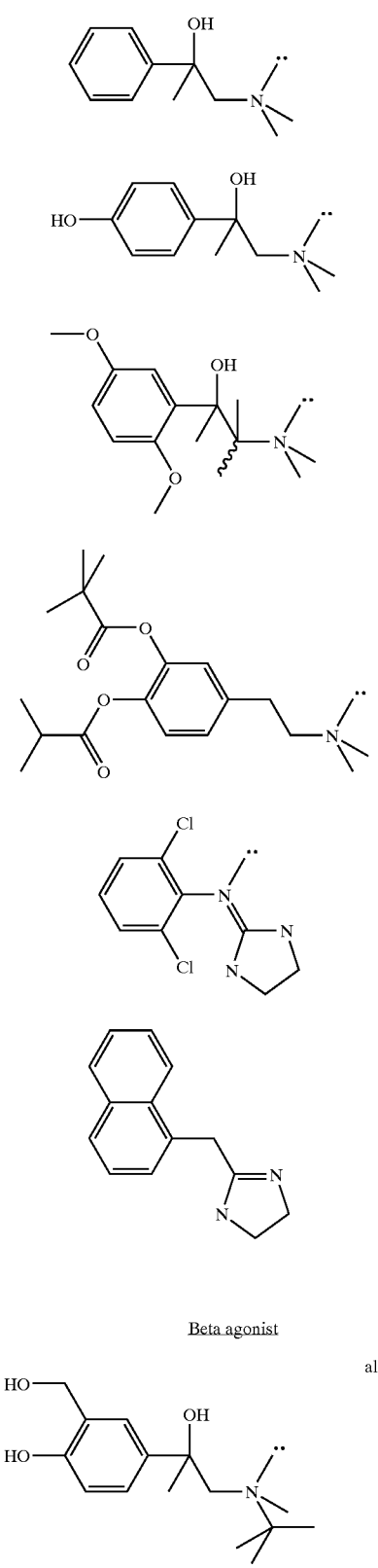
phenylephrine
synephrine
methoxamine
ibopamine
clonidine
naphazoline
Beta agonist
albuterol (Proventil)
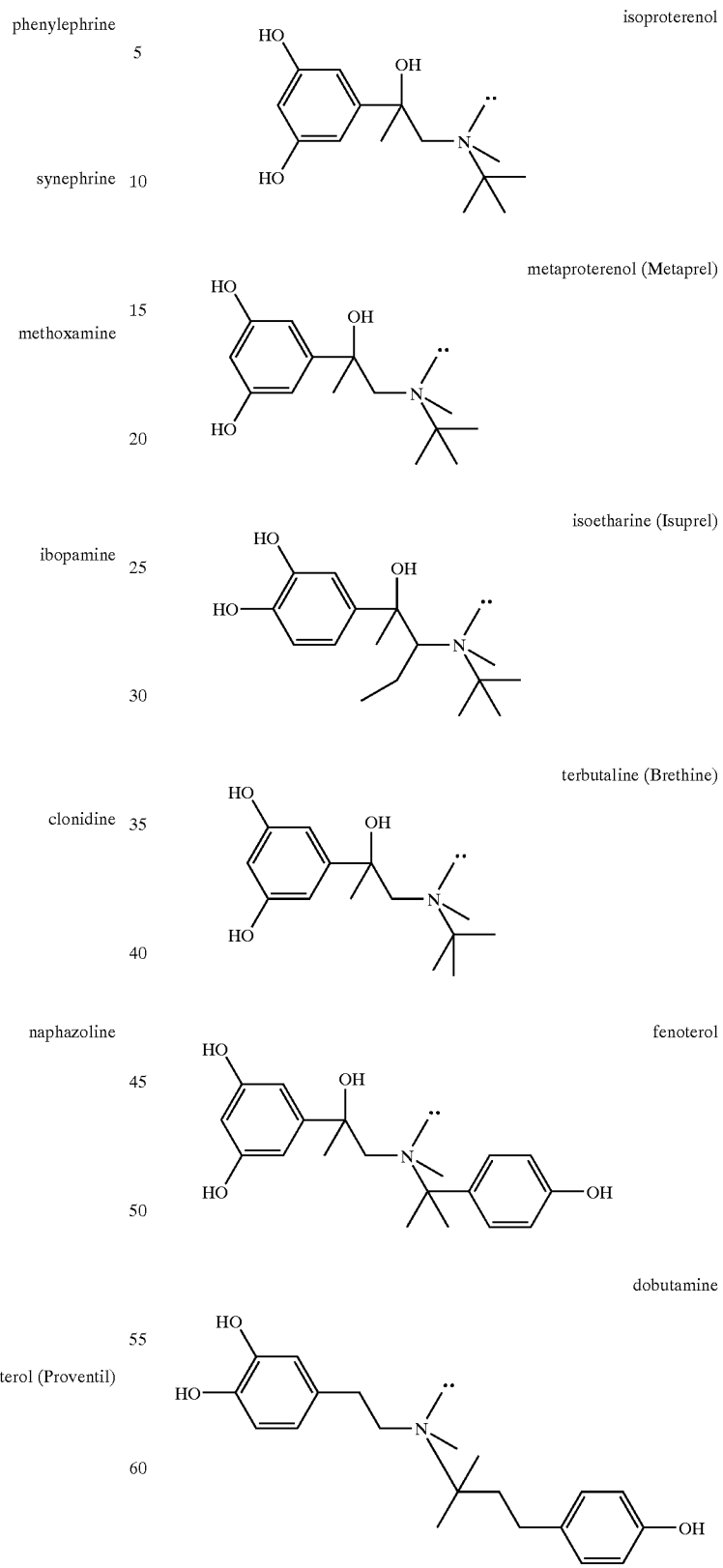
isoproterenol
metaproterenol (Metaprel)
isoetharine (Isuprel)
terbutaline (Brethine)
fenoterol
dobutamine bitolterol

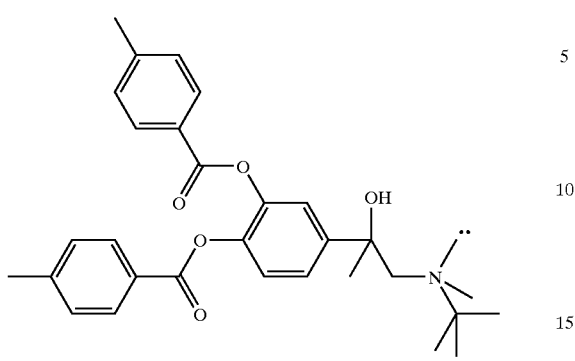

Selective agents include alpha agonists such as phenylephrine (Neo Synephrine) and more lipophilic agents such as naphazoline. Clonidine, an antihypertensive, is sometimes used in ethanol withdrawal, and has been tried in cigarette smoking cessation. It probably has a net antagonist effect through autoreceptors, i.e. presynaptic receptors detect an excess of adrenergic agonist and decrease norepinephrine release. Ibopamine, a cardiotonic, has diuretic and dopamine agonist activity.

The beta agonists are popular antiasthma medications. Isoproterenol and dobutamine are fairly selective for the beta1 receptor; the latter is used as a cardiotonic.

Nonselective adrenergic antagonists labetolol

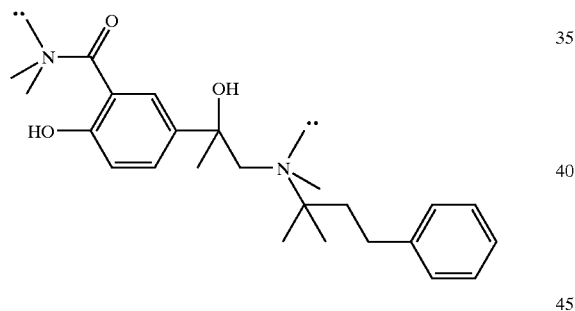

Alpha antagonists prazosin

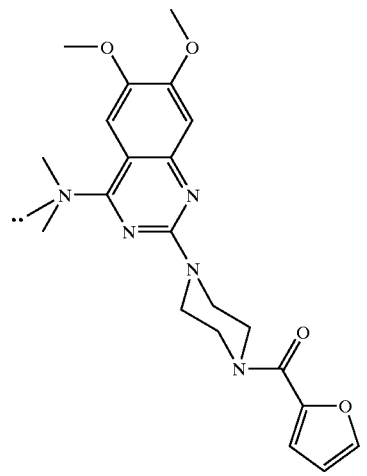

phentolamine

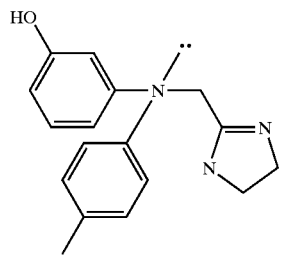

yohimbine

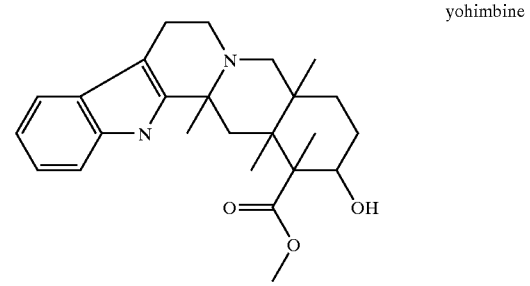

Beta antagonists propranolol

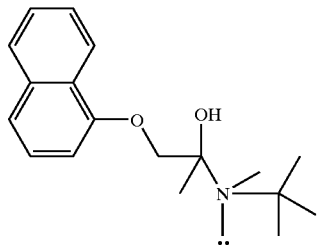

metoprolol

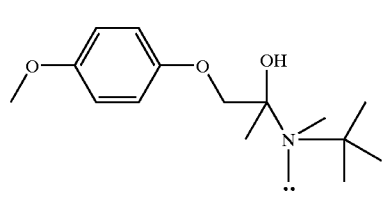

atenolol

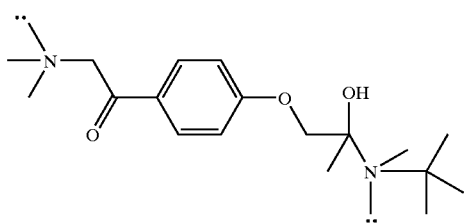

practolol

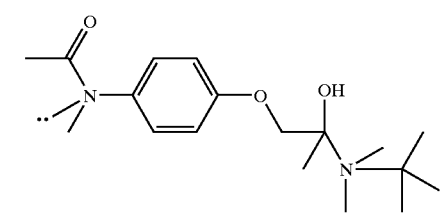

nadolol

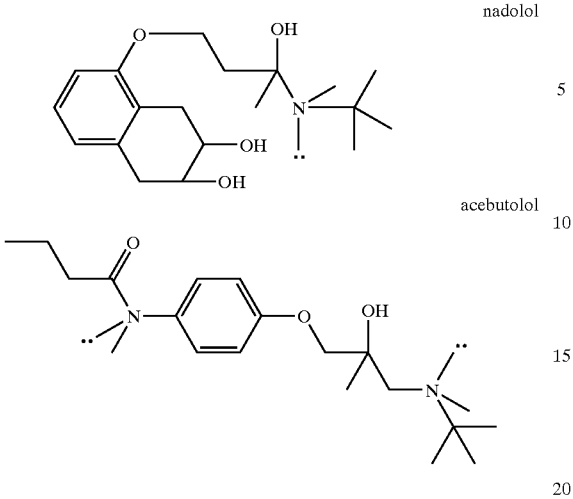

acebutolol

Alpha blockers such as phentolamine and prazosin are also used as antihypertensives. Yohimbine, a selective alpha2 blocker, is a popular aphrodisiac for males, purported to prolong or intensify erection. Alpha2 receptors are inhibitory, so that inhibiting them produces a stimulating effect. Alpha2 and alpha3 receptors are alsopresent in fat storage sites; antagonizing them may provide a way to promote fat catabolism without resorting to central stimulants.

Beta antagonists include propranolol, which has been used for some time to calm the nerves in event-specific anxiety (stage fright) as well as its more traditional role in hypertension. Acebutolol is a cardioselective beta blocker used in angina.

Antidepressants

Antidepressants work by altering the concentration of catecholamines and/or serotonin in CNS neurons emanating from the limbic system into the frontal lobe. Raising levels of catecholamines—excitatory, adrenalin-type neurotransmitters—causes stimulation. Elevating serotonin, an inhibitory neurotransmitter, produces a calming action, and results in subsequent upregulation of catecholamine systems as a mechanism of habituation.

Selective serotonin reuptake inhibitors zimeldine

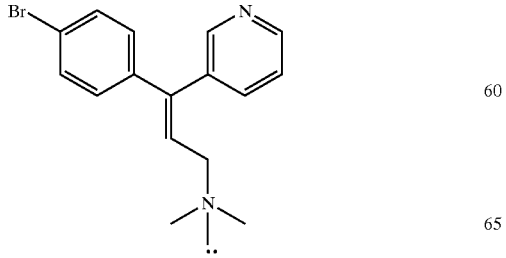

fluoxetine (Prozac)

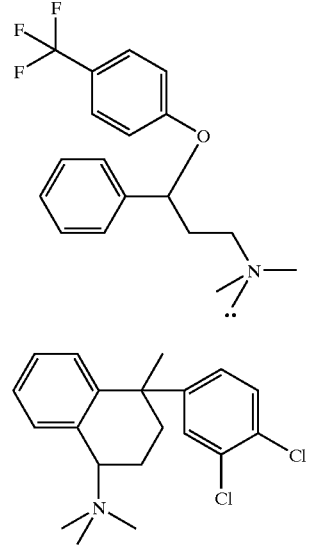

sertraline (Zoloft)

paroxetine (Paxil)

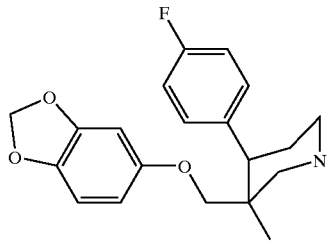

fernoxetine (Malexil)

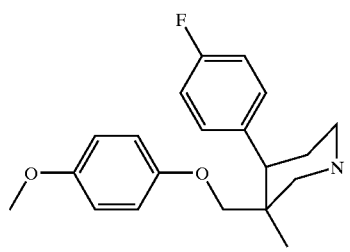

venlafaxine (Effexor)

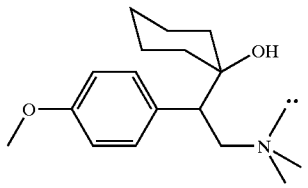

fluvoxamine (Luvox)

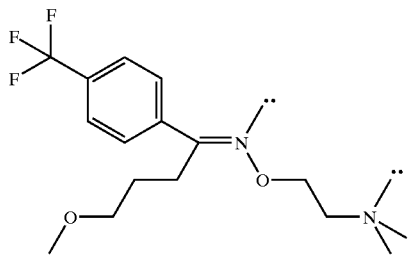

citalopram (Celexa)

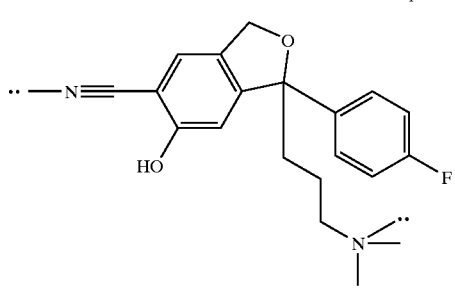

prolintane

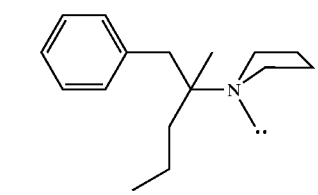

oxaflazone

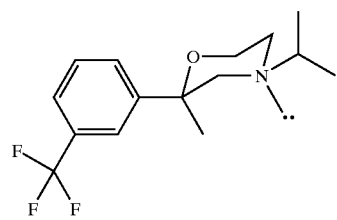

indalpine

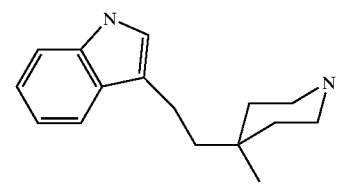

indeloxazine

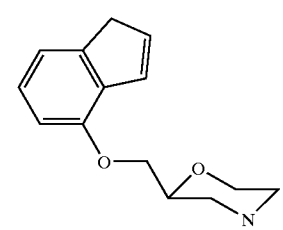

binedaline

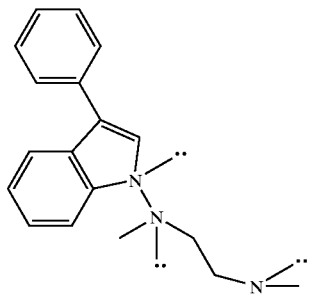

nefazodone (Serzone)

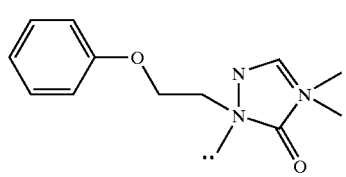

trazodone (Desyrel)

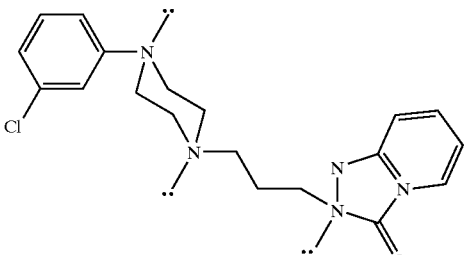

m-chloropiperazine etoperidone

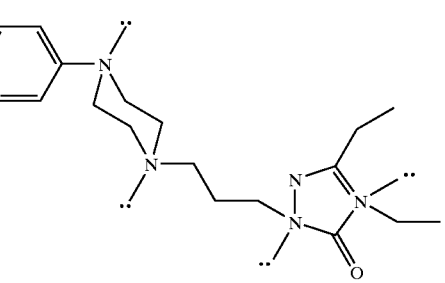

The selective serotonin reuptake inhibitors (SSRIs) inhibit reuptake of serotonin without significantly affecting adrenergic systems. The adverse effect profiles are much less than the tricyclics, since muscarinic, histaminic and adrenergic binding is much reduced.

The effect of these serotonin agents on mood has led to more complex theories of how antidepressants work. According to one hypothesis, the noradrenergic systems (dopamine, noradrenalin) which underlie the serotonin systems respond to an increase in the inhibitory serotonin function by upregulating, or increasing the number of receptors on the individual post-synaptic neural surface. This increase in adrenaline-type neural function might then account for the antidepressant activity which is delayed from the onset of serotonin reuptake inhibition by several weeks. Another possibility is that the serotonin receptors take a while to register the excess serotonin and resopond with similar mechanisms. In addition, recent evidence suggests interaction with DNA through transcriptases, increasing production of neurotransmitter by producing more synthase enzymes, for example.

Antihistamines, Antiasthmatics & Histamine Agonists

Antihistamines are compounds that block histamine from activating histamine receptors. Since histamine functions to mediate allergic response, blocking histamine at H1 receptors stops the body's characteristic responses, i.e. inflammation and vasoconstriction. H2 receptors in the stomach regulate the release of gastric acid; hence the new class of H2-blockers such as Zantac and Tagamet stop the secretion of acid by selectively blocking these receptors without affecting the H1 receptors responsible for allergic response.

Histamine is concentrated in mast cells, cells whose function is essentially to release histamine and immunoglobins when tissue damage occurs. Receptors on the cell surface trigger lysing (breaking open) of the cell, releasing these allergic mediators. Mast cells are especially numerous in parts of the body that are injured often, such as the fingers and toes, or which enjoy frequent contact with the environment, such as the mucosa of the lips, nose, etc.

Histamine is also a neurotransmitter in the CNS and a typical problem with some antihistamines is drowsiness. The effort has been to produce compounds that do not enter the brain very well.

Antihistamines fenethazine

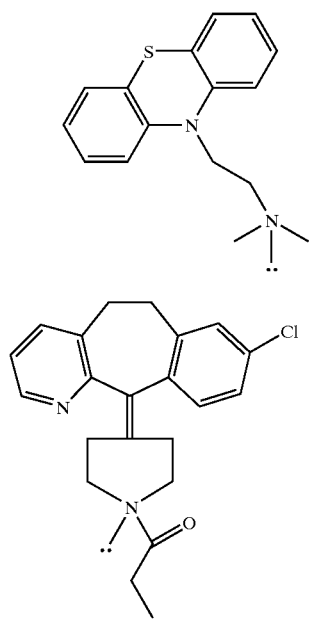

loratadine (Claritin)

cyproheptadine (Periactin)

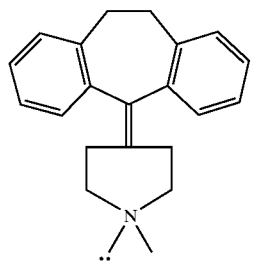

diphenhydramine (Benadryl, Nytol, Sominex)

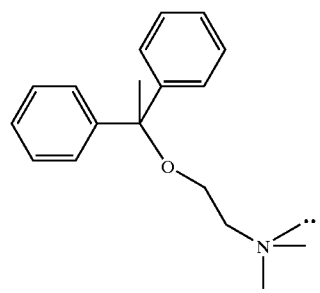

dimenhydrinate (Dramamine)

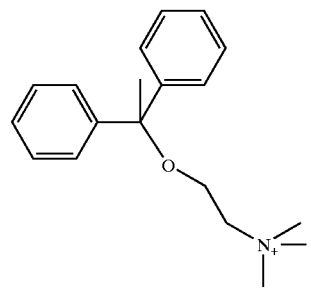

doxylamine (Unisom)

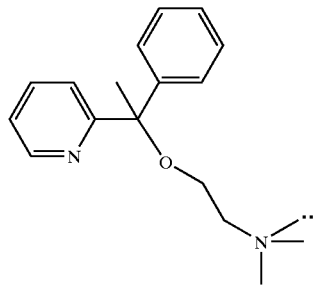

chlorpheniramine (Chlor-Trimeton)

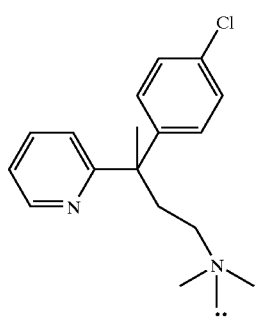

brompheniramine (Dimetapp)
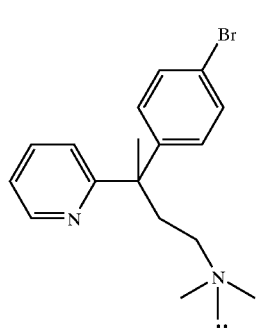
cinnarizine (Stugeron)
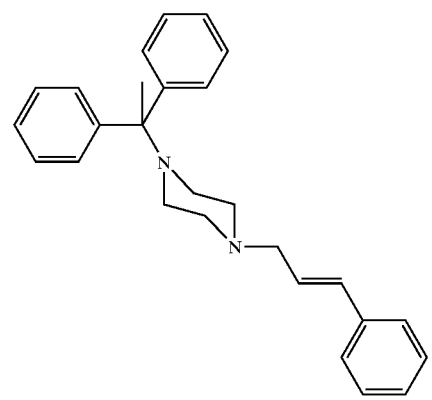
fexofenadine (Allegra)
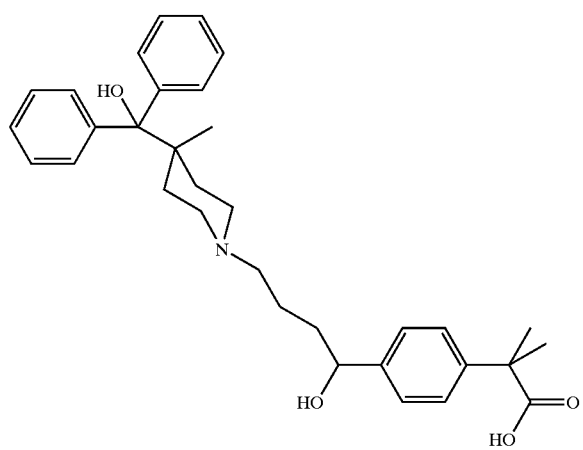
cetirizine (Zyrtec)
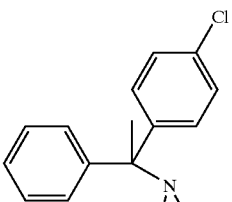
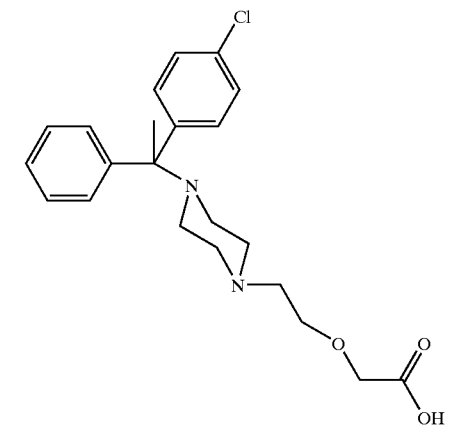
terfenadine (Seldane)
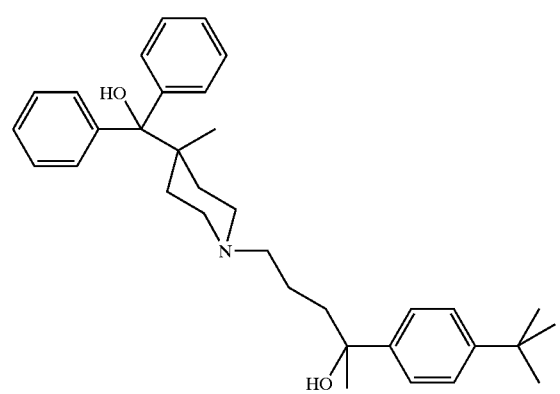
hydroxyzine (Atarax, Vistaril)
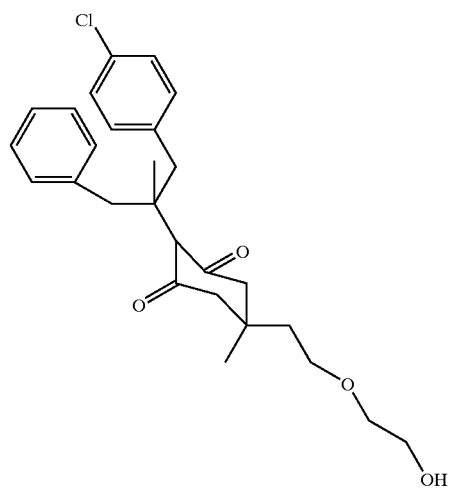

azelastine (Astelin)

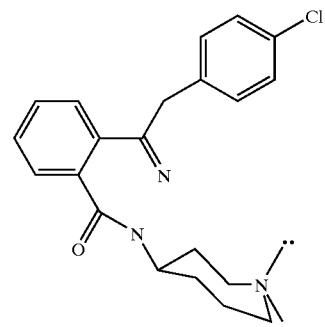

nizatidine (Axid)

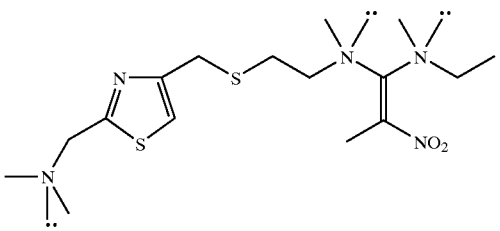

cromolyn (Nasalcrom)

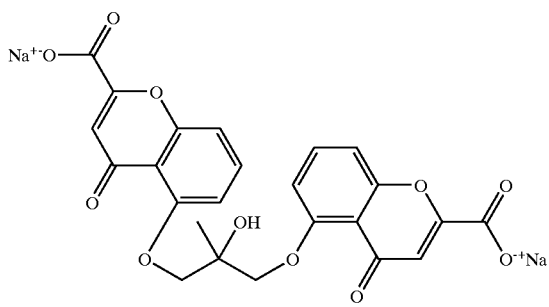

famotidine (Pepcid)

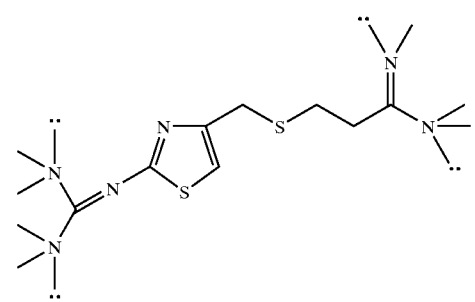

ranitidine (Zantac)

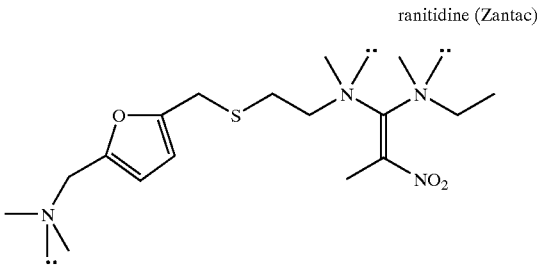

Fenethazine represents a tricyclic antihistamine very similar to Thorazine, a strong antipsychotic dopamine blocker. Cyproheptadine (Periactin), which also acts at serotonin receptors, resembles the now-popular Claritin. Periactin has been prescribed psychiatrically for anxiety. Benadryl is probably the most familiar of the class; it has strong sedating qualities. Hydroxyzine also has been prescribed as a sedative. Dimenhydrinate has been marketed as an anti-nausea medication as Dramamine. Cetirizine (Zyrtec) is a metabolic product of hydroxyzine; since hydroxyzine is available as a generic, it is cheaper than the newer drug and just as effective.

Azelastine (Astelin) has a novel structure but also acts on both H1 and H2 receptors. Cromolyn works by a distinct mechanism; it prevents release of histamine following immunoglobin binding on mast cells (prevents mast degranulation).

Histamine blocker (H2 blockers)

cimetidine (Tagamet)

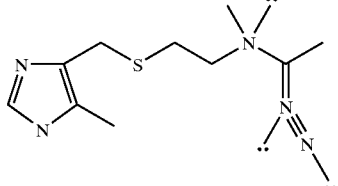

H2-selective antihistamines have become popular as treatments for excess stomach acid. These histamine blockers are very similar structurally and mechanistically. All four have about the same bioavailability, half lives, and antagonist activity.

Proton pump inhibitors omeprazole (Prilosec)

lansoprazole (Prevacid)

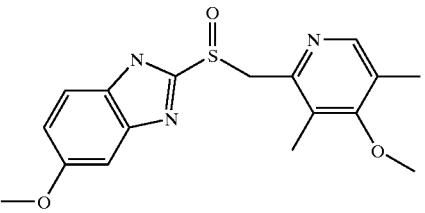

Omeprazole (Prilosec) and lansoprazole (Prevacid) belong to a class of antisecretory compounds, the substituted benzimidazoles, that do not exhibit anticholinergic or histamine H2-receptor antagonist properties, but that suppress gastric acid secretion by specific inhibition of the (H+,K+)-ATPase enzyme system at the secretory surface of the gastric parietal cell. These proton pump inhibitors have emerged as a therapeutic alternative to histamine antagonists for the treatment of gastric disorders, especially acid reflux disease ("heartburn").

Histamine agonists

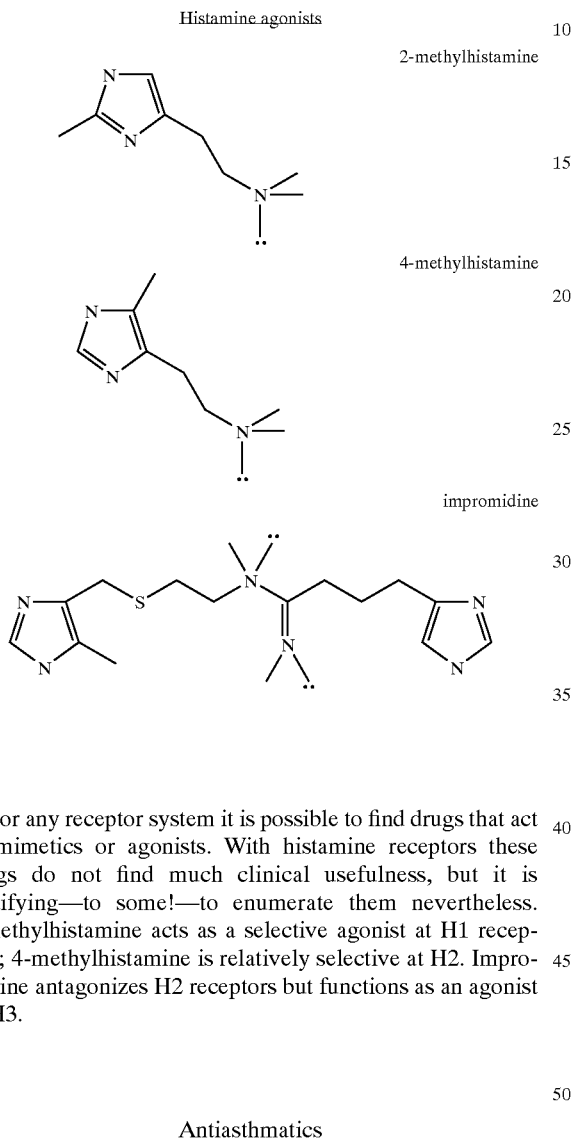

For any receptor system it is possible to find drugs that act as mimetics or agonists. With histamine receptors these drugs do not find much clinical usefulness, but it is gratifying—to some!—to enumerate them nevertheless. 2-methylhistamine acts as a selective agonist at H1 receptors; 4-methylhistamine is relatively selective at H2. Impromidine antagonizes H2 receptors but functions as an agonist at H3.

Antiasthmatics

Asthma is essentially an accentuated allergic response to the environment, i.e. an autoimmune disorder. The process of allergic response is complex, which gives one many points at which to attack the problem. First, immunoglobin and antigens bind to the surface of mast cells. Mast cells then release histamine, leukotrienes, peptides, which bind to tissue receptor sites and modify intracellular chemical processes governing various functions such as blood pressure regulation, smooth muscle tone, fluid disposition, etc. Compounds that inhibit any of these steps can be used to treat asthma and allergy, beginning with the antihistamines listed above.

methylxanthine bronchodilators

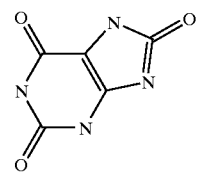
uric acid

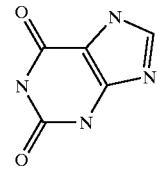
xanthine

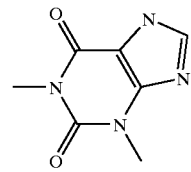
theophyline

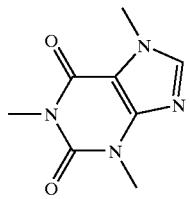
caffeine (1,3,7-trimethylxanthine)

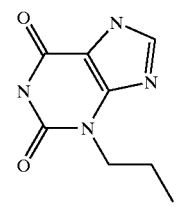
enprotyline

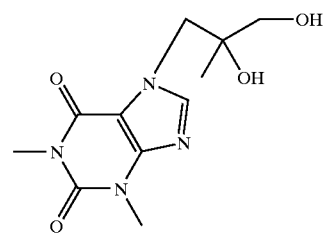
dyphyline leukotriene antagonist

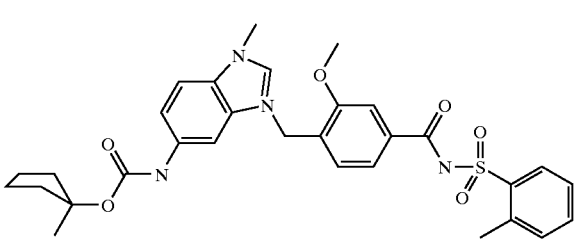
zafirlukast beta agonists albuterol (Proventil)

isoproterenol metaproterenol (Metaprel)

isoetharine (Isuprel)

terbutaline (Brethine)

Perhaps the oldest method for reducing asthma symptoms is bronchodilation by methylxanthine compounds like caffeine and theophylline. These are currently outmoded by other compounds that perform the same function more selectively like the beta2-adrenergic agonists (beta agonists). Methylxanthines act by inhibiting the enzyme which effects cAMP degradation (phosphodiesterase) and by antagonizing adenosine, which causes bronchoconstriction. The beta agonists, like metaproterenol, isoetharine, isoproterenol, terbutaline, and albuterol, mimic adrenaline at a subset of adrenaline receptor which controls the tone of smooth muscle like that of the bronchi. Another older class of drugs, antimuscarinics, exemplified by atropine, has enjoyed some historical use.

Zafirlukast (Accolate) represents a line of attack on the leukotriene compounds released along with histamine from mast cells. Leukotrienes are mediators like histamine which bind to receptors on tissue cells to signal an allergic reaction. Blocking them blocks the signal to the (bronchial) cells and thus the undesirable response.

The final mechanism one can attack is the slow inflammatory response to binding by leukotrienes and/or histamine. The body regulates inflammation with glucocorticoid steroids, and synthetic compounds such as fluticasone (Flonase) and beclomethasone (Beclonase) are effective mimetics.

Antihyperlipidemics

Antihyperlipidemics are relaively new drugs which lower blood cholesterol levels and help to prevent atherosclerosis by inhibiting the formation of plaque on arterial and vascular linings. The formation of this plaque is dependent on the proportion of various types of blood-fats, particularly on the ratio of high-density lipoproteins (HDLs) to low-density lipoproteins (LDLs). This proportion is in turn influenced by genetics and by the amount of certain substances in the diet, particularly cholesterol and saturated fat. Cholesterol is essential in the formation of VLDLs, large lipoproteins produced by the liver; on catabolysis by lipoprotein lipase, VLDLs produce the smaller LDLs, which are the so-called "bad cholesterol," HDLs being termed "good cholesterol" in the common parlance. Because the production of these lipoproteins is complex, several points can be targeted for action by various drugs.

HMG-CoA reductase inhibitors ("Satin drugs")

simvastatin (Zocor)

mevastatin (Compactin)

lovastatin (Mevacol)

pravastatin (Pravachol)

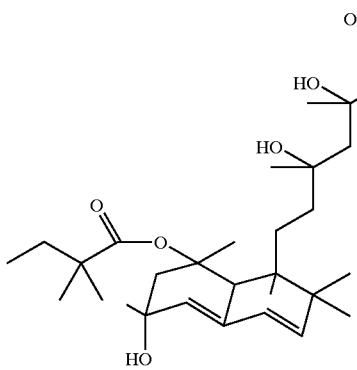

The most commonly used antihyperlipidemics are simvastatin analogs, especially simvastatin (Zocor) itself. These drugs, known as HMG-CoA reductase inhibitors, decrease production of cholesterol by inhibiting the first step in sterol synthesis which involves production of mevalonate ion from CoA-S-mevalonate. Decreased cholesterol formation results in a reduction in VLDLs and hence LDLs. Pravastatin is the active metabolite of mevastatin; lovastatin and simvastatin are inactive prodrugs that work through their hydroxyl derivatives, obtained by similar ring-opening.

These drugs also stimulate receptor-mediated clearance of LDLs. LDL receptors undergo upregulation (increase in receptor density) and VLDL catabolysis is increased.

Recent studies suggest a reduction in osteoporosis as a result of treatment with statin drugs.

Clofibrate analogs

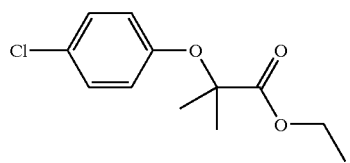

clofibrate (Atromid)

gemfibrozil (Lopid)

bezafibrate (Bezatol)

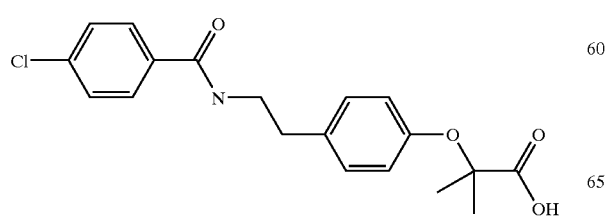

fenofibrate (Fenobrate)

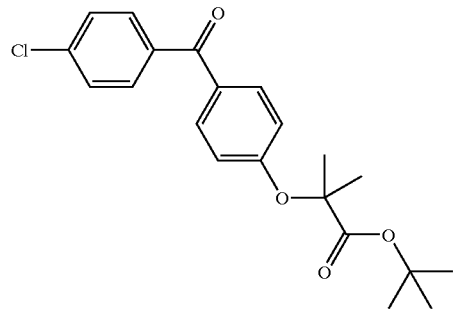

Other drugs like clofibrate and gemfibrozil increase the activity of lipoprotein lipase, reducing the level of VLDLs. This enzyme is an extracellular species present in the blood and gut. Effects on other lipase enzymes may account for the nausea common to this drug. Cholesterol production in the liver is reduced, probably as a secondary effect due to lower VLDL levels, while fecal cholesterol excretion is enhanced. Clofibrate is fairly toxic and may be carcinogenic.

Antihypertensives

The body controls blood pressure by a complex feedback mechanism between baroreceptors and effector nerves, primarily adrenergic in nature. This system is modulated by a peptide systems (angiotensin/renin).

Pharmacologic control of blood pressure acts through four basic mechanisms. Sympathoplegics reduce peripheral vascular resistance, inhibit cardiac function and increase venous pooling by a number of mechanisms involving adrenergic nerves.

Direct-acting vasodilators decrease blood pressure by increasing blood volume. Veins and arteries are forms of smooth muscle, and relaxing the muscle results in larger volume and lower pressure. Angiotensin antagonists work on peptide systems with effects on smooth muscle. Finally, diuretics decrease sodium content, decreasing blood volume and thus blood pressure. Because the body responds to exogenous agents by homeostatic regulation, concomitant use of several agents working on different mechanisms is frequently used, rather than simply increasing the dose of a single med.

Adrenoceptor drugs propranolol

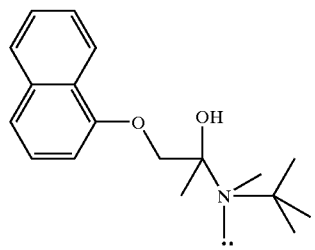

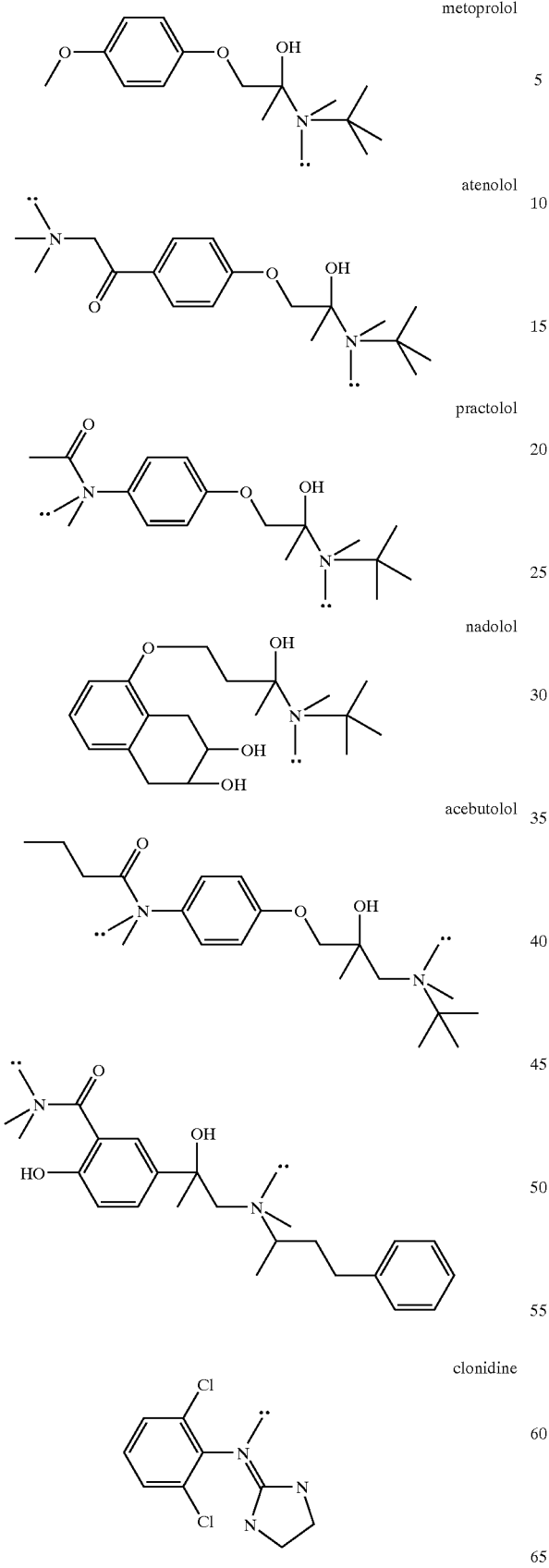
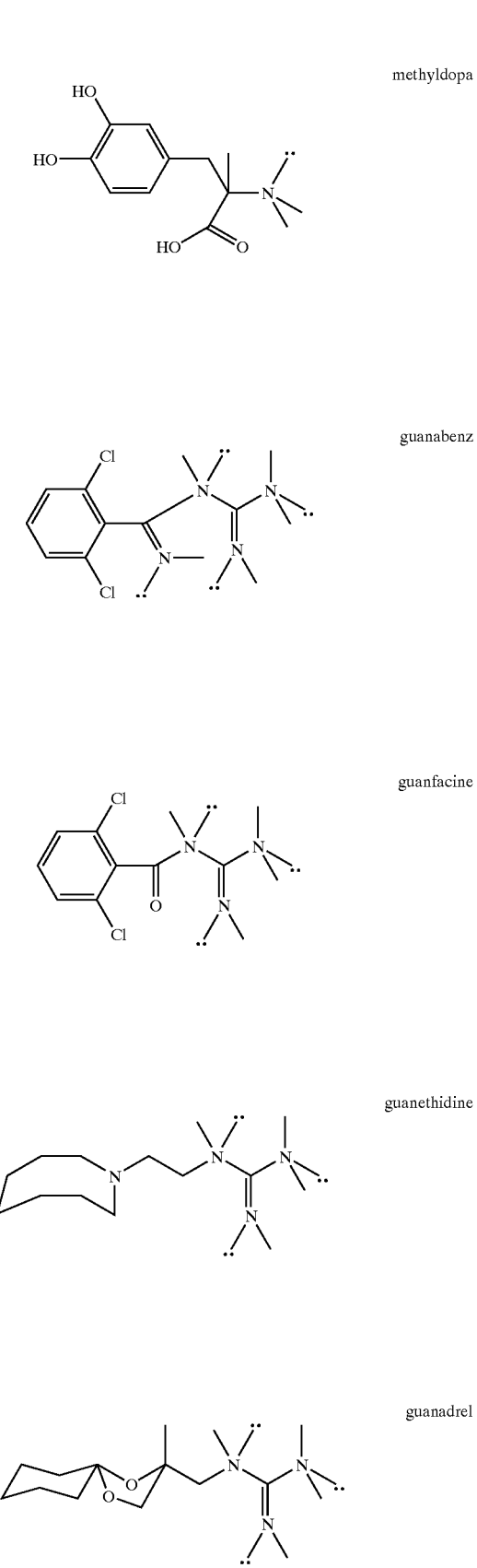

prazosin

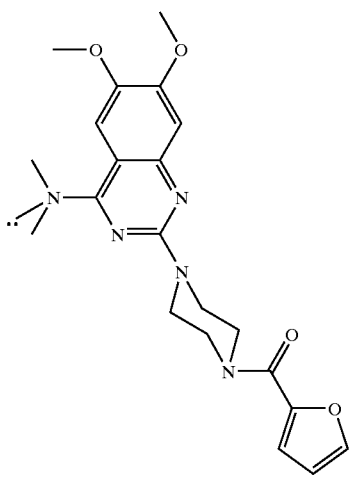

terazosin

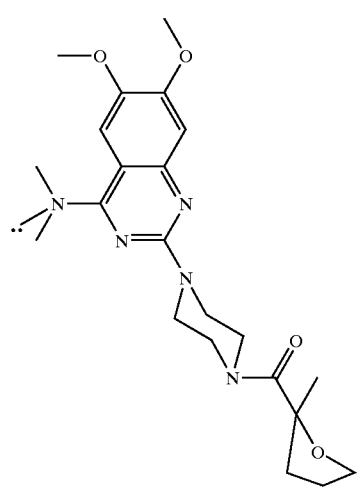

resepine

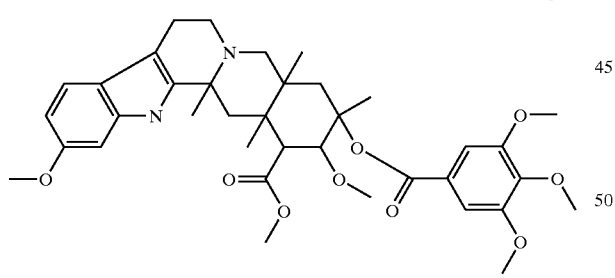

Sympathoplegics or sympatholytics antagonize the function of adrenalin compounds. Beta blockers block beta-1 receptors in hart muscle, decreasing cardiac output. The include propranolol (Inderal), metoprolol (Lopressor), labetolol (Normodyne), nadolol (Corgard), atenolol (Tenormin), and acebutolol (Sectrol). Some adrenoceptor-activating compounds have a hypotensive effect by acting centrally at alpha receptors. These include clonidine (Catapres), guanfacine (Tenex), guanabenz (Wytensin), and methyldopa. These probably work by activating presynaptic autoreceptors, decreasing norepinephrine (agonist) release.

Compounds that block alpha-1 receptors peripherally, in blood vessels, include prazosin (Minipress) and terazosin (Hytrin).

Reserpine (Serpasil) blocks amine uptake, while guanethidine (Ismelin) and guanadrel (Hylorel) block sympathetic nerve terminals.

Propranolol, which was formerly the most prescribed drug of the class, leads to accumulation of bradykinin, which contributes to the antihypertensive effect.

Cholinergic drugs mecamylamine

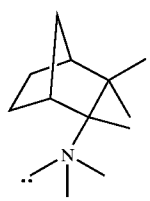

trimethamapan camsylate

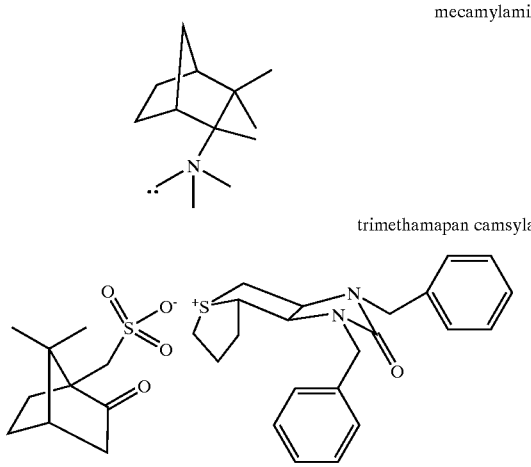

Some anticholinergic drugs (ganglion blockers) are effective as hypotensives, but they are less popular because of side effects. These include trimethapan (Arfonad) and mecamylamine (Inversine).

Direct vasodilators diazoxide (Hyperstat)

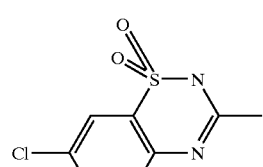

hydralazine (Apresoline)

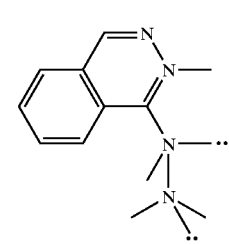

minoxidil (Loniten, Rogaine)

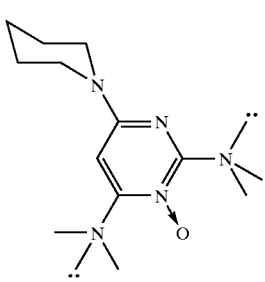

nitroprusside (Nipride)

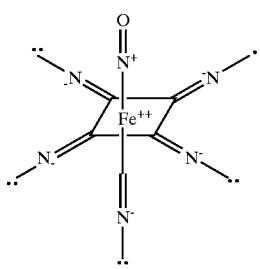

Diazoxide acts by opening potassium channels and relaxing smooth venous and arterial muscle. Despite structural similarities, it has no diuretic properties. It has a relatively long half-life of about 24 hours, and is often used parenterally (by injection) in emergencies. The drug also inhibits insulin release and is used in diabetes. Minoxidil is mainly used orally, also opening potassium channels.

Hydralazine and minoxidil dilate arterioles but not veins. Nitroprusside (as the sodium salt) dilates both, by a mechanism involving activation of guanylyl cyclase, resulting in formation of cGMP and relaxation of smooth muscle.

Calcium channel blockers

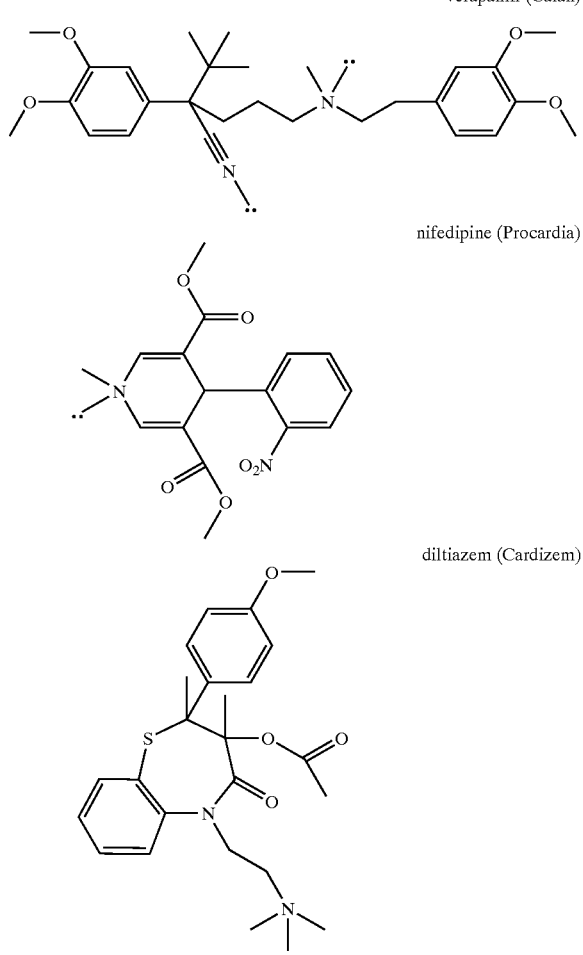

verapamil (Calan)

nifedipine (Procardia)

diltiazem (Cardizem)

The calcium channel blockers are a popular means to control hypertension. Smooth muscle contraction depends on calcium influx to control muscle tone. The reaction path is complex, involving the peptides calmodulin and myosin light chain kinase (MLCK). When the latter enzyme is activated it phosphorylates myosin which acts with actin to contract muscle. Blocking the channel statistically prevents calcium ion influx and decreases tension in blood vessel smooth muscle. Skeletal muscles rely on intracellular calcium ion, and are not affected by these drugs. Cardiac muscle is highly dependent on calcium channel action.

Calcium channels also exist at presynaptic nerve terminals in adrenergic neurons. These are voltage-dependent ion channels embedded in nerve membranes at the ends of adrenergic neurons. When a voltage pulse arrives at the end of a neuron (propagated by sequential firing of sodium channels), the calcium channels detect the change in voltage and allow influx of $Ca^{++}$ ions. This triggers binding of vesicles and release of vesicular adrenalin, noradrenalin or dopamine, along with cotransmitters such as peptides, ATP, etc. One of the acid tests as to whether a substance is a neurotransmitter is whether its release is calcium-dependent.

Verapamil is the oldest and prototypical calcium channel blocker. It is highly bound to blood plasma proteins and suffers about an 80% hepatic first-pass elimination on oral administration. This means that most of the drug absorbed through the intestine is removed by the kidney before reaching the target tissues (heart and major blood vessels). Nifedipine is significantly less active at cardiac sites than diltiazem or verapamil, and is also highly plasma-bound. Diltiazem is much less plasma bound. Despite plasma binding, all three drugs have fairly short half-lives (3–6 hours).

Ion channel blockers generally act by lodging in an open channel and blocking it. Similarities in ion channels mean that some sodium channel blockade occurs with calcium channel blockers. This is more of a problem with verapamil than the other drugs. In addition to treatment of hypertension, these drugs are used to treat angina, migraine, and atherosclerosis.

Diuretics benzthiazide (Diuril)

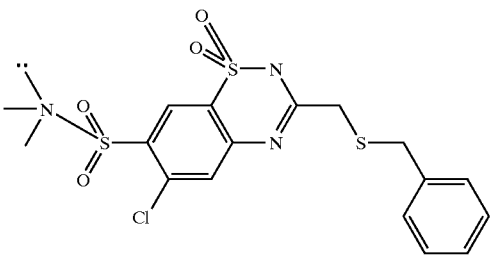

Diuretics reduce blood volume by causing excretion of water through the kidney. This reduces blood pressure very effectively. The drugs used for this purpose are typically thiazides; a main problem is potassium depletion. Potassium-sparing diuretics have also been developed.

Angiotensin antagonists & ACE inhibitors saralasin sar-arg-val-tyr-val-his-pro-ala

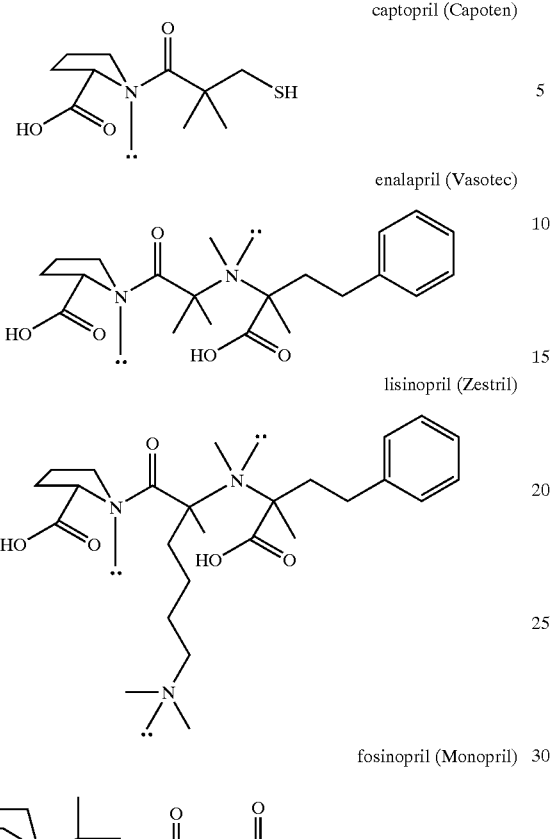

captopril (Capoten)

enalapril (Vasotec)

lisinopril (Zestril)

fosinopril (Monopril)

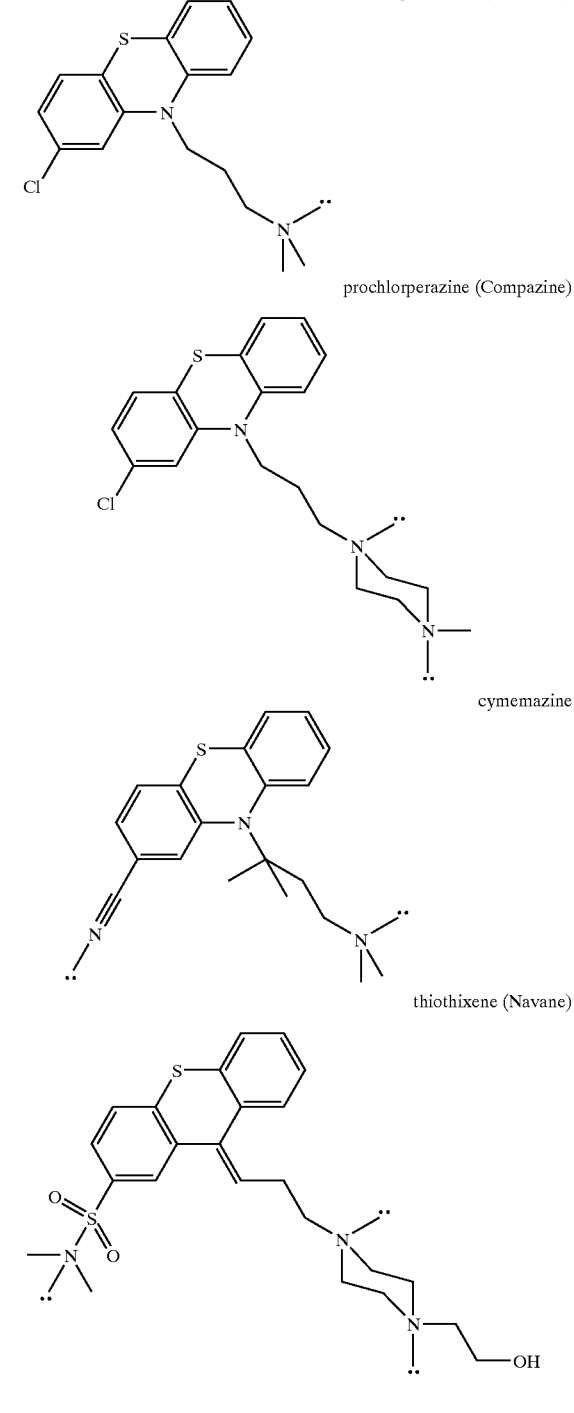

Thorazine analogs chlorpromazine (Thorazine)

prochlorperazine (Compazine)

cymemazine thiothixene (Navane)

Recent studies have shown the ACE inhibitors to be extremely safe drugs. ACE is an enzyme which converts angiotensin I to angiotensin II, the active form. Angiotensin receptors modulate the tension of smooth muscle, including venous and arterial tissue. Inhibiting the enzyme decreases the amount of active peptide extant in body tissues.

Antipsychotics, Lithium, Mood Stabilizers & Dopamine Agonists

Antipsychotics are used to calm mania or racing thoughts, to control aggression, or to block spurious thoughts in schizophrenia, including auditory hallucination (hearing voices). They exert their tranquilizing effects by blocking the excitatory neurotransmitter dopamine at post-synaptic terminals. Dopamine neurons are abundant in the limbic system and its projections into the cerebrum, especially the originating in the substantia nigra. Blocking of adrenergic, histaminic and serotonergic receptors also contribute to the CNS effects of these drugs.

Although they are potent psychotropics, these drugs are not commonly abused, since they inhibit the brain's pleasure pathways which emanate from the limbic system into the frontal lobe.

Tricyclic compounds like Thorazine, known as phenothiazines, are the oldest compounds, and are the least selective, blocking several subtypes of dopamine receptors. Thorazine was discovered by accident while seeking better antihistaminic agents. It has shown efficacy in blocking the effects of LSD, confirming the dopamine agonist activity of that drug.

Haloperidol analogs
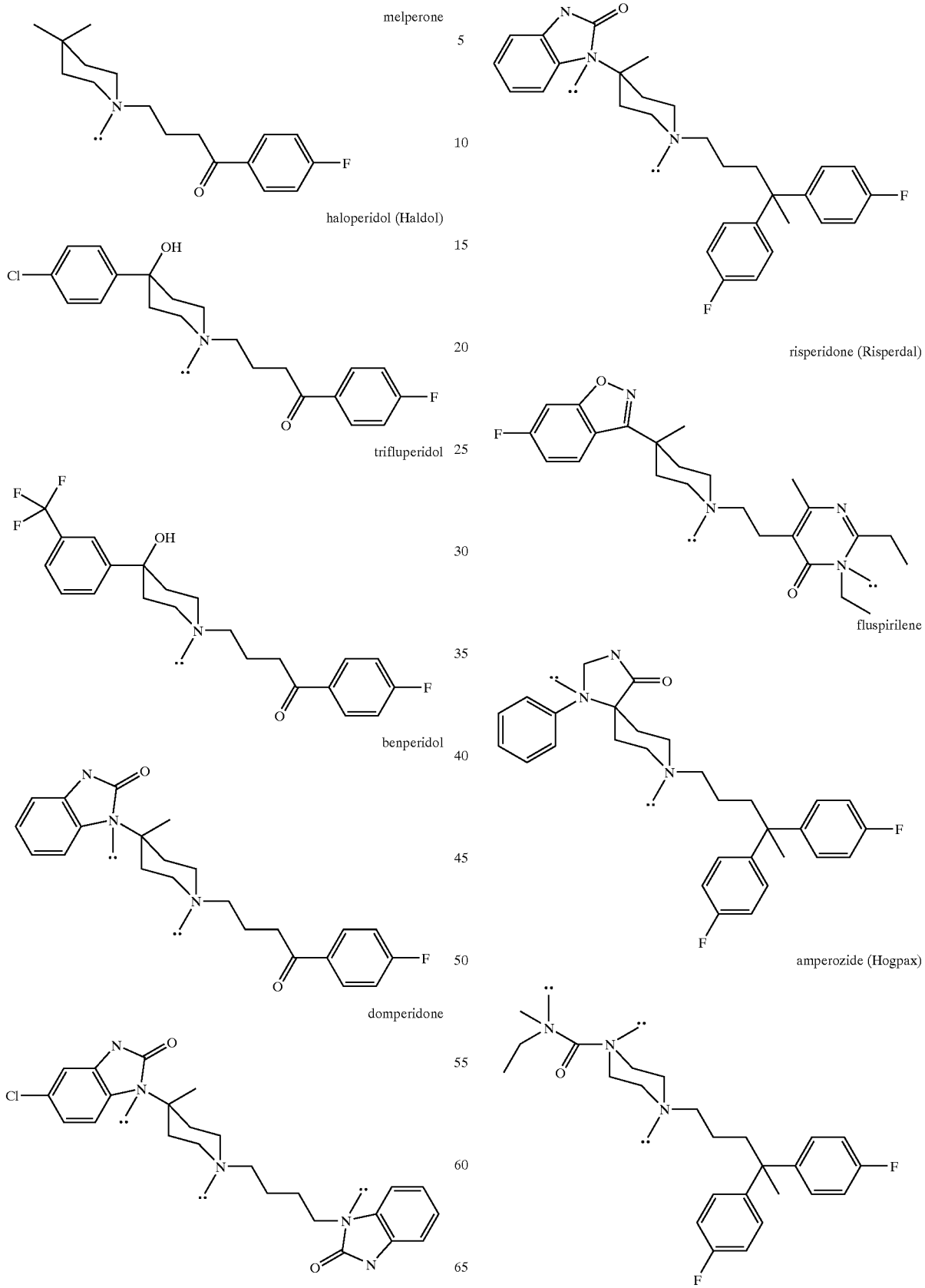

Newer compounds of the haloperidol class (bytyrophenones), first synthesized in the late 1950s, are more selective for D2 subreceptors.

Sulpiride analogs clebopride sulpiride amisulpiride sultopride

Clebopride and sulpiride analogs represent another structural class of antipsychotics with similar actions. The binding profile of all these groups (indeed, of each compound) will be slightly different.

Clozapine analogs & novel neuroleptics clozapine loxapine clothiapine olanzapine (Zyprexa)

quetiapine (Seroquel)

butaclamol tetrabenazine

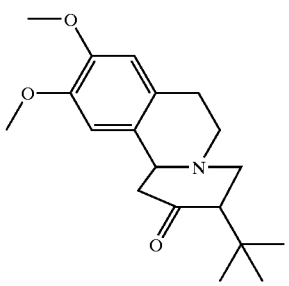

The clozapine analogs represent another structure type with a different neurological profile. They are not as selective for D2 as the haldol class, but may be more effective at controlling some types of psychosis. These drugs show significant 5-HT2 receptor blockade and may be more selective for limbic dopamine systems (as opposed to those involved in motor control), reducing the extrapyramidal syndrome (EPS) and dyskinesias common to antipsychotic meds. The newer agents, such as Zyprexa and Seroquel, seem not to impart the agranulocytosis common with clozapine.

Clozapine is extensively metabolized and some of its metabolites show anti-AIDS activity.

Other novel structural classes which function as neuroleptics are represented by butaclamol (a pentacyclic) and tetrabenazine. The latter is a dopamine depleter, a drug which can chemically induce depression.

Mood stabilizers baclofen

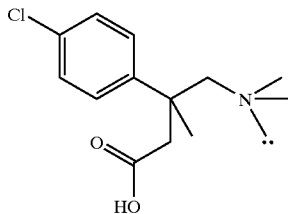

gabapentine (Neurontin)

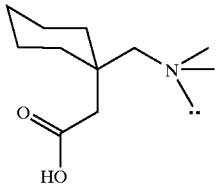

vigabatrin

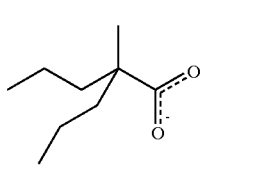

valproic acid (Depakote)

tigabine (Gabitril)

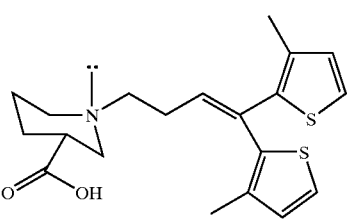

lamotrigine (Lamictal)

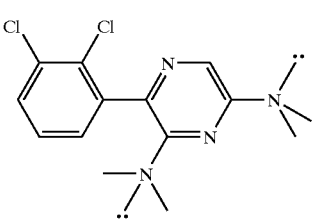

phenytoin (Dilantin)

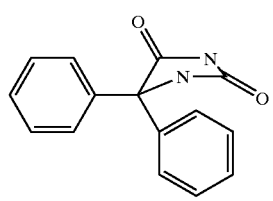

carbamazepine (Tegretol)

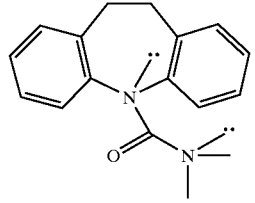

topiramate (Topamax)

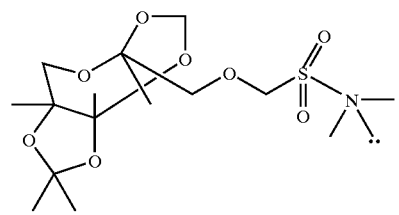

clonidine

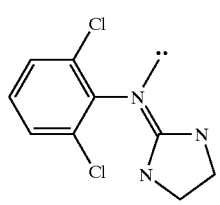

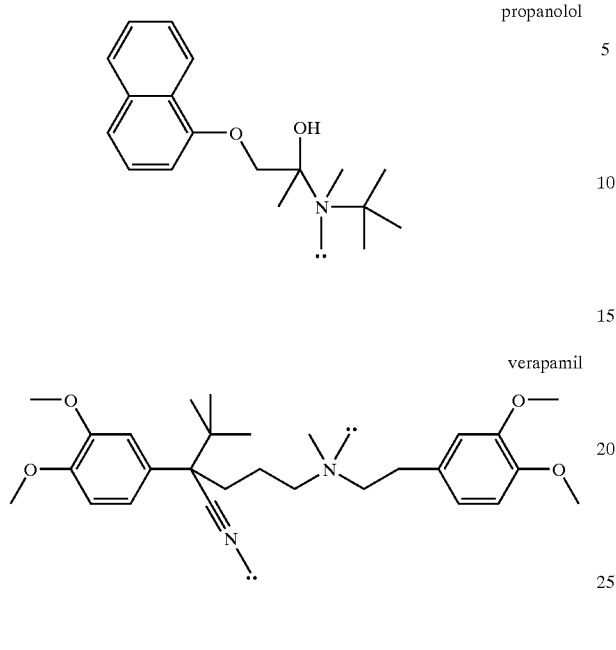

propanolol verapamil

The use of anticonvulsant medications for psychotropic purposes has recently grown, primarily to prophylact against manic and/or panic syndromes. Phenytoin and carbamazepine probably work by affecting ion-gating systems (particularly sodium channels) in excitable membranes. Phenytoin structurally resembles the barbiturates while carbamazepine has a tricyclic structure like the tricyclic antidepressants.

Gabapentine and valproic acid probably work on GABA systems. The latter inhibits the enzyme responsible for degrading GABA at high concentrations, but probably works by other mechanisms at lower, therapeutic levels. Lamotrigine is another antiepileptic used as a mood stabilizer. It reduces release of glutamate, an excitatory amino acid. Topamax, a fructose derivative, enhances GABA systems while blocking glutamate.

Propanolol is a beta-adrenergic blocker prescribed for performance phobia or stage fright. Clonidine is an alpha agonist sometimes used to calm peripheral tremor as in alcohol withdrawal. Verapamil, a calcium-channel blocker, is also used for this purpose.

Dopamine agonists apormorphine

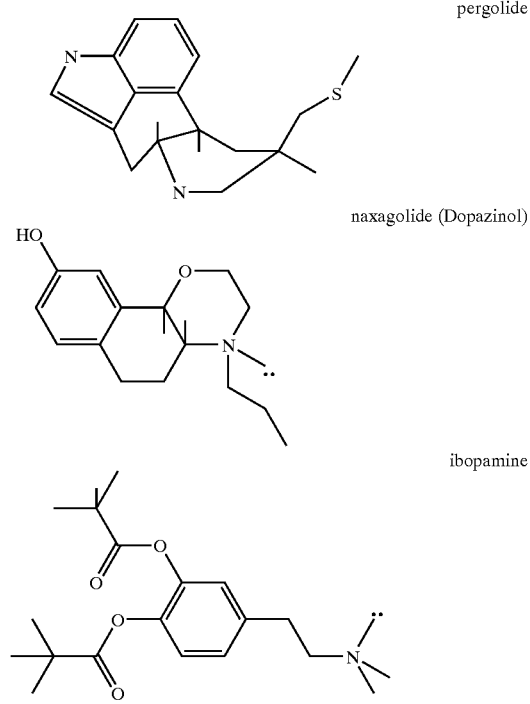

pergolide naxagolide (Dopazinol)

ibopamine

Pergolide and naxagolide are dopamine agonists employed against Parkinsonism, which results from decreasing dopamine function in the CNS with aging. Apomorphine is a selective D2 agonist, while ibopamine serves agonist function at both dopamine and adrenergic receptors.

Cholinergic Drugs

Acetylcholine neurons convey sensory information to the brain and control muscular tension, including peristalsis and motor control. Cholinergic neurons are dominant in inhibitory activity inherent to so-called parasympathetic neurons which complement dopamine/norepinephrine based neurons in parallel sympathtic structures. Two cholinergic receptor subtypes have been identified by selective agonists: nicotinic and muscarinic. At least two subtypes of muscarinic receptors (M1 and M2) have been identified.

In addition to direct agonists, selective antagonists, enzyme inhibitors, and antidotes to enzyme inhibitors have been developed. Cholinoceptors also serve as heteroreceptors, presynaptically governing the release of norepinephrine and other neurotransmitters.

Cholinoceptor agonists

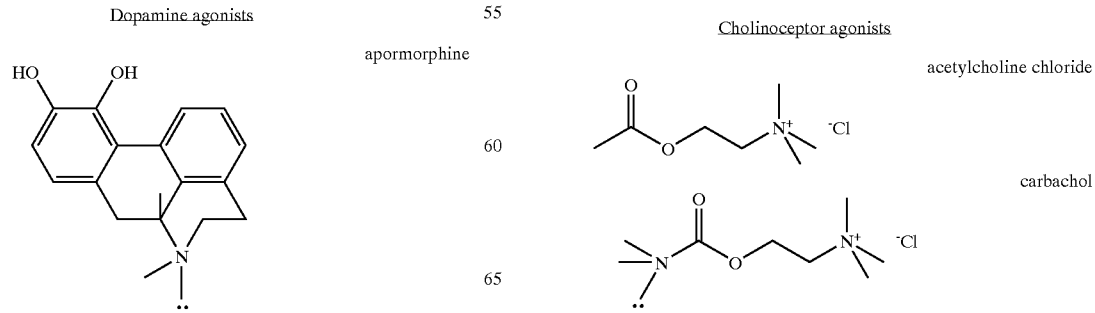

acetylcholine chloride carbachol

-continued

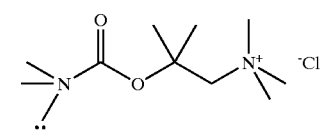
bethanechol

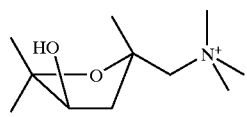
muscarine

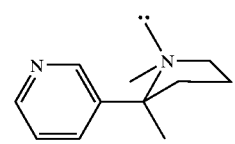
nicotine

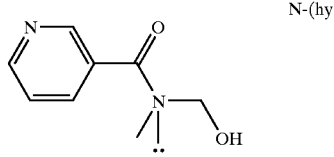
N-(hydroxymethyl)-nicotinamide

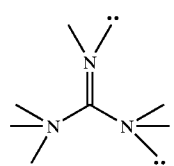
guanidine

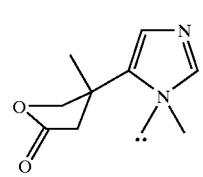
pilocarpine

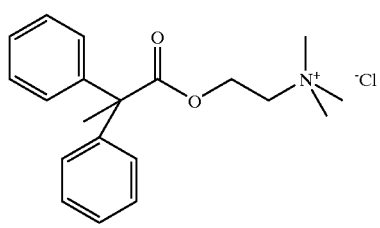
lachesine

Nicotine is a selective agonist at nicotinic receptors: it defines this subset of cholinergic receptors. Muscarine defines the other subset, with further distinctions of M1 and M2 (at least) existing. Muscarine is produced in trace amounts in the fly agaric mushroom. Other species of fungus produce greater amounts. Fly agaric also contains muscarinic antagonists (atropine) and GABA agonists (muscimol). Atropine used to be applied as an antidote to poisoning by muscarine in this fungus, before the role of muscimol was elucidated.

The N-hydroxymethyl amide of nicotinic acid is also active as an agonist at nicotinic cholinoceptors. Carbachol is used opthalmically as a miotic, i.e. to dilate the pupils. It is also used in large animals, mainly in atonic conditions of the gut, since its formal positive charge prevents it from entering the brain and limits its absorption in the gut. In addition to receptor action, it probably promotes acetylcholine release. Lachesine is a selective muscarinic agonist.

Guanidine exists as the guanidium ion at physiologic pH; it is used as a pro-cholinergic, antiviral, antifungal, antipyretic and muscle stimulant. Bethanechol activates M1 and M2 subreceptors, releases IP3 (inositol triphosphate), and activates guanylyl cyclase. Again, as a quaternary, positively charged species, it is used mainly to mimic acetylcholine in the gut. It is sometimes given to relieve the antimuscarinic constipation caused by tricyclic antidepressants or other meds. Pilocarpine is a cholinomimetic which also increases gastric acid secretion.

GABA Drugs

GABA (gamma-aminobutyric acid) is the most important inhibitory neurotransmitter in the CNS. By gating negative chloride (Cl−) ions into the interior of nerve cells, GABA inhibits the presynaptic release of neurotransmitter due to a positive voltage polarization pulse. Such inhibition is extremely common: GABA receptors can be found at 60–80% of CNS neurons.

Subtypes of GABA receptors can be activated by the mushroom toxin muscimol (at the A subtype) as well as the antispasmodic amino acid baclofen (B subtype). These drugs directly mimic the action of GABA at the receptor.

Allosteric facilitation of GABA receptors occurs at several distinct sites; the compounds which bind there are used as sedatives and anxiolytics. These compounds bend the receptor open to indirectly facilitate GABA binding.

GABA agonists/facilitators

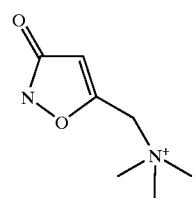
muscimol

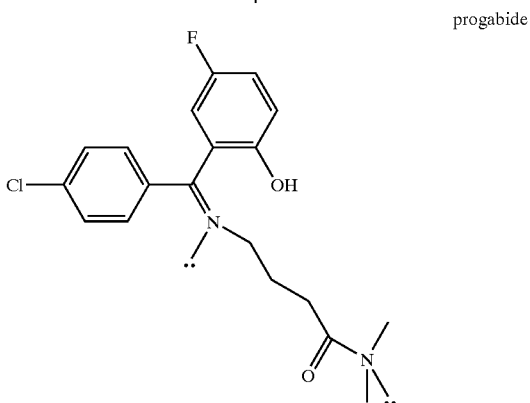
progabide

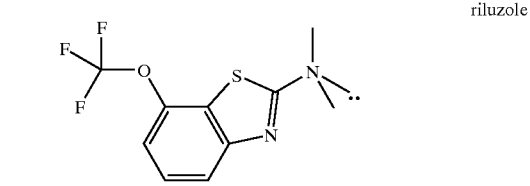
riluzole baclofen
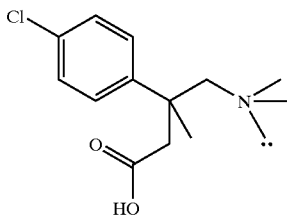

phenytoin (Dilantin)
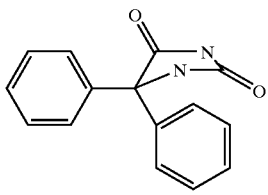

gabapentine (Neurontin)
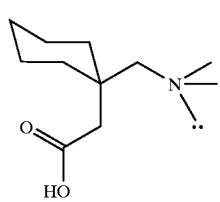

carbamazepine (Tegretol)
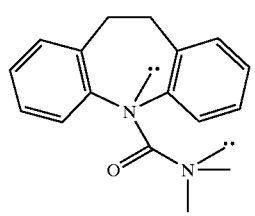

vigabatrin
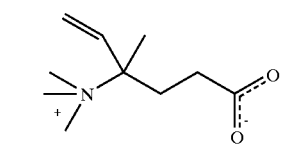

topiramate (Topamax)
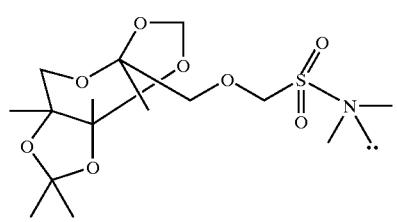

valproic acid (Depakote)
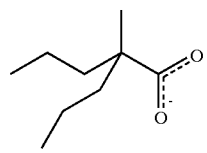

tigabine (Gabitril)
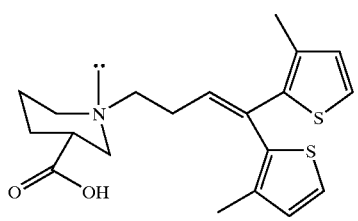

lamotrigine (Lamictal)
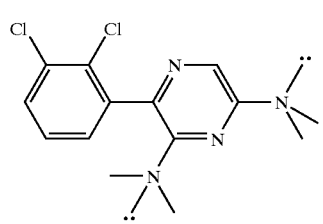

Progabide is a pro-drug which decomposes to GABA in the CNS. It crosses the blood-brain barrier, which GABA itself, being a zwitterion (doubly-ionized amino acid), does not. Vigabatrin (gamma-vinyl-GABA) inhibits GABA-aminotransferase (GABA-T), the enzyme responsible for degrading GABA in the synapse. It thus prolongs the sojourn of GABA molecules and promotes binding in this way.

Depakote (valproic acid) seems to act on nerve membranes to reduce susceptibility to seizure. At high doses it acts like vigabatrin to inhibit GABA-T. Gabapentine is another recently marketed antiepileptic (Neurontin) that is also finding psychiatric application as a mood stabilizer. The neurological rationale for this application is that panic attacks (or mania in bipolar disorder) resemble epilepsy in that they are characterized by a pre-panic "kindling" phenomenon, characterized by repetitive neural firings, leading to a critical stage. Gabapentine may encourage production of or discourage degradation of GABA. Lamotrigine probably works by reducing release of glutamate, an excitatory neurotransmitter usually governed by the inhibitory GABA.

Novel GABA drugs represent one of the most active areas of psychotropic research. Riluzole, for instance, is a GABA uptake inhibitor with anticonvulsant and hypnotic properties; it also blocks sodium channels and inhibits glutamate release.

Opiate Narcotics

Opiates, derived from the poppy plant, contain alkaloids which activate the brain's endogenous endorphin receptors to produce analgesia, euphoria, and respiratory suppression. Poppy opiates possess a polycyclic phenanthrene nucleus with various substituents that determine the fit into the receptor. Although morphinelike compounds have been found in mammalian brain tissue, it is generally agreed that the enkephalins and endorphins represent the endogenous compounds which poppy constituents mimic.

Opiate receptors of several varieties are responsible for the major pharmacologic effects. These subtypes are given Greek names like mu (analgesia, euphoria), sigma (dysphoria, cardiac stimulation), kappa (sedation, spinal cord analgesia, miosis), delta, etc. Antitussive properties, emesis (vomiting), and anticholinergic (constipation) effects also occur, indicating a wide variety of receptor types and actions. The sigma receptor is now surmised to be related to glutamate function.

Opiate receptors exert effects on synaptic transmission by presynaptically modulating the release of neurotransmitters, including acetylcholine, norepinephrine, dopamine, serotonin, and substance P. The latter compound is a peptide neurotransmitter involved in nociceptive (pain-related) neurons. Opiate receptors act on G-peptides, transmembranal macromolecules linked to post-synaptic intracellular enzymes (such as adenylyl cyclase) or ion channels (such as $K^+$, $Ca^{++}$). In high doses the opiates cause generalized CNS depression sufficient for surgical anesthesia.

Phenathrenes morphine

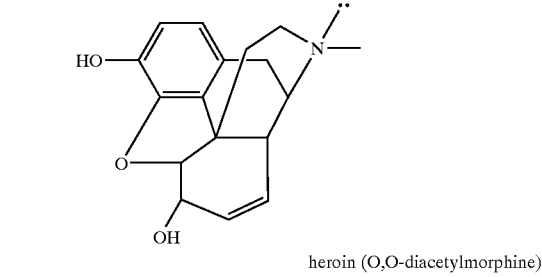

heroin (O,O-diacetylmorphine)

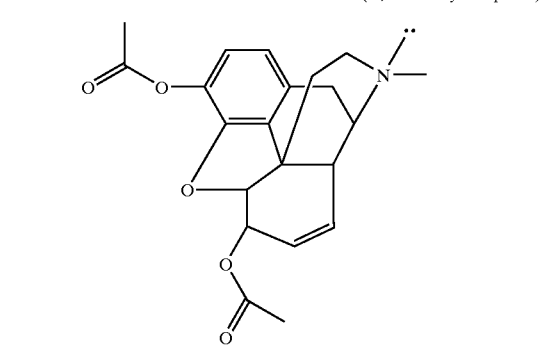

hydromorphone (Dilaudid)

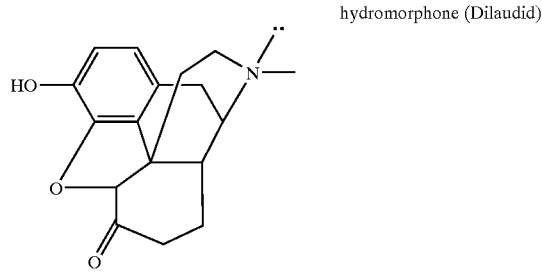

oxymorphone (Numorphan)

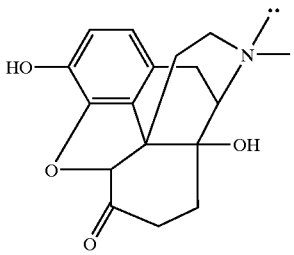

codeine (Tylenol 3,4)

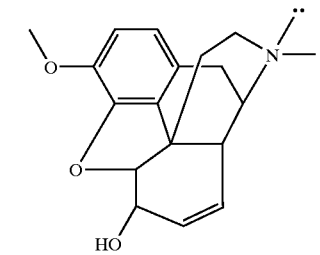

hydrocodone (Vicodin, Lorocet)

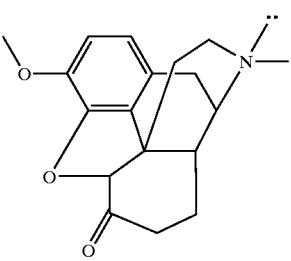

oxycodone (Percocet, Tylox)

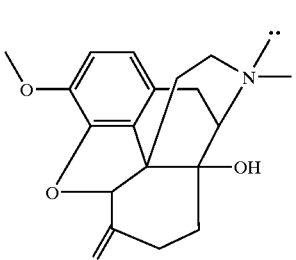

etorphine (Immobilon)

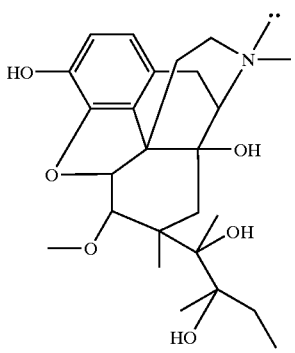

Phenylheptylamines
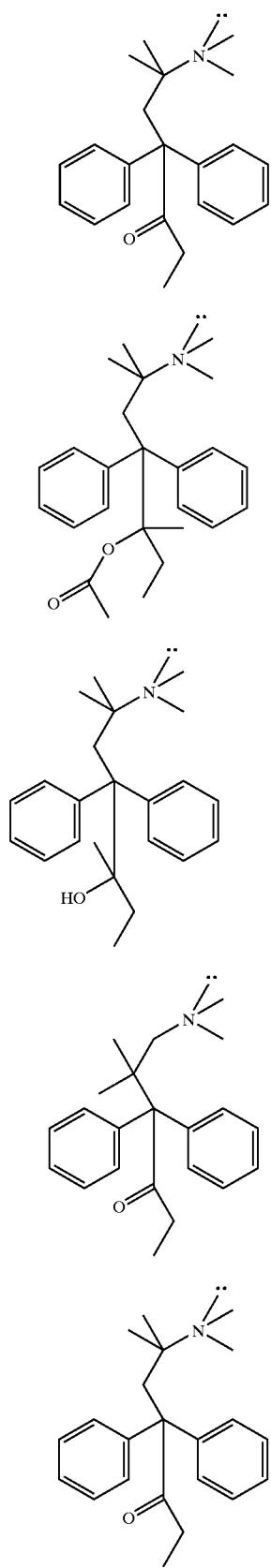
methadone
methadyl acetate
dimeheptanol (methadol)
isomethadone
dipipanone
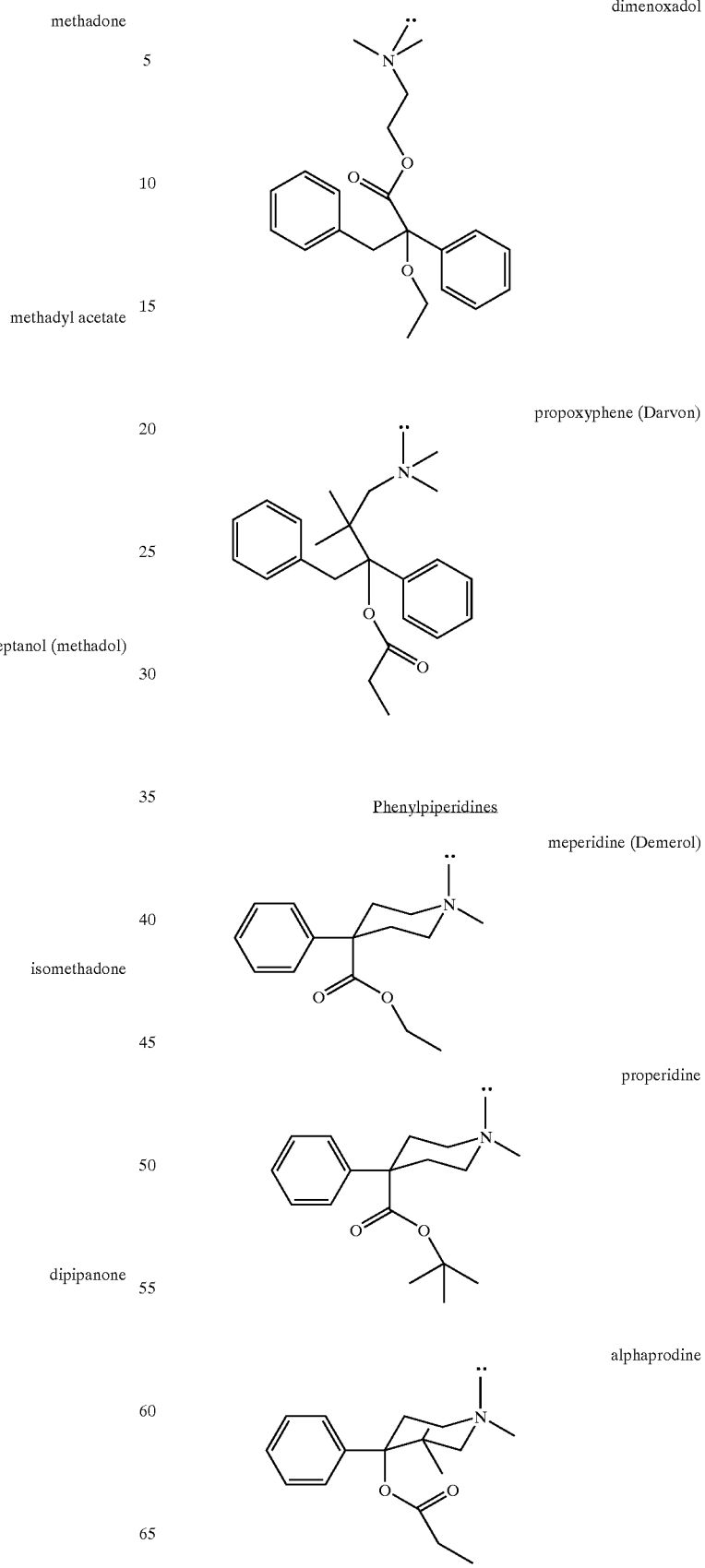
dimenoxadol
propoxyphene (Darvon)
Phenylpiperidines
meperidine (Demerol)
properidine
alphaprodine

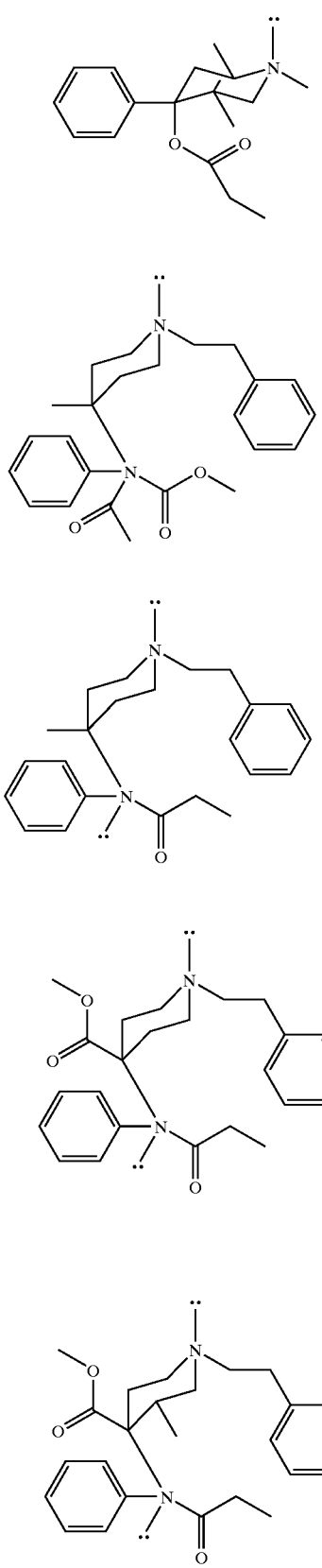

beta-promedol alfentanyl (Alfenta)

fentanyl (Sublimaze)

carfentanyl lofentanil

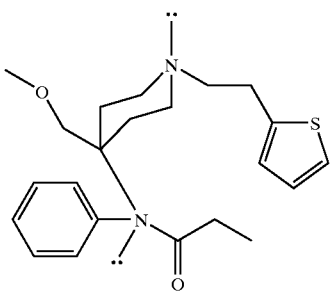

sufentanil (Sufenta)

Codeine is a mild analgesic which retains agonist activity at other receptor subtypes including those controlling respiration, peristalsis and euphoria. Morphine is among the most potent of the phenanthrene class. The less amphoteric heroin crosses the blood-brain barrier more readily but decomposes into morphine once there. Oxycodone, the main active constituent in Percodan and Percocet, is somewhat less potent.

Meperidine (Demerol) is a synthetic drug that has approximately the same analgesic activity as morphine. Methadone, invented by the Nazis and originally named dolophine, is famous for its use in assuaging the heroin withdrawal syndrome. Its half-life is substantially greater than that of heroin, and while it is bound to receptors it blocks newly administered heroin. Its analgesic activity is also approximately equal to morphine's, but it imparts less euphoria.

Fentanyl constitutes one of the most potent synthetics, propoxyphene (Darvon) one of the least. Methoxy compounds such as codeine and oxycodone are less susceptible to first-pass reactions (typically conjugation to a glucuronide) and therefore have a higher oral-to-parenteral ratio. Less-amphoteric compounds (compounds with more definite acid or base properties) pass the blood-brain barrier more easily.

Partial agonist-antagonists noscapine

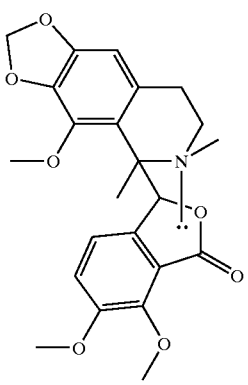

pentazocine (Talwin)

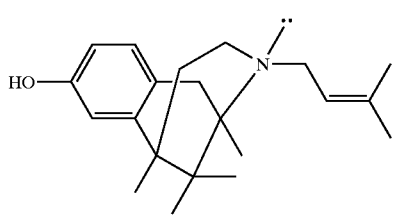

butorphanol (Stadol)

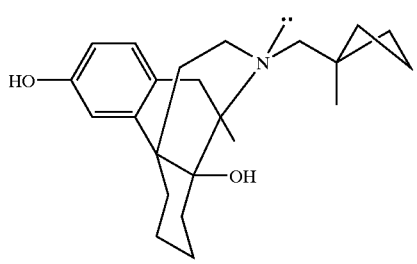

nalbuphine (Nubain)

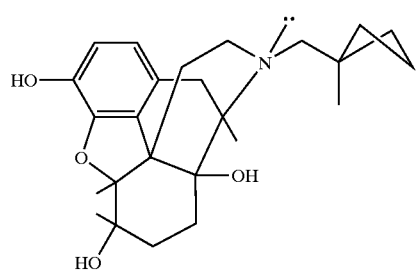

Alteration of the phenanthrene skeleton produces drugs with mixed agonist/antagonist properties at opiopeptin sub-receptors. These drugs are being used variously as pain killers, aids in withdrawal from heroin and even alcohol addiction, and (illegally) to increase athletic stamina. Stadol has been used nasally to relieve migraines. Although mixed agonists retain analgesic properties, they often impart dysphoric effects.

Narcotic antagonists naloxone

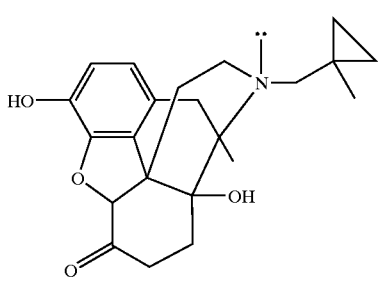

nalorphine (Nalline)

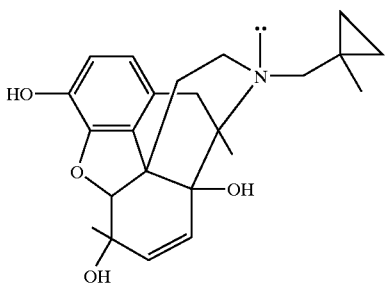

naltrexone (ReVia)

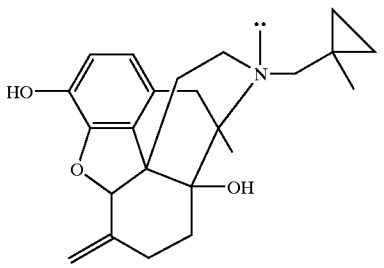

nalmefene nadide (Enzopride)

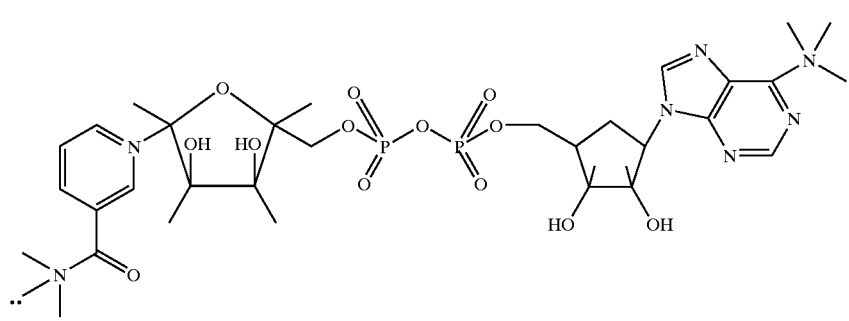

Narcotic antagonists are especially useful in cases of overdose, where they can reverse the CNS depression caused by opiate agonists. Naloxone is the most often used, most effective, and prototypal narcotic antagonist. Naloxone, nalmefene, and nadide are among several other compounds used to antagonize morphine receptors.

Naltrexone has recetnly been used to reduce the craving for alcohol among recovering alcoholics and heroin addicts (as ReVia).

Nootropics & Smart Drugs

Nootropics, also known as smart drugs or cognition activators, are drugs that enhance mental function. Several mechanisms that affect nerve function may be attacked. Compounds that are used by the body to manufacture neurotransmitters constitute one group (precursors). Reuptake and degradation inhibitors form another. Mimetics of excitatory neurotransmitters and antagonists of inhibitory ones can both stimulate neural function. Antianoxics enhance the ability of neurons to burn glucose. Phospholipid compounds affect the fatty excitable membranes of nerve cells, which are responsible for transporting a depolarization pulse down dendrites and axons. Steroid compounds also affect membrane chemistry. Vasodilators which act in the CNS increase blood supply to brain cells. Still other drugs increase the flexibility of red blood cells so they can gain access to more neurons more often. All these effects be theoretically be used to enhance neurological function in the CNS.

Precursors & mimetics

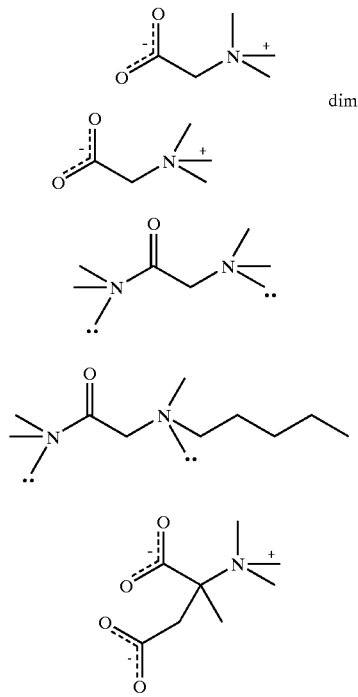

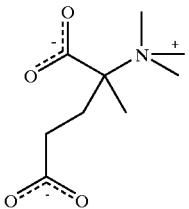
glutamate

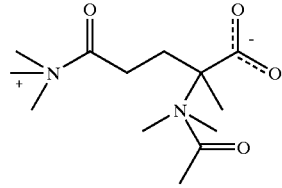
aceglutamide

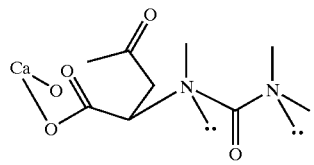
calcium-N-carbamoylaspartate

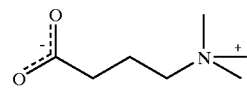
GABA

carnitine

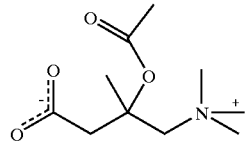
acetyl-L-carnitine (ALC)

Glycine systems perform inhibitory functions in the CNS. Enhancement of these pathways imparts antianxiety effects and so stabilizes mood. Glycine itself is a zwitterion and so does not pass the blood-brain barrier very well. Dimethylglycine is stabilized by the methyl groups; its greater lipophilicity results in better transport to the CNS, where it is converted to glycine. Milacemide is a pro compound which decomposes (via MAO-B) to glycinamide and then glycine in the CNS.

Glutamate and aspartate are another group of excitatory neurotransmitter prominent in the CNS. Since they are acidic amino acids they have difficulty crossing the blood-brain barrier, but standard tricks can be used to deliver them to the CNS. Making an amide out of a carboxy acid is one of these (as in glutamine and aceglutamide); a somewhat more radical method is to make a covalent salt with calcium, as in calcium-N-carbamoylaspartate.

Carnitine is a catabolic (tearing-down) amino acid which serves as a neuroprotectant at NMDA receptors (a subset of glutamate/aspartate receptors). Acetylation of the hydroxy group gives ALC, which again has the effect of promoting transport into the CNS.

Steroids

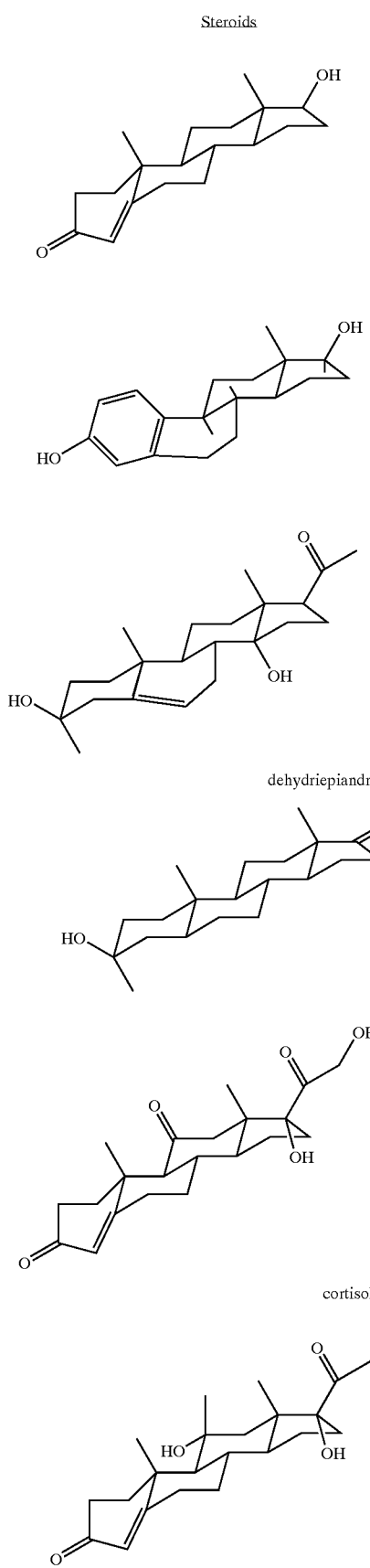

testosterone estradiol pregnenolone dehydriepiandrosterone (DHEA)

cortisone cortisol (hydrocortisone)

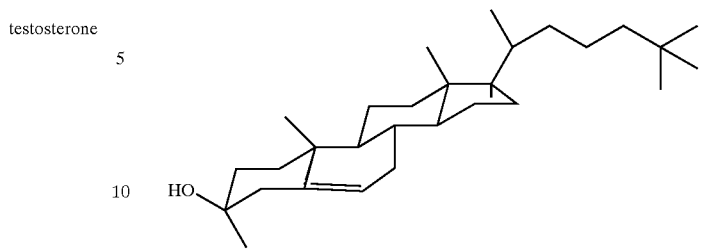

cholesterol

Several steroids have been used to bolster mental function and libido. Both testosterone and estrogens have been administered historically to increase vitality and sexual drive as people grow older (replacement therapy). Precursors to estrogen and androgen steroids such as DHEA and pregnenolone have recently been marketed as nutrients. These steroids do not have significant estrogenic or androgenic properties until converted by the body to active forms. As with all precursors, one trusts the body's homeostatic mechanisms to regulate formation of active molecules by rate-limiting steps, competitive mechanisms, and tachyphylaxis (tolerance).

Mood stabilizers

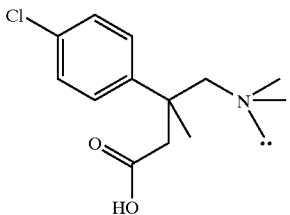

baclofen

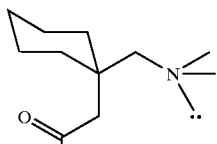

gabapentine (Neurontin)

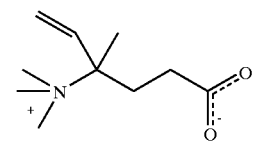

vigabatrin

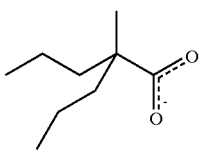

valproic acid (Depakote)

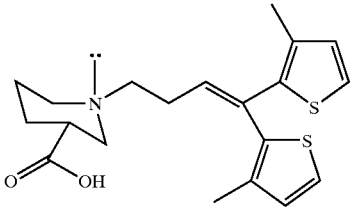

tigabine (Gabitril)

lamotrigine (Lamictal)

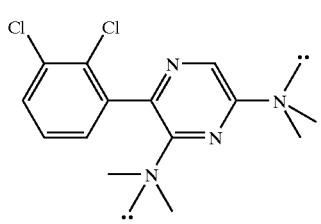

phenytoin (Dilantin)

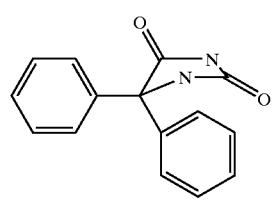

carbamazepine (Tegretol)

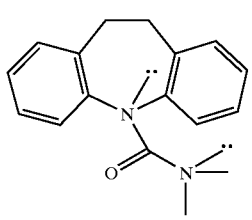

topiramate (Topamax)

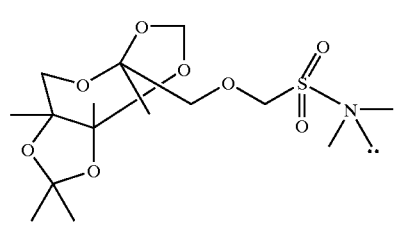

clonidine

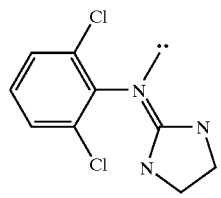

propanolol

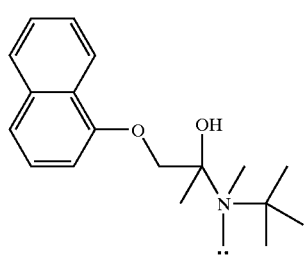

verapamil

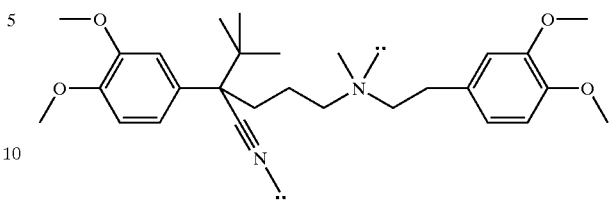

The use of anticonvulsant medications for psychotropic purposes has recently grown, primarily to prophylact against manic and/or panic syndromes. Phenytoin and carbamazepine probably work by affecting ion-gating systems in excitable membranes. Phenytoin structurally resembles the barbiturates while carbamazepine has a tricyclic structure like the tricyclic antidepressants. Propanolol, a beta-blocker, has been used to calm peripheral reactions to stress, such as stage fright.

Propanolol is a beta-adrenergic blocker prescribed for performance phobia or stage fright. Clonidine is an alpha agonist sometimes used to calm peripheral tremor as in alcohol withdrawal. Verapamil, a calcium-channel blocker, is also used for this purpose.

Antianoxics glutamic acid

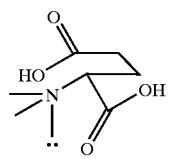

pyroglutamate

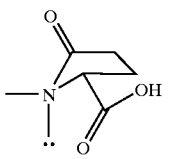

piracetam

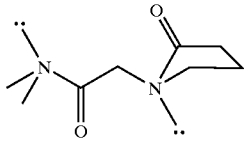

oxiracetam

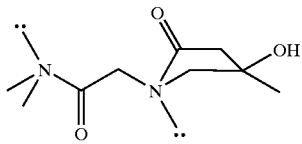

aniracetarm

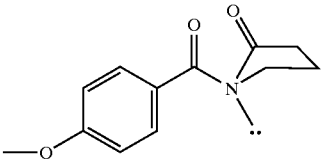

pramiracetam

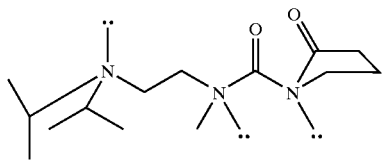

The piracetam group of antianoxic compounds work by several mechanisms to invigorate neural function. By supplying glutamic acid analogs to the Krebs cycle they enhance glucose utilization in aerobic respiration, the major means by which animal cells extract chemical energy from sugars via ATP formation. This in turn raises phospholipid cAMP levels, enhancing the function of dopamine and acetylcholine neurons. Additionally they function as anti-oxidants (compare the structure to that of vitamin C) and retard lipofuscin formation. Experimentally, piracetam has been shown to increase athletic performance, to reverse alcohol-induces brain degeneration, and has been tried as a treatment for dyslexia.

Cererbral vasodilators & anticoagulants caffeine (1,3,7-trimethylxanthine)

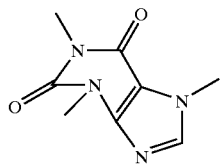

pentoxyfylline

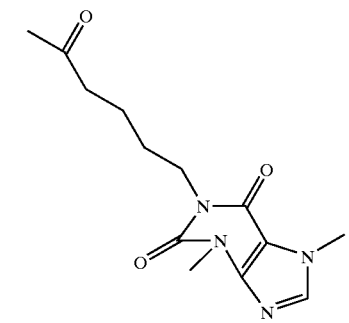

propentofylline

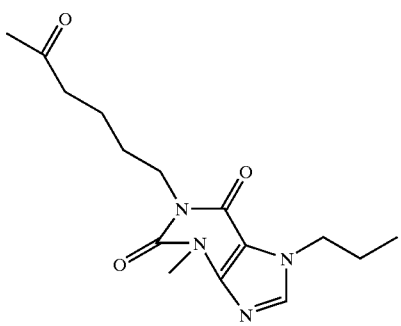

uric acid

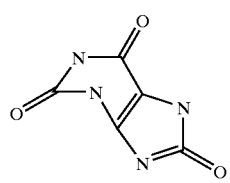

nizofenone

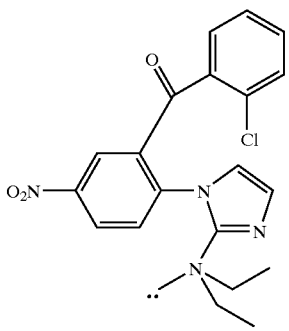

nimodipine

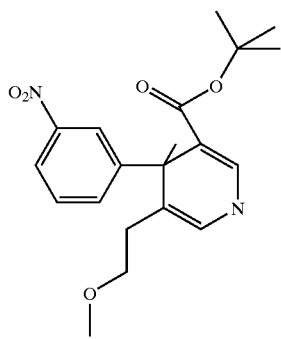

vinpocetine

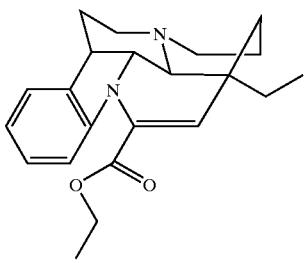

vincamine

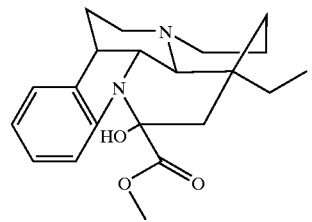

idebenone

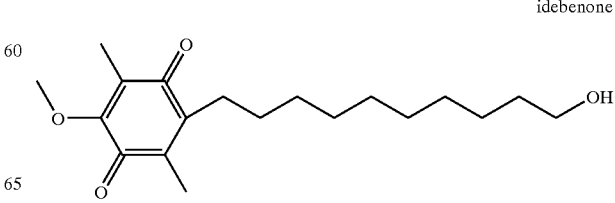

pyritinol

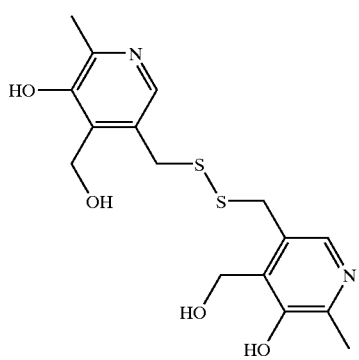

methyl salicylate

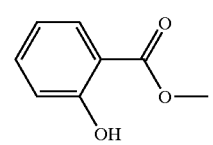

ibuprofen (Advil, Motrin)

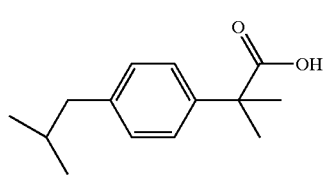

Methylxanthines are used as bronchodilators in the treatment of asthma (typically theophylline) and in conjunction with analgesics to treat headache. Pentoxyfylline and propentofylline have central and peripheral vasodilatory properties. Increased blood supply to brain tissue probably accounts for whatever nootropic properties they have. Pentoxfylline also increases the elasticity of red blood cells, enabling them to better squeeze through constricted capillaries. Such drugs are called anti-ischemics, ischemia referring to a lack of blood supply to a tissue.

Pyritinol is another vasodilator which has been used against dementia senilis (senility). Idebenone resembles ubiquinone, a compound which catalyzes mitochondrial metabolic processes. It promotes secretion of nerve growth factor (NGF) and may also protect cell membranes against lipid peroxidation. Ergocryptine is an ergot alkaloid which has been used to combat age-related memory loss and Alzheimer's. It dilates blood vessels by blocking alpha-adrenoceptors. It has been used in accident victims to increase blood flow to the brain following trauma to prevent tissue damage by anoxia. Vinpocetine and vincamine are two alkaloids from the vinca plant which also have anticoagulant and vasodilation effects.

ketoprofen (Actron)

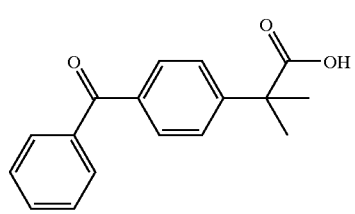

naproxen (Aleve, Naprosyn)

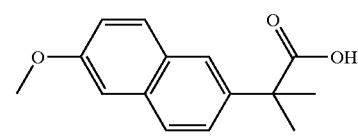

nabumetone (Relafen)

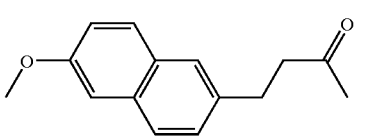

oxaprozin (Daypro)

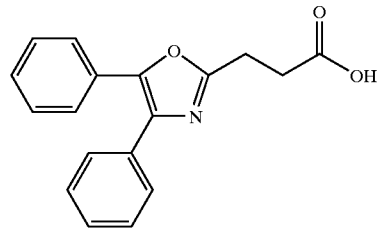

Non-steroidal Anti-inflammatory Drugs (NSAIDs)

Nonsteroidal anti-inflammatory drugs (NSAIDs) are the drugs of choice for mild to moderate pain and to reduce fever (antipyretics). They interfere with the formation of prostaglandins by inhibiting the enzyme cyclooxygenase, which closes a bond on arachidonic acid, an essential oil. The cyclical prostaglandin compounds are potent, short-lived mediators of the inflammation response. They are not stored in cells but are synthesized as needed in response to injury or irritation. Interfering with their production peripherally turns off the inflammation response in the body.

Aspirin and the other NSAIDs may also act at a site in the CNS. Some of the NSAIDs (e.g. ketoprofen) inhibit other enzymes such as lipoxygenase, further retarding the allergic/inflammation response.

penicillamine

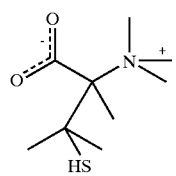

Aspirin (acetylsalicylic acid) has been used for centuries along with its relative, methylsalicylate. The latter, known as oil of wintergreen and often used topically, is even more toxic than aspirin in overdose. Aspirin interferes with platelet aggregation and retards coagulation of blood. This property probably accounts for its use in the long-term prevention of heart attacks.

In recent years drugs like ibuprofen and ketoprofen have become available over-the-counter. The more lipophilic of these drugs, such as naproxen (Aleve, Naprosyn), ketoprofen (Actron) and nabumetone (Relafen), have longer half-lives, requiring less frequent dosing, but are probably no more effective analgesics than ibuprofen. Liver, kidney and GI problems, of varying seriousness commensurate with dosage history, are common. Penicillamine has been used as a long-acting NSAID, but it is fairly toxic, causing reduction aspirin (acetylsalicylic acid)

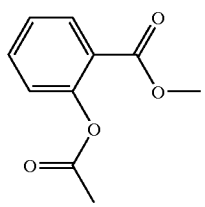

of healing and a host of autoimmmune and histological disorders.

Cyclooxygenase inhibitors celecoxib (Celebrex)

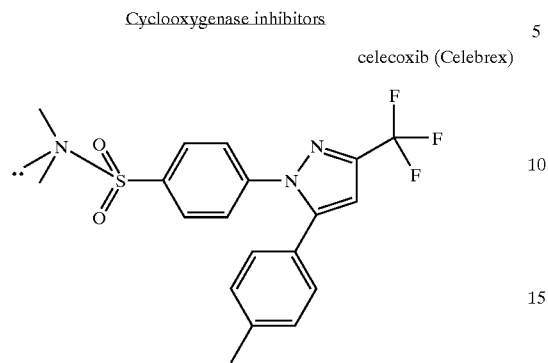

rofecoxib (Vioxx)

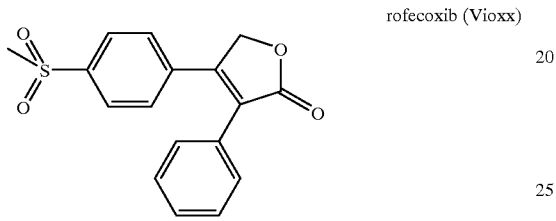

A new class of NSAIDs inhibit cyclooxygenase-2, an enzyme responsible for interconversion of prostaglandins. These COX-2 inhibitors are intended to preserve the formation of cytoprotective prostaglandins while targeting inhibition of the compounds responsible for pain and inflammation, reducing stomach irritation, Celebrex (celecoxib) is one such drug. Vioxx is another new drug in this class.

Non-narcotic analgesics phenacetin

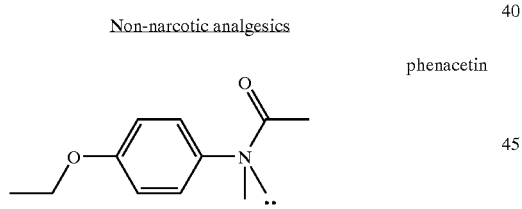

butacetin

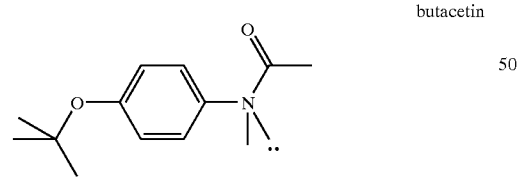

acetaminophen

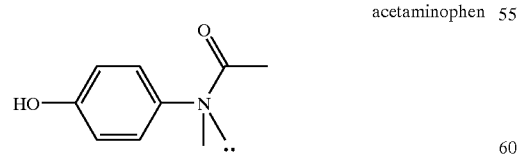

acetamidoquinone

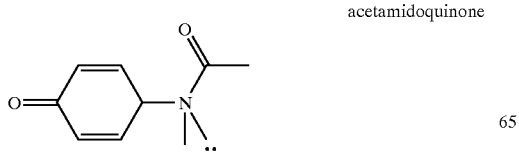

nefopam

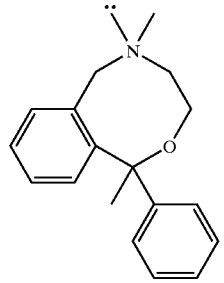

Glucosamine and chondroitin glucose

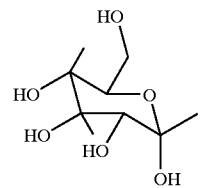

glucosamine

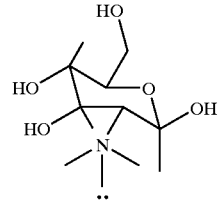

chodroitin

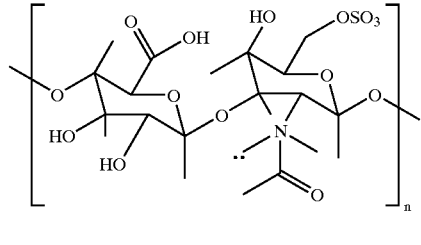

Recent studies have suggested that a pair of aminated sugar compounds can assist in repairing damage to cartilage in osteoarthritis. Glucosamine, a monomer, and chondroitin, a polymer, are being marketed as nutrients for this purpose. In cartilage, sugar polymers form a flexible connecting matrix around the tough protein strands in cartilage (a composite material).

Sedatives & alcohol Benzodiazepines diazepam (Valium)

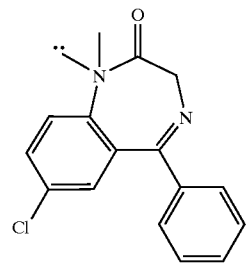

lorazepam (Ativan)

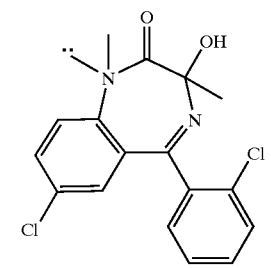

clonazepam (Klonopin)

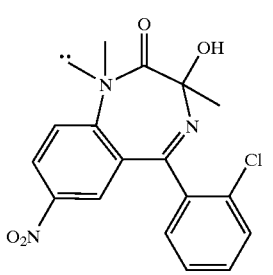

oxazepam (Serax)

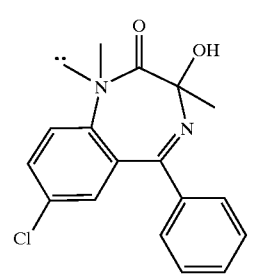

ternazepam (Restoril)

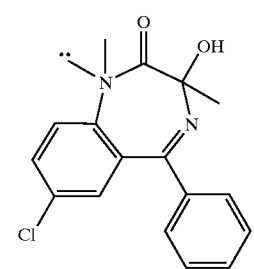

alprazolam (Xanax)

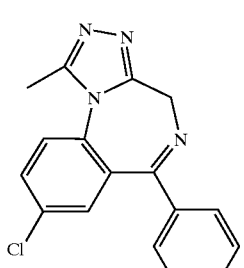

triazolam (Halcion)

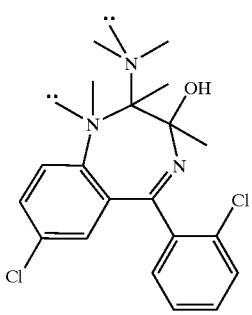

chlordiazepoxide (Librium)

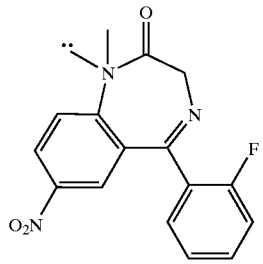

flunitrazepam (Rohypnol)

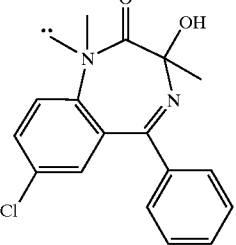

The benzodiazepine sedatives include Valium, Librium, Halcion, Xanax, Ativan, Serax, and Klonopin, to name just a few. In addition to potential effects on lipophosphate nerve membranes, these drugs work by allosterically enhancing the effect of the inhibitory neurotransmitter GABA at post-synaptic receptors. That is, they "bend" the receptor slightly so that GABA molecules attach to and activate their receptors more effectively and more often. Their chief advantage over the barbiturates, such as seconal, nembutal and phenobarbital, is that they do not act directly to open chloride ion channels.

Serotonin Drugs

Serotonin is an inhibitory neurotransmitter which complements excitatory sympathetic systems like adrenaline and dopamine in the CNS. Like the "fight or flight" adrenaline compounds, serotonin is released not only at specific synaptic sites, but also in a broadcast manner into brain tissue from sets of "diffuse" neurons emanating from the emotional centers in the limbic system into the frontal lobe. This diffuse release sets the biochemical tone of large areas of neural functioning, controlling mood and motivation. Serotonin's inhibitory action is however more complex and selective than that of GABA sedatives like Valium or Xanax, which act more globally. Because of their effects on mood, serotonin-active drugs are used as antidepressants and anxiolytics (anti-anxiety) drugs.

Serotonin antagonists

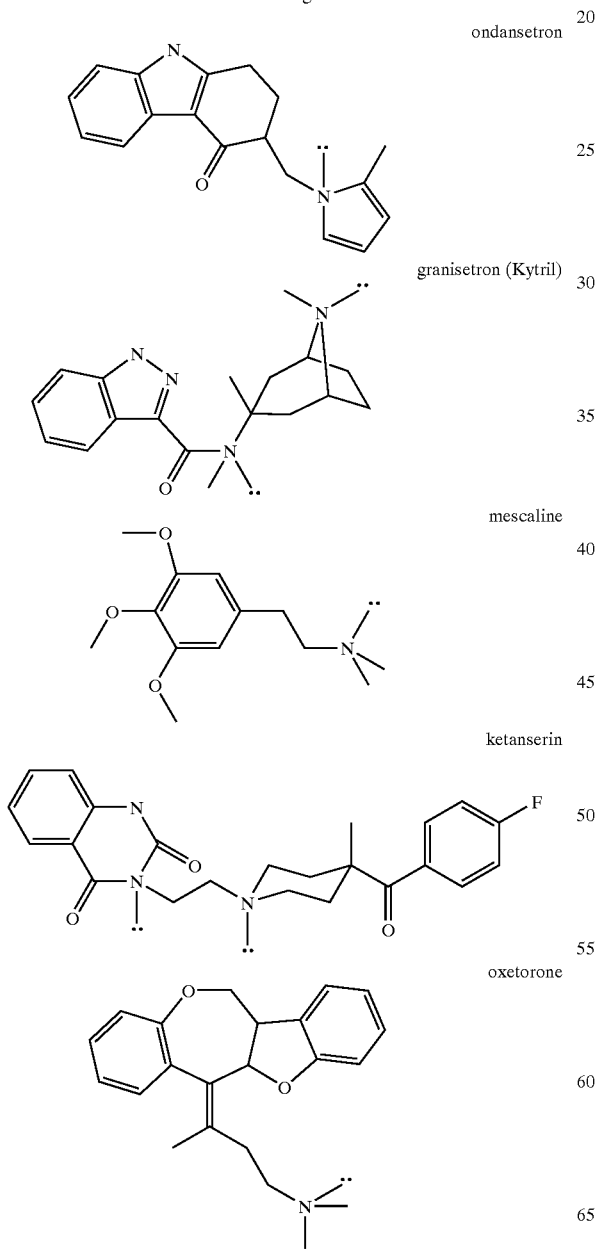

ondansetron granisetron (Kytril)

mescaline ketanserin oxetorone

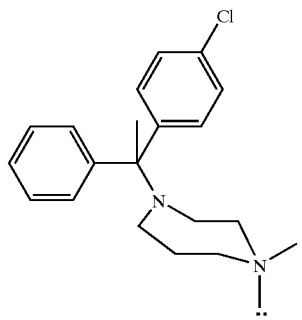

homochlorcyclizine

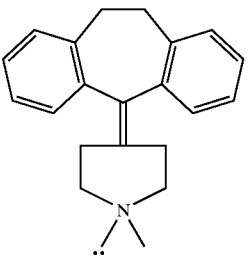

cyproheptadiene (Periactin)

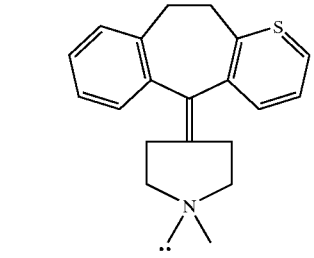

pizotyline

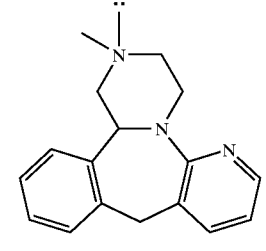

mirtazapine (Remeron)

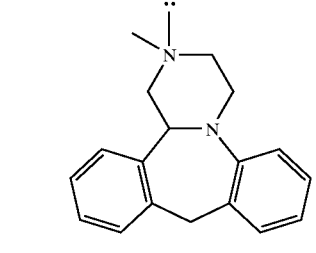

miansetin

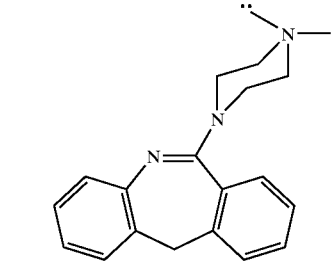

periapine

Ondansetron is a selective 5-HT3 antagonist. This receptor subtype is found on cholinergic neurons; when it is activated it inhibits release of acetylcholine. Along with its chemical relatives such as granisetron and zatosetron, it may thus be useful in reviving memory function in the aged. Granisetron is also used as an antiemetic (Kytril) in chemotherapy.

Ketanserin, a selective 5-HT2 antagonist, also acts on alpha-1 adrenoceptors to lower blood pressure. Mescaline, a hallucinogen, antagonizes 5-HT2 terminals and has been tried as an alternative to dopamine blocking antipsychotics (without much success; it facilitates dopamine function). Oxetorone is a relatively new antagonist used against migraine, as is pizotyline. Cyroheptadiene is an older serotonin antagonist and antihistaminic. Mirtazapine (Remeron) causes serotonin release, but blocks the 5-HT2 and 5-HT3 subreceptors, effectively augmenting serotonin action at 5-HT1 receptors. Mianserin and homochlorcyclizine also antagonize serotonin receptors.

Serotonin agonists 2-methyl-serotonin

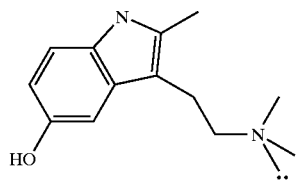

sumatriptan (Imitrex)

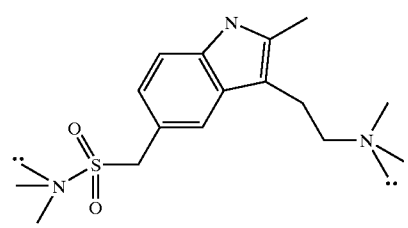

zolmitriptan (Zomig)

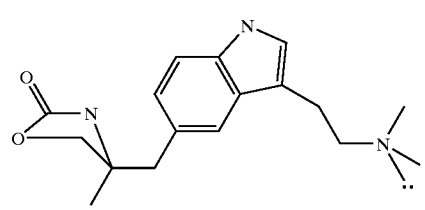

rizatriptan (Maxalt)

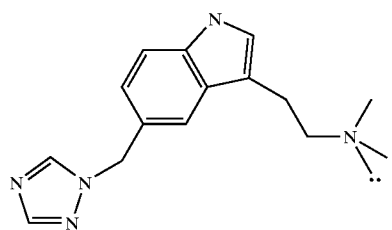

8-hydroxy-DPAT

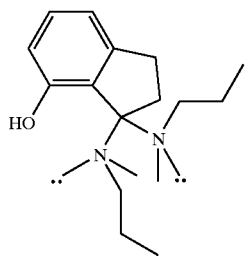

gepirone

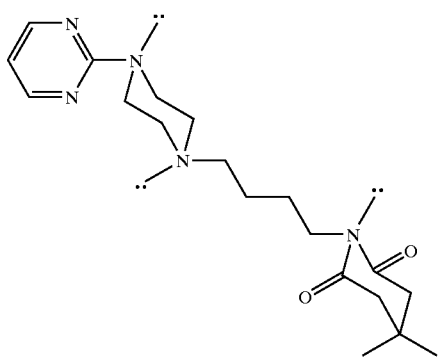

buspirone

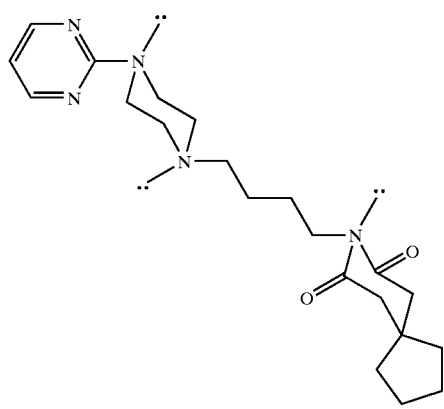

ipsapirone

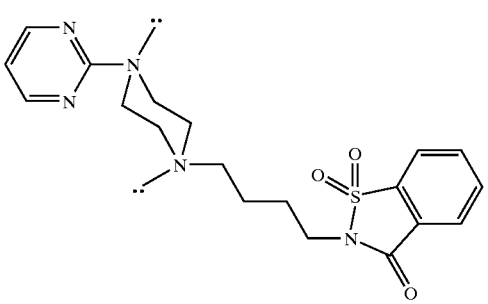

Sumatriptan activates 5-HT1d terminals, and is used against migraine under the trade name Imitrex. Zolmitriptan (Zomig) and rizatriptan (Maxal) are similar, recently approved, antimigraine serotonin drugs.

Buspirone, ipsapirone and gepirone enjoy 5-HT1 agonist properties with only weak D2 blocking effects. Buspirone is used against anxiety as an alternative to GABA-mimetic sedatives. 8-hydroxy-DPAT acts selectively at 5-HT1 a receptors, while 2-methylserotonin activates 5-HT3 terminals.

Steroids & Reproductive Drugs

Steroids are fat-soluble (lipophilic) hormones with a tetracyclic base structure. The steroid structure is synthesized from smaller structures called terpenes to precursor molecules, which then undergo extensive and subtle alterations for a rich variety of uses: to control systems, often in fatty tissues, as diverse as meiosis, carbohydrate metabolism, fat storage, muscle growth, immune function, and nerve cell membrane chemistry. Because of their high lipophilicity, they can pass through cell membranes, which are fatty bilayers, and influence DNA transcription and thereby alter protein synthesis. By binding to specific sites on the DNA, they release a kind of molecular "boot" (hsp90) that, in the absence of steroid, locks up the DNA and prevents a short-sequence from being expressed into a protein. The action of the enzymes or active peptides generated by the activation of the DNA can persist for long periods of time, explaining the long duration of action of many steroids.

Steroids may be separated into the broad groups of gonadal compounds and glucocorticoids, depending on the site of synthesis, which is in the ovary or testis for the gonadal variety and in the adrenal cortex for glucocorticoids. They may also be divided according to function, with the usual designations being androgens, estrogens, and progestogens (typically for the gonadal hormones) and anabolics and catabolics (typically for the glucocorticoids).

It is important to realize, however, that these terms are not totally exclusive. That is, even the gonadal hormone testosterone is synthesized in small quantities by the adrenal gland, and imparts anabolic properties separate from its effects on gonad function. Moreover, all hormones act in coordination with other compounds to produce a net result.

Gonadal steroids

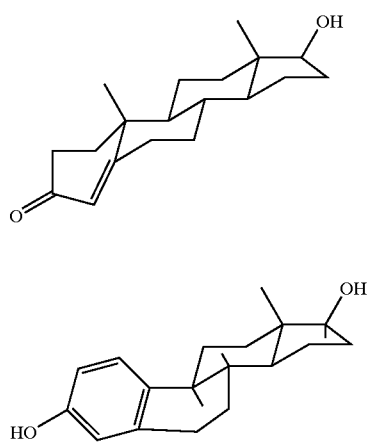

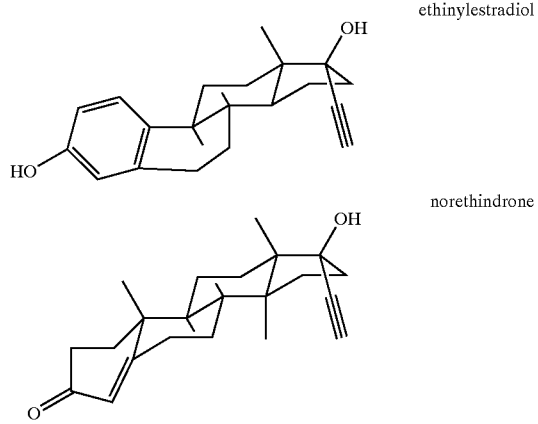

Testosterone is the prototype of the androgen group of gonadal steroids. Androgens impart features typified by males of mammalian species. These include morphological features such as a protruding browridge, robust bone structure, and large canines. It is also responsible for aggression and libido. It also acts as an anabolic, aiding muscle formation in response to exercise. Estradiol, meanwhile, is the prototypical estrogen, imparting female characteristics such as breast growth and storage of subcutaneous fat. Estrogens also prevent heart disease (women get it statistically less than men).

Oral contraceptives reformulate the body's steroid chemistry to mimic that of pregnancy to prevent ovulation. This is usually done in accordance with the natural 28 day menstrual cycle, although it is possible to trick the body into delaying ovulation for longer periods. This is accomplished by a mixture of an estrogen and a progestogen. The most popular preparation is norethindrone (a progestogen) and ethinylestradiol (an estrogen). This combination, taken in a large dose just after unprotected sex, can also prevent pregnancy by the same mechanism. Replacement therapy for gonadal steroids in the form of testosterone for men and estrogen/progesterones (depot ProVera) and recently also testosterone for women has been tried to combat the symptoms of aging, including diminished sex drive. In men, testosterone helps libido and may improve cardiovascular fitness and general vigor. In women, the drop in estrogen after menopause imparts some changes, but the drop is relatively modest (20% or so) compared to the drop in progesterone, which causes osteoblasts to make new bone tissue and inhibits cancer cell formation. Since estrogens, being anabolic or tissue-building compounds, can promote cancer cell growth, modem replacement formulations should compensate more for progesterones than estrogens. Non-steroidal soybean estrogens are now marketed as treatments for menopausal hot flashes, and testosterone creams and tablets to increase sex drive.

Glucocorticoids

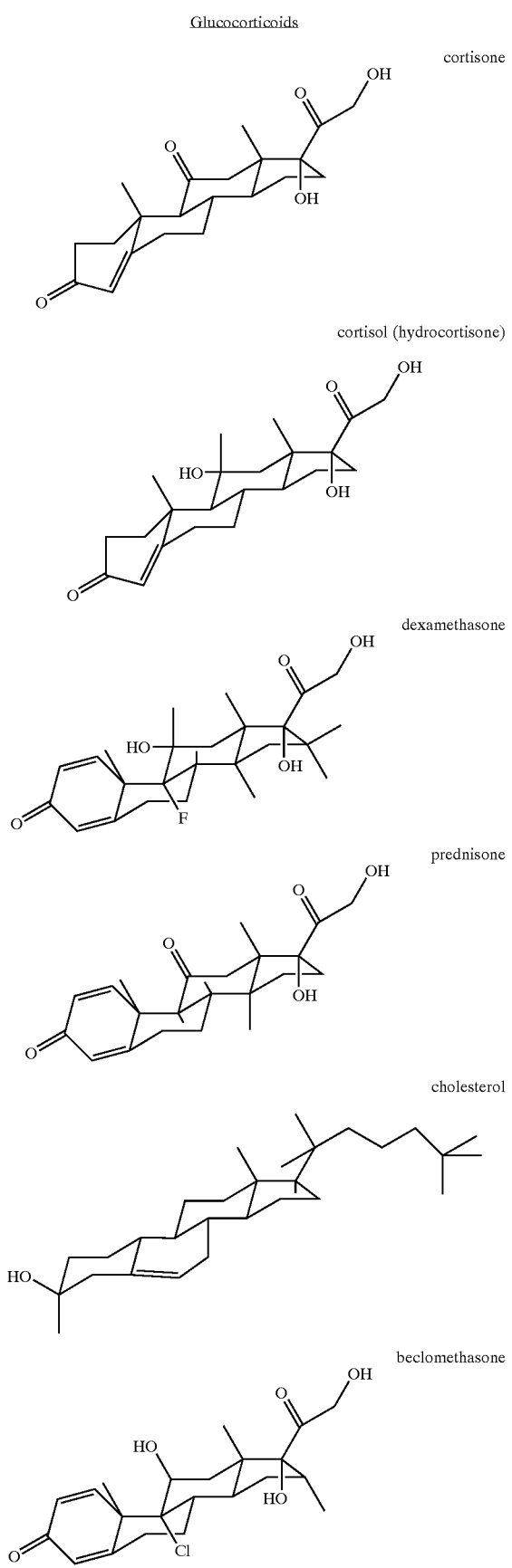

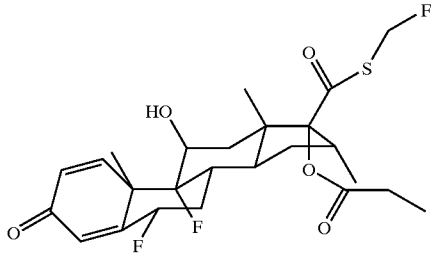

Cholesterol is heavily involved in membrane in metabolic chemistries. One of its main uses in the body is to decrease the permeability of phospholipid cell walls to ionic species such as $Na^+$, $K^+$, and $Ca^{++}$. In recent years it has been implicated in aiding the accumulation of plaque on the interior surfaces of veins and arteries. Animal meat is typically rich in cholesterol. Through natural selection, carnivores such as cats and dogs have developed different chemistries adjusted for processing higher amounts of cholesterol, cholestanol (the saturated from), and other steroids, which make diets higher in meat safer for them than for us. Cholesterol is excreted through gall, a fatty digestive substance secreted from the liver. It is present in high quantities in gallstones. Bile is also used to excrete fat-soluble substances such as bilirubin (from the heme group in decomposed red blood cells). Cholesterol is also used endogenously to synthesize vitamin D.

Cortisone, another prototypical glucocorticoid, controls healing processes associated with the immune system, as well as regulating membrane and other functions. Hydrocortisone, also known as cortisol, works similarly to inhibit histamine-mediated allergic reaction and regulates the body's response to stress by modulating the chemistry of neuronal excitable membranes. Prednisone is a synthetic compound used regularly in place of cortisone. Dexamethasone has been used to diagnose depression, i.e. in the dexamethasone suppression test, where the body is "stressed" by introduction of the steroid and its response is measured.

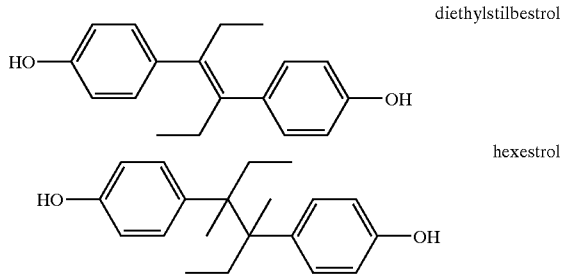

Hexestrol and diethylstilbestrol are two examples of polycyclic, non-steroid compounds which activate estrogen receptors. The local structure in the bound configuration resembles that of steroids. The other main category of non-steroidal estrogens is the isoflavones.

Environmental estrogens have become a health concern since cattle are commonlty fed estrogens due to their anabolic (weight-gain) properties. Ingestion of meat therefore equates to absorbing some estrogens. Some pesticides are non-steroidal estrogens, as is THC, the main psychoactive constituent of marijuana. Compounds such as diethylstilbestrol have been shown to be carcinogens, though this is not due to action on DNA.

Tamoxifen & raloxifene

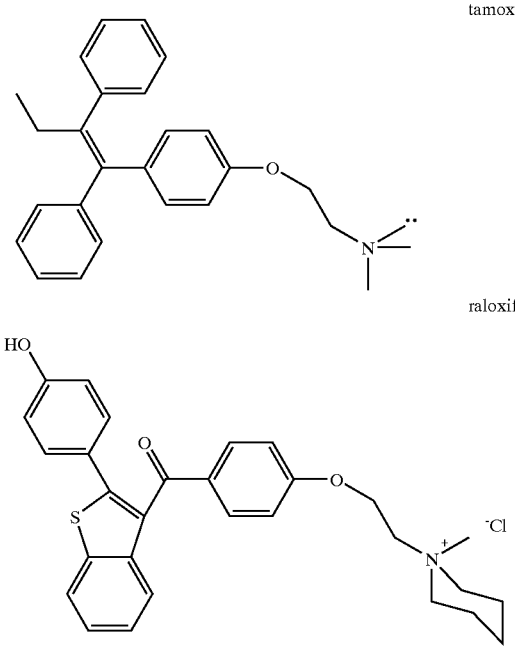

Recently, two nonsteroidal estrogen agents have shown great medical promise in several women's health issues. These selective estrogen receptor modulators (SERMs) mimic the effects of estrogens in some tissues but not others.

Tamoxifen has been used for years following detection of breast cancer. By blocking estrogen receptors, it discourages tumor growth. New studies show it may also prevent breast cancer, probably by the same mechanism. However, the benefits of this prevention must be weighed against the increased risk of uterine cancer and other potential risks.

Raloxifene retains the ability to promote bone maintenance and prevent osteoporosis; it cuts the risk of breast cancer by as much as 60%, and decreases levels of LDLs ("bad" cholesterol).

Finasteride (Propecia)

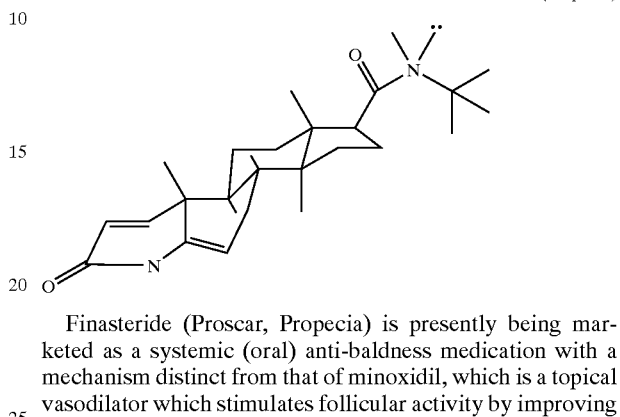

Finasteride (Proscar, Propecia) is presently being marketed as a systemic (oral) anti-baldness medication with a mechanism distinct from that of minoxidil, which is a topical vasodilator which stimulates follicular activity by improving blood flow. Finasteride works by inhibiting the formation of 5-alpha-dihydrotestosterone, a potent androgen, from the less potent parent compound, testosterone. It has also been used to treat benign prostatic hypertrophy (enlargement of the prostate).

The side effects of reducing androgens in the body can be essentially termed feminization: atrophy of the male gonads, breast augmentation, decrease in aggressive behavior, increased risk of osteoporosis, etc.

Plant steroids

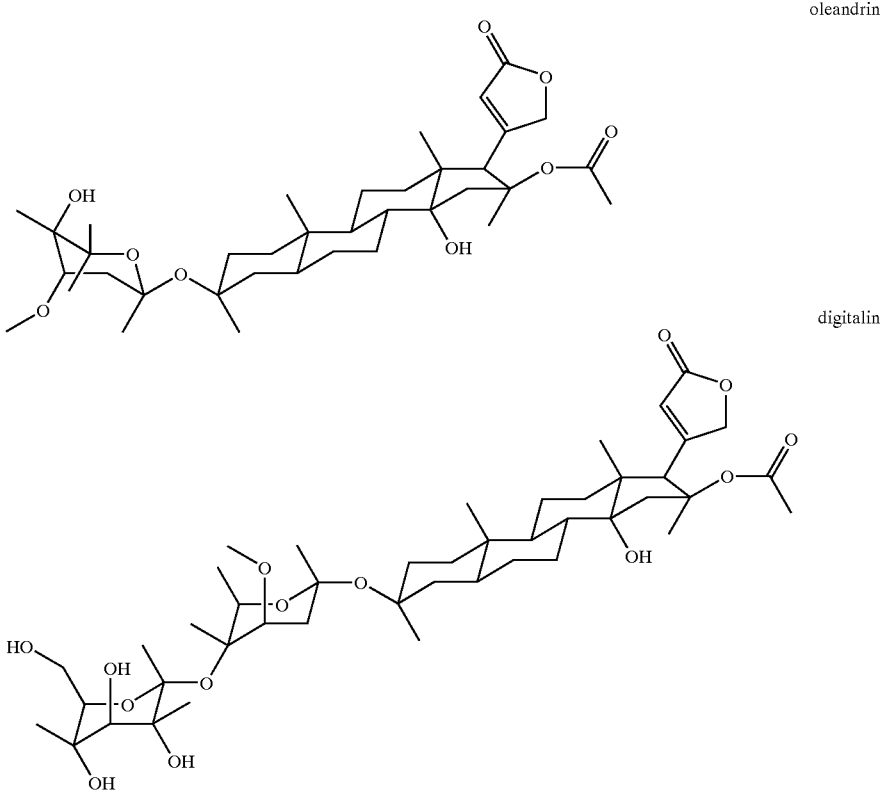

Steroids are not confined to the animal kingdom but are synthesized by plants as well. The well-known cardiotonic digitalis is derived from the foxglove plant which synthesizes several glucoside steroids (i.e. steroids bonded to sugar moieties).

The oleander shrub generates several steroids with similar effects on cardiac conduction, including oleandrin and oleandrigenin.

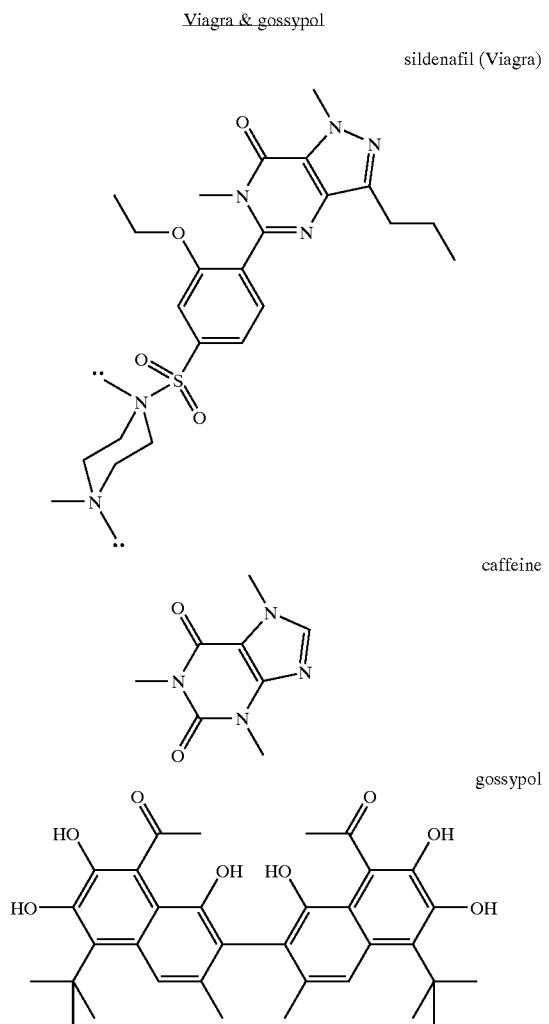

Sildenafil (Viagra) is a erection facilitator. Erection depends on an interaction of adrenergic and cholinergic neurons in which muscles must relax to let blood into erectile tissue. The presence of nitrous oxide (NO) species is involved, and Viagra may affect the enzymes responsible for generating NO. Viagra is also a selective inhibitor of cGMP phophodiesterase, which acts in some GI vascular smoothmuscles. Caffeine, wose central ring structure resembles Viagra's, works similarly on the more widespread cAMP phosphodiesterase, a more widespread second messenger system. Yohimbine, a selective alpha2 adrenergic blocker, has also been touted as being able to prolong or intensify erection.

Gossypol, isolated from the cotton plant, has the ability to inhibit production of viable sperm in men. It damages the epithelial lining of seminferous vesicles, inhibiting sperm formation. It also poisons the oxygen-carrying capacity of blood.

Among peptide therapeutic candidates are peptides which demonstrate anti-neoplastic activity, such as the RGD peptides including peptide SEQ ID NOS. 1–3.

Also included are peptides that are active against HIV, including the GP-41 peptides including peptide SEQ ID NOS. 4–6.

Anti-viral peptides which demonstrate the ability to disrupt fusogenic events common in viral infections. These include the RSV peptides which demonstrate the ability to treat or prevent infection by respiratory syncytial virus (RSV) as well as acquired immune deficiency syndrome (AIDS) caused by infection of the human immunodeficiency virus (HIV). Such peptides include peptide SEQ NOS. 7–9.

Also included are GLP-1 peptides including those peptides depicted in SEQ ID NOS. 10–11.

Also included are Kringle or K5 peptides including those peptides depicted in SEQ ID NOS. 12–13; BBB peptides (TAT) including those peptides depicted in SEQ ID NOS. 14–15 and analgesic peptides, such as dynorphins, are also useful, including peptide SEQ ID NO. 16.

3. Modified Therapeutic Agents

The modified therapeutic agents of the present invention comprise therapeutic agents that have been modified by attaching a reactive group. The reactive group may be attached to the therapeutic agent via a linking group, or optionally without using a linking group. The modified therapeutic agents can react with the available functionalitieson blood or pulmonary components or blood components via covalent linkages. The invention also relates to such modifications, such combinations with pulmonary components or blood components, and methods for their use. These methods include extending the effective therapeutic life of the conjugated therapeutic agents as compared to administration of unconjugated therapeutic agents.

To form covalent bonds with functionalities on a protein, one may use as a reactive group a wide variety of active carboxyl groups, particularly esters, where the hydroxyl moiety is physiologically acceptable at the levels required to modify the therapeutic agent. While a number of different hydroxyl groups may be employed, the most convenient would be N-hydroxysuccinimide (NHS), N-hydroxysulfosuccinimide (sulfo-NHS), maleimide, maleimide acids including but not limited to maleimidopropionic acid (MPA), and maleimide esters. In the preferred embodiments of this invention, the functionality on the blood component will be a thiol group and the reactive group will a maleimide.

Primary amines are the principal targets for NHS esters. Accessible α-amine groups present on the N-termini of proteins react with NHS esters. However, α-amino groups on a protein may not be desirable or available for the NHS coupling. While five amino acids have nitrogen in their side chains, only the ε-amine of lysine reacts significantly with NHS esters. An amide bond is formed when the NHS ester conjugation reaction reacts with primary amines releasing N-hydroxysuccinimide as demonstrated in the schematic below.

NHS-Ester Reaction Scheme

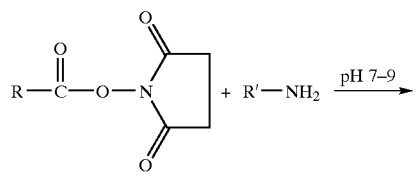

-continued

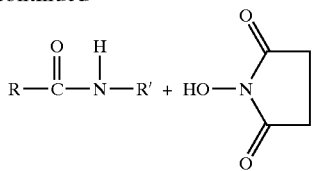

In the preferred embodiments of this invention, the functional group on this protein will be a thiol group and the chemically reactive group will be a maleimido-containing group such as MPA or GMBA (gamma-maleimide-butyralamide). The maleimido group is most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions, as demonstrated in the following schematic.

Maleimide Reaction Scheme

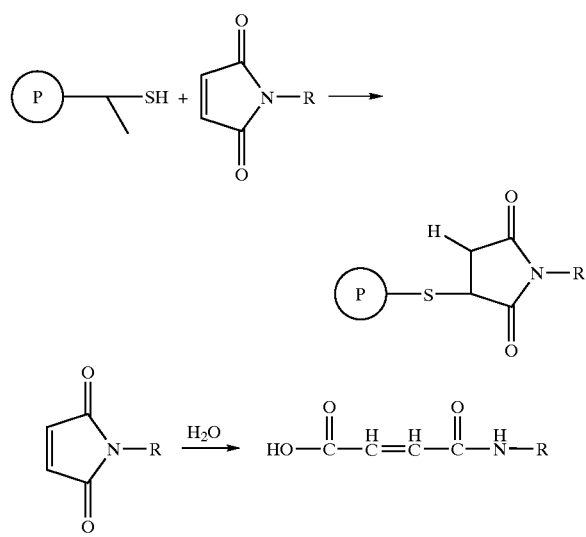

A. Specific Labeling.

Preferably, the modified therapeutic agents of this invention are designed to specifically react with thiol groups on pulmonary proteins or mobile blood proteins. Such reaction is preferably established by covalent bonding of the therapeutic agent modified with a maleimide link (e.g. prepared from GMBS, MPA or other maleimides) to a thiol group on a pulmonary protein, such as intra- or extra-cellular albumin, or a mobile blood protein such as serum albumin or IgG.

Under certain circumstances, specific labeling with maleimides offers several advantages over non-specific labeling of proteins with groups such as NHS and sulfo-NHS. Thiol groups are less abundant in vivo than amino groups. Therefore, the maleimide-modified therapeutic agents of this invention, i.e., maleimide therapeutic agents, will covalently bond to fewer proteins. For example, in albumin (the most abundant blood protein) there is only a single thiol group. Thus, therapeutic agent-maleimide-albumin conjugates will tend to comprise approximately a 1:1 molar ratio of therapeutic agent to albumin. In addition to albumin, IgG molecules (class II) also have free thiols. In the case of systemic delivery, since IgG molecules and serum albumin make up the majority of the soluble protein in blood they also make up the majority of the free thiol groups in blood that are available to covalently bond to maleimide-modified therapeutic agents.

Further, even among free thiol-containing blood proteins, including IgGs, specific labeling with maleimides leads to the preferential formation of therapeutic agent-maleimide-albumin conjugates, due to the unique characteristics of albumin itself. The single free thiol group of albumin, highly conserved among species, is located at amino acid residue 34 ($Cys^{34}$). It has been demonstrated recently that the $Cys^{34}$ of albumin has increased reactivity relative to free thiols on other free thiol-containing proteins. This is due in part to the very low pK value of 5.5 for the $Cys^{34}$ of albumin. This is much lower than typical pK values for cysteine residues in general, which are typically about 8. Due to this low pK, under normal physiological conditions $Cys^{34}$ of albumin is predominantly in the ionized form, which dramatically increases its reactivity. In addition to the low pK value of $Cys^{34}$, another factor which enhances the reactivity of $Cys^{34}$ is its location, which is in a crevice close to the surface of one loop of region V of albumin. This location makes $Cys^{34}$ very available to ligands of all kinds, and is an important factor in $Cys^{34}$'s biological role as free radical trap and free thiol scavenger. These properties make $Cys^{34}$ highly reactive with maleimide-therapeutic agents, and the reaction rate acceleration can be as much as 1000-fold relative to rates of reaction of maleimide-therapeutic agents with other free-thiol containing proteins.

Another advantage of therapeutic agent-maleimide-albumin conjugates is the reproducibility associated with the 1:1 loading of therapeutic agent to albumin specifically at $Cys^{34}$. Other techniques, such as glutaraldehyde, DCC, EDC and other chemical activations of, e.g, free amines, lack this selectivity. For example, albumin contains 52 lysine residues, 25–30 of which are located on the surface of albumin and therefore accessible for conjugation. Activating these lysine residues, or alternatively modifying therapeutic agents to couple through these lysine residues, results in a heterogenous population of conjugates. Even if 1:1 molar ratios of therapeutic agent to albumin are employed, the yield will consist of multiple conjugation products, some containing 0, 1, 2 or more therapeutic agents per albumin, and each having therapeutic agents randomly coupled at any one or more of the 25–30 available lysine sites. Given the numerous possible combinations, characterization of the exact composition and nature of each conjugate batch becomes difficult, and batch-to-batch reproducibility is all but impossible, making such conjugates less desirable as a therapeutic. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting properties of Methotrexate-Albumin Conjugates in Rats," *Anti-Cancer Drugs*, Vol. 8, pp. 677–685 (1988), incorporated herein in its entirety, the authors report that a 1:1 ratio of the anti-cancer methotrexate to albumin conjugated via glutaraldehyde gave the most promising results. These conjugates were preferentially taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of maleimide-therapeutic agents in vivo, one can control the specific labeling of albumin and IgG in vivo. For systemic delivery via pulmonary administration, in typical administrations, 80–90% of the administered maleimide-therapeutic agents that reach the bloodstream will label albumin and less than 5% will label IgG. Trace labeling of free thiols such as glutathione will also occur. Such specific labeling is preferred for in vivo use as it permits an accurate calculation of the estimated half-life of the administered agent.

In addition to providing controlled specific in vivo labeling, maleimide-therapeutic agents can provide specific labeling of albumin or other proteins ex vivo. Such ex vivo labeling involves the addition of maleimide-therapeutic agents to a saline solution containing albumin or other protein. Once conjugation has occurred ex vivo with the maleimide-therapeutic agents, the saline solution can be administered via pulmonary delivery for in vivo treatment.

In contrast to NHS-therapeutic agents, maleimide-therapeutic agents are generally quite stable in the presence of aqueous solutions and in the presence of free amines. Since maleimide-therapeutic agents will only react with free thiols, protective groups are generally not necessary to prevent the maleimide-therapeutic agents from reacting with itself. In addition, the increased stability of the modified therapeutic agent permits the use of further purification steps such as HPLC to prepare highly purified products suitable for in vivo use. Lastly, the increased chemical stability provides a product with a longer shelf life.

B. Non-Specific Labeling.

The therapeutic agents of the invention may also be modified for non-specific labeling of pulmonary or blood components. Bonds to amino groups will also be employed, particularly with the formation of amide bonds for non-specific labeling. To form such bonds, one may use as a chemically reactive group a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxysulfosuccinimide (sulfo-NHS).

Other linking agents which may be utilized are described in U.S. Pat. No. 5,612,034, which is hereby incorporated herein.

The various sites with which the chemically reactive group of the modified therapeutic agents may react in vivo include cells, particularly the alveolar cells and capillary endothelial cells that make up the alveoli in the lungs as well as red blood cells (erythrocytes) and platelets in the blood itself. The agents may also react with pulmonary proteins, including membrane bound receptors, intra- and extra-cellular albumin, immunoglobulins, ferritin, and transferrin, and serum proteins of the blood, such as immunoglobulins, including IgG and IgM, serum albumin, ferritin, steroid binding proteins, transferrin, thyroxin binding protein, α-2-macroglobulin, and the like. Those receptors with which the modified therapeutic agents react, which are not long-lived, will generally be eliminated from the human host within about three days. The proteins indicated above (including the proteins of the cells) will remain at least three days, and may remain five days or more (usually not exceeding 60 days, more usually not exceeding 30 days) particularly as to the half life, based on the concentration in the blood.

For the most part, for systemic delivery of the therapeutic agent, reaction will be with mobile components in the blood, particularly blood proteins and cells, more particularly blood proteins and erythrocytes. By "mobile" is intended that the component does not have a fixed situs for any extended period of time, generally not exceeding 5 minutes, more usually one minute, although some of the blood component may be relatively stationary for extended periods of time. Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The desired conjugates of non-specific modified therapeutic agents to blood components may be prepared in vivo by pulmonary administration of the modified therapeutic agents to the patient, which may be a human or other mammal. If desired, the subject conjugates may also be prepared ex vivo by combining a carrier protein or protein solution with modified therapeutic agents of the present invention, allowing covalent bonding of the modified therapeutic agents to functionalitieson the protein and then administering the conjugated mixture to the host via pulmonary delivery.

3. Diagnostic Agents and Modified Diagnostic Agents

Diagnostic agents are agents useful in imaging the mammalian vascular system and include such agents as position emission tomography (PET) agents, computerized tomography (CT) agents, magnetic resonance imaging (MRI) agents, nuclear magnetic imaging agents (NMI), fluroscopy agents and ultrasound contrast agents.

The modified diagnostic agent of the present invention will, for the most part, have the following formula: X-Y-Z.

In the formula, X is a diagnostic agent selected from PET agent, CT agents, MRI agents, NMI agents, fluroscopy agents and ultrasound contrast agents. Diagnostic agents of interest include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, etc.

In the formula, Y is a linking group of from 0–30, more usually of from 2–12, preferably of from 4–12 atoms, particularly carbon, oxygen, phosphorous and nitrogen, more particularly carbon and oxygen, where the oxygen is preferably present as oxy ether, where Y may be alkylene, oxyalkylene, or polyoxyalkylene, where the oxyalkylene group has from 2–3 carbon atoms, and the like. A linking group of 0 atoms is preferred when it is desired to place X as close to Z as possible.

In the formula, Z is a reactive entity, such as carboxy, carboxy ester, where the ester group is of 1–8, more usually 1–6 carbon atoms, particularly a physiologically acceptable leaving group which activates the carboxy carbonyl for reaction with amino groups in an aqueous system, e.g. N-hydroxysuccinimide (NHS), N-hydroxysulfosuccinimide, (sulfo-NHS), maleimide, maleimide esters, maleimide acids, maleimide-benzoyl-succinimide (MBS), gamma-maleimido-butyryloxy succinimide ester (GMBS) and maleimidopropionic acid (MPA), N-hydroxysuccinimide isocyanate, isothiocyanate, thiolester, thionocarboxylic acid ester, imino ester, mixed anhydride, e.g. carbodiimide anhydride, carbonate ester, etc. and the like. The reactive entity Z will covalently bond to functionalities in vivo or ex vivo.

4. Synthesis of Peptide Therapeutic Agents

A. Peptide Synthesis

Therapeutic agents according to the present invention that are peptides may be synthesized by standard methods of solid phase peptide chemistry known to those of ordinary skill in the art. For example, peptides may be synthesized by solid phase chemistry techniques following the procedures described by Steward and Young (Steward, J. M. and Young, J. D., Solid Phase Peptide Synthesis, 2nd Ed., Pierce Chemical Company, Rockford, Ill., (1984) using an Applied Biosystem synthesizer. Similarly, multiple peptide fragments may be synthesized then linked together to form larger peptides. These synthetic peptides can also be made with amino acid substitutions at specific locations.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Acacemic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and the process is repeated.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, a, a-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of the peptides of the present invention. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-. Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris (dimethylamino)phosphonium-hexafluorophosphate (BOP) or bis(2-oxo-3-oxazolidinyl)phosphine chloride (BOPCI), mediated coupling for from about 1 to about 24 hours at a temperature of between 10° and 50° C. in a solvent such as dichloromethane or DMF.

When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. The preferred method for coupling to the deprotected 4-(2',4'-dimethoxyphenyl-Fmoc-aminomethyl)phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Molecular weights of these ITPs are determined using Fast Atom Bombardment (FAB) Mass Spectroscopy.

(1) N-Terminal Protective Groups

As discussed above, the term "N-protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, "Protective Groups In Organic Synthesis," (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro4, 5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like.

(2) Carboxy Protective Groups

As discussed above, the term "carboxy protecting group" refers to a carboxylic acid protecting ester or amide group employed to block or protect the carboxylic acid functionality while the reactions involving other functional sites of the compound are performed. Carboxy protecting groups are disclosed in Greene, "Protective Groups in Organic Synthesis" pp. 152–186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$–$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereofsuch as 5-indanyl and the like; dialkylaminoalkyl such as dimethylaminoethyl and the like; alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl,1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and the like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl) alkyl such as (5-t-butyl-2-oxo-1,3-dioxolen-4-yl)methyl and the like; and (5-phenyl-2-oxo-1,3-dioxolen4-yl)alkyl such as (5-phenyl-2-oxo-1,3-dioxolen-4-yl)methyl and the like.

Representative amide carboxy protecting groups are aminocarbonyl and loweralkylaminocarbonyl groups.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester. Preferred amide carboxy protecting groups are loweralkylaminocarbonyl groups. For example, aspartic acid may be protected at the α-C-terminal by an acid labile group (e.g. t-butyl) and protected at the β-C-terminal by a hydrogenation labile group (e.g. benzyl) then deprotected selectively during synthesis.

B. Peptide Modification

The manner of producing the modified peptides of the present invention will vary widely, depending upon the nature of the various elements comprising the peptide. The synthetic procedures will be selected so as to be simple, provide for high yields, and allow for a highly purified stable product. Normally, the chemically reactive group will be created at the last stage of the synthesis, for example, with a carboxyl group, esterification to form an active ester. Specific methods for the production of modified peptides of the present invention are described below.

Specifically, the selected peptide is modified with the linking group only at either the N-terminus, C-terminus or interior of the peptide. The therapeutic activity of this modified peptide-linking group is then assayed. If the therapeutic activity is not reduced dramatically (i.e., reduced less than 10-fold), then the stability of the modified peptide-linking group is measured by its in vivo lifetime. If the stability is not improved to a desired level, then the peptide is modified at an alternative site, and the procedure is repeated until a desired level of therapeutic and stability is achieved.

More specifically, each peptide selected to undergo modification with a linking group and a reactive group will be modified according to the following criteria: if a terminal carboxylic group is available on the peptide and is not critical for the retention of therapeutic activity, and no other sensitive functional group is present on the peptide, then the carboxylic acid will be chosen as attachment point for the linking group-reactive group modification. If the terminal carboxylic group is involved in therapeutic activity, or if no carboxylic acids are available, then any other sensitive functional group not critical for the retention of therapeutic activity will be selected as the attachment point for the linking group-reactive entity modification. If several sensetive functional groups are available on a a peptide, a combination of protecting groups will be used in such a way that after addition of the linking group/reactive entity and deprotection of all the protected sensetive functional groups, retention of therapeutic activity is still obtained. If no sensetive functional groups are available on the peptide, or if a simpler modification route is desired, synthetic efforts will allow for a modification of the original peptide in such a way that retention of therapeutic is maintained. In this case the modification will occur at the opposite end of the peptide An NHS derivative may be synthesized from a carboxylic acid in absence of other sensetive functional groups in the peptide. Specifically, such a peptide is reacted with N-hydroxysuccinimide in anhydrous $CH_2Cl_2$ and EDC, and the product is purified by chromatography or recrystallized from the appropriate solvent system to give the NHS derivative.

Alternatively, an NHS derivative may be synthesized from a peptide that contains an amino and/or thiol group and a carboxylic acid. When a free amino or thiol group is present in the molecule, it is preferable to protect these sensetive functional groups prior to perform the addition of the NHS derivative. For instance, if the molecule contains a free amino group, a transformation of the amine into a Fmoc or preferably into a tBoc protected amine is necessary prior to perform the chemistry described above. The amine functionality will not be deprotected after preparation of the NHS derivative. Therefore this method applies only to a compound whose amine group is not required to be freed to induce the desired therapeutic effect. If the amino group needs to be freed to retain the original properties of the molecule, then another type of chemistry described below has to be performed.

In addition, an NHS derivative may be synthesized from a peptide containing an amino or a thiol group and no carboxylic acid. When the selected molecule contains no carboxylic acid, an array of bifunctional linking groups can be used to convert the molecule into a reactive NHS derivative. For instance, ethylene glycol-bis (succinimydylsuccinate) (EGS) and triethylamine dissolved in DMF and added to the free amino containing molecule (with a ratio of 10:1 in favor of EGS) will produce the mono NHS derivative. To produce an NHS derivative from a thiol derivatized molecule, one can use N-[-maleimidobutyryloxy]succinimide ester (GMBS) and triethylamine in DMF. The maleimido group will react with the free thiol and the NHS derivative will be purified from the reaction mixture by chromatography on silica or by HPLC.

An NHS derivative may also be synthesized from a peptide containing multiple sensetive functional groups. Each case will have to be analyzed and solved in a different manner. However, thanks to the large array of protecting groups and bifunctional linking groups that are commercially available, this invention is applicable to any peptide with preferably one chemical step only to modify the peptide (as described above) or two steps (as described above involving prior protection of a sensetive group) or three steps (protection, activation and deprotection). Under exceptional circumstances only, would multiple steps (beyond three steps) synthesis be required to transform a peptide into an active NHS or maleimide derivative.

A maleimide derivative may also be synthesized from a peptide containing a free amino group and a free carboxylic acid. To produce a maleimide derivative from a amino derivatized molecule, one can use N-[γ-maleimidobutyryloxy]succinimide ester (GMBS) and triethylamine in DMF. The succinimide ester group will react with the free amino and the maleimide derivative will be purified from the reaction mixture by crystallization or by chromatography on silica or by HPLC.

Finally, a maleimide derivative may be synthesized from a peptide containing multiple other sensetive functional groups and no free carboxylic acids. When the selected molecule contains no carboxylic acid, an array of bifunctional crosslinking reagents can be used to convert the molecule into a reactive NHS derivative. For instance maleimidopropionic acid (MPA) can be coupled to the free amine to produce a maleimide derivative through reaction of the free amine with the carboxylic group of MPA using HBTU/HOBt/DIEA activation in DMF.

Many other commercially available heterobifunctional crosslinking reagents can alternatively be used when needed. A large number of bifunctional compounds are available for linking to entities. Illustrative reagents include: azidobenzoyl hydrazide, N-[4-(p-azidosalicylamino)butyl]-3'-[2'-pyridyld ithio)propionamide), bis-sulfosuccinimidyl suberate, dimethyl adipimidate, disuccinimidyl tartrate, N-y-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl 4-[N-maleimidomethyl]cyclohexane-1-carboxylate.

5. Synthesis of Modified Organic Therapeutic Agents

Similar to procedures for modified peptide therapeutics, the synthetic procedures used to prepare modified organic therapeutics will also be selected so as to be simple, provide for high yields, and allow for a highly purified product. Normally, the chemically reactive group will be created as the last stage, for example, with a carboxyl group, esterification to form an active ester will be the last step of the synthesis. Methods for the production and/or modification of organic therapeutic agents of the present invention are described in the Examples below.

Each organic therapeutic agent selected to undergo the derivatization with a linking group and a reactive group will be modified according to the following criteria: Generally, the therapeutic agents are commercially available. If not, they can be synthesized by procedures well known in the art. As a first step, the therapeuticlly active region of the therapeutic agent is identified. Next, the therapeutic agent is modified at a site sufficiently far away from the active portion to prevent a potential interference between the modified drug and the target site of the drug, such that the modified agent substantially retains its therapeutic activity, (i.e. the therapeutic activity is reduced by no more than 10 fold). Finally, keeping constant the site of chemical modification, optimize the biological activity of the modified agent by modifying the length and nature of the linking group.

If a carboxylic group, not critical for the retention of pharmacological activity is available on the original molecule and no other reactive functionality is present on the molecule, then the carboxylic acid will be chosen as attachment point for the linking group-reactive entity modification. If no carboxylic acids are available, then any other functionalities not critical for the retention of pharmacological activity will be selected as attachment point for the linking group-reactive entity modification. If several functionalities are available on a therapeutic agent, a combination of protecting groups will be used in such a way that after addition of the linking group/reactive entity and deprotection of all the protected functionalities, retention of pharmacological activity is still obtained. If no functionalitiesare available on the therapeutic agent, synthetic efforts will allow for a modification of the original parent drug in such a way that retention of biological activity and retention of receptor or target specificity is obtained.

Where the derivatized therapeutic agent of the present invention represents a derivatized enzyme inhibitor will generally have substantially lower $IC_{50}$'s generally in the range of about 0.5–0.01 of the $IC_{50}$ of the parent molecule. Desirably, the $IC_{50}$ should be not less than 0.05, preferably not less than about 0.1. In view of the varying $IC_{50}$'s, the amount of the derivatized therapeutic agent administered will also vary.

The determination of the nature and length of the linking group will be performed through an empirical optimization phase and will be measured by the retention or the loss of biological activity. For instance, with a given inhibitor enzyme interactions, an iteration of the modification of the nature and the length of the linking group and a measure of the biological enzymatic activity may be necessary to determine the most favored linking group length and nature. Preferably a short hydrophilic 4–12 atom linking group easily synthesized will be favored to start the iteration process.

In the case of radiolabeled therapeutic agents, a minimum distance from the target has to be respected based on the nature of the isotope and its penetration. The length and nature of the linking groups are not as important as they are for an enzyme inhibitor combination. For instance an isotope that emits a beta rays like $^{32}P$ should be positioned within 5 mm from the target to have maximum efficiency (99%) with limited or no effect coming from a small change on the nature and length of the linking group.

6. Synthesis of Modified Diagnostic Agents

The manner of producing the modified diagnostic agents of the present invention will vary widely, depending upon the nature of the various elements comprising the molecule. The synthetic procedures will be selected so as to be simple, provide for high yields, and allow for a highly purified product. Normally, the chemically reactive group will be created as the last stage, for example, with a carboxyl group, esterification to form an active ester will be the last step of the synthesis. Methods for the production of the diagnostic agents of the present invention are described in the Examples.

7. Pulmonary Formulations and Delivery Methods

A further aspect of the invention is directed to aerosol compositions for treatment of the symptoms of pulmonary conditions. With therapeutic agents capable of forming a covalent bond with a pulmonary fluid protein. Alternatively, the therapeutic agent may be first conjugated with the pulmonary solution protein prior to administration.

The aerosol compositions may be composed of an aqueous solution suitable for inhalation consisting of at least 2.5% by weight (more preferably between about 3% and 10% by weight, and most preferably at least about 5% by weight) of a derivatized therapeutic agent. The droplets of the aerosol should be 10$\mu$ or less in diameter to maximize deposition in the lung alveoli rather than the throat or upper respiratory tract.

The invention also features inhaler devices for administration of the inhalable compositions (or medicaments) of the subject invention. In one aspect of the invention, the inhaler device comprises a housing defining a chamber which contains a dry powder. The dry powder is composed of therapeutic agent compound present in an amount that, upon administration will bind to pulmonary proteins. Alternatively, the agent may be covalently bonded to pulmonary proteins ex vivo prior to administration. At least 50% (preferably at least 70%, and more preferably at least 90%) of the powder consists of primary particles which have a diameter of 10 $\mu$m or less, and which may be agglomerated into larger particles or agglomerates which readily break down into primary particles upon inhalation from the device. The chamber has an opening through which the medicament can be drawn by inhalation by a patient.

In another aspect of the invention, the inhaler device comprises a vessel containing an inhalable medicament in the form of an aqueous solution suspended in a compressed or liquified propellant gas. At least 2.5% by weight (preferably at least 3%, more preferably at least 4%, even more preferably at least 5% and most preferably between 6 and 10%) of the aqueous solution is a pH-raising buffer compound.

The inhaler device may also have a housing defining a port onto which the vessel is mounted, a lumen in communication with the port, and a mechanism for controllably releasing the propellant from the vessel into the lumen, thereby releasing the suspended medicament from the vessel into the lumen. The lumen is configured to route the medicament suspended in the propellant into the respiratory system of the patient.

8. Therapeutic Uses of Modified Therapeutic Agents

The modified therapeutic agents of the invention find numerous uses, as enumerated below.

A. Therapeutic Uses of Modified Antineoplastic Agent

The antineoplastic agents of the invention, including but not limited to those specified in the examples, possess anti-angiogenic activity. As modified antineoplastic agents having anti-angiogenic activity, the compounds of the present invention are useful in the treatment of a variety of diseases, for example primary and metastatic solid tumors and carcinomas of the breast; colon; rectum; lung; oropharynx; hypopharynx; esophagus; stomach. Pancreas; liver; gallbladder; bile ducts; small intestine; urinary tract including kidney, bladder and urothelium; female genital tract including cervix, uterus, endometrium, ovaries, rhoriocarcinoma and festational trophoblastic disease; male genital tract including prostate, seminal vesicles, testes and germ cells tumors; endocrine glands including thyroid, adrenal and pituitary; skin including hmangiomas, melanomas, sarcomas arising from bone of soft tissues and Karposi's sarcoma, Wilm's tumor, rhabdomyosarcoma; tumor of the head and neck, brain, nerves, eyes, and meninges including astrocytomas, gliomas, glioblastomas, retinoblastomas, neuromas, neuroblastomas; tumors of the bone marrow and hematopoeitic tumors, solid tumors arising from hematopoietic malignancies such as leukemias and including chloromas, plasmocytomas, plagues and tumors of mycosis fungoides and cutaneous T-cell lymphoma/leukemia; acute lymphotic, actute granulocytic and chronic granulocytic leukemia; lymphomas including both Hodgkin's and non-Hodgkin's lymphomas; prophylaxis of autoimmune diseases including rheumatoid, immune and degenerative arthritis; ocular diseases including diabethic retinopathy; retinopathy of prematurity; corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferatrion withinatherosclerotic plaques; myocardial angiogenesis; plaque neovascularization; hemophiliac joints; angiofibroma; wound granulation; dieases charadterized by excessive or abnormal stimulation of endothelial cells including intestinal adhesion, Crohn's disease, atheroscelrosis, scleroderma and hypertrophic scars and diseases which have angiogenesis as a pathological consequence including ulcers (Helicobacter pilori); rheumatoid arthritis, osteogenic sarcoma, osteoarthritis, osteopenias such as osteoporosis, periodontitis, gingivitis, corneal epidermal or gastric ulceration, and tumor metastasis, invasion and growth, retinopathies, wound healing (ocular inflammation, soft and osseous tissue disease, gingivitis/periodontal disease), vascular disease (restenosis) annuerysm inflammation, autoimmune diseases, and rare cancers such as choriocarcinoma.

The compounds of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, compounds of the present invention may be administered with chemotherapeutic agents such as alpha-inferon, COMP (cyclophosphamnide, vincristine, methotraxate and prednisone), etoposide, mBACOD (methotraxate, bleomycin, doxorubicin, cyclophosphamide, vincristine and dexamethasone), PROMACE/MOPP (prednisone, methotrexate, doxirubicin, cyclophaophamide, taxol, etoposide/mechloetamine, vincristine, prednisone and procarbazine), vincristine, vinblastine, angioinhibins, TNP470, pentosan polysulfate, platelet factor4, angiostatin, LM-609, SU-101, CM-101, techgalan, thalidomide, SP-PG and the like. Other chemotherapeutic agents include alkylating agents such as nitrogen mustards including mechloethamine, melphanchloambucil, cyclophaosphamide, and ifosfamide; nirrosdoureas including carmustine, lomustine, semustine and streptozocin; alkyl sulfonates icluding busulfan; triazines including dacarbazine; ethyenimines including thiotepa na dhexamethylmelanine; folic acid analogs including methotraxate; pyrimidine analogs including 5-FU, cytosine arabinoside; purine analogs including 6-mercaptopurine and 6-thioguanine; antitumor antibiotics including actinomycin D; the anthraqcyclines including doxorubicin, bleomycin, mitomycin C and methramycin; hormones and hormones antagonists including tamoxifen and corticosteroids and mioscellaneous agnets including cisplatin and brequinar; fragments of plasminogen (kringle-5) as well as fragments from other integrin-binding substrates. For insnance, a tumor may be treated conventionally with surgery, radiation or chemiotherapy and administration of modified antineoplastic agents to extend the dormancy of micrometastasis and to inhibit the growth of any residual primary tumor.

B. Therapeutic Uses of Modified Matrix Metalloprotease Inhibitors

The MMPIs of the invention, including but not limited to those specified in the examples, possess anti-angiogenic activity. As modified matrix metalloprotease inhibitors having anti-angiogenic activity, the compounds of the present invention are useful in the treatment of a variety of diseases, for example primary and metastatic solid tumors and carcinomas of the breast; colon; rectum; lung; oropharynx; hypopharynx; esophagus; stomach. Pancreas; liver; gallbladder; bile ducts; small intestine; urinary tract including kidney, bladder and urothelium; female genital tract including cervix, uterus, ovaries, choriocarcinoma and festational trophoblastic disease; male genital tract including prostate, seminal vesicles, testes and germ cells tumors; endocrine glands including thyroid, adrenal and pituitary; skin including hmangiomas, melanomas, sarcomas arising from bone of soft tissues and Karposi's sarcoma; tumor of the nrain, nerves, eyes, and meninges including astrocytomas, gliomas, glioblastomas, retinoblastomas, neuromas, neuroblastomas; tumors of the bone marrow and hematopoeitic tumors, solid tumors arising from hematopoietic malignancies such as leukemias and including chloromas, plasmocytomas, plagues and tumors of mycosis fungoides and cutaneous T-cell lymphoma/leukemia; lymphomas including both Hodgkin's and non-Hodgkin's lymphomas; prophylaxis of autoimmune diseases including rheumatoid, immune and degenerative arthritis; ocular diseases including diabethic retinopathy; retinopathy of prematurity; corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferatrion withinatherosclerotic plaques; myocardial angiogenesis; plaque neovascularization; hemophiliac joints; angiofibroma; wound granulation; dieases charadterized by excessive or abnormal stimulation of endothelial cells including intestinal adhesion, Crohn's disease, atheroscelrosis, scleroderma and hypertrophic scars and diseases which have angiogenesis as a pathological consequence including ulcers (Helicobacter pilori); rheumatoid arthritis, osteoarthritis, osteopenias such as osteoporosis, periodontitis, gingivitis, corneal epidermal or gastric ulceration, and tumor metastasis, invasion and growth, retinopathies, wound healing (ocular inflammation, soft and osseous tissue disease, gingivitis/periodontal disease), vascular disease (restenosis) annuerysm inflammation and and autoimmune diseases. Another use is as birth control agent which inhibits ovulation and establishment of the placenta.

The compounds of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, compounds of the present invention may be administered with chemotherapeutic agents such as alpha-inferon, COMP (cyclophosphamnide, vincristine, methotraxate and prednisone), etoposide, mBACOD (methotraxate, bleomycin, doxorubicin, cyclophosphamide, vincristine and dexamethasone), PROMACE/MOPP (prednisone, methotrexate, doxirubicin, cyclophaophamide, taxol, etoposidelmechloetamine, vincristine, prednisone and procarbazine), vincristine, vinblastine, angioinhibins, TNP470, pentosan polysulfate, platelet factor4, angiostatin, LM-609, SU-101, CM-101, techgalan, thalidomide, SP-PG and the like. Other chemotherapeutic agents include alkylating agents such as nitrogen mustards including mechloethamine, melphanchloambucil, cyclophaosphamide, and ifosfamide; nirrosdoureas including carmustine, lomustine, semustine and streptozocin; alkyl sulfonates icluding busulfan; triazines including dacarbazine; ethyenimines including thiotepa na dhexamethylmelanine; folic acid analogs including methotraxate; pyrimidine analogs including 5-FU, cytosine arabinoside; purine analogs including 6-mercaptopurine and 6-thioguanine; antitumor antibiotics including actinomycin D; the anthraqcyclines including doxorubicin, bleomycin, mitomycin C and methramycin; hormones and hormones antagonists including tamoxifen and corticosteroids and mioscellaneous agnets including cisplatin and brequinar; fragments of plasminogen (kringle-5) as well as fragments from other integrin-binding substrates. For instance, a tumor may be treated conventionally with surgery, radiation or chemiotherapy and the modified MMPI molecules of the invention to extend the dormancy of micrometastasis and to inhibit the growth of any residual primary tumor.

It has also been found that hydroxamic acid MMPIs can inhibit the production of the cytokine tumor necrosis factor (TNF) (Mohler et al., *Nature,* 1994, 370, 218–220; Gearing A J H et al., *Nature* 1994, 370, 555–557; McGeehan G M et al., *Nature* 1994, 370, 558–561). Compounds which inhibit the production or action of TNF are thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatic arthritis, multiple scleroris, radation damage, toxicity following administration of immunosuppressive monoclonal antibodies such as OKT3 or CAMPATH-1 and hyperoxic alveolar injury. Since excessive TNF production has been noted in several diseases or conditions also characterized by MMP-mediated tissue degradation, compounds which inhibit both MMPs and TNF production may have particular advantages in the treatment or prophylaxis of diseases or conditions in which both mechanisms are involved.

The compounds of the present invention inhibit various enzymes from the matrix metalloproteinase family such as collagenase, which initiates collagen breakdown, stromelysin (protoglycanase), and gelatinase, and hence are useful for the treatment of matrix metallo endoproteinase diseases. There is evidence implicating collagenase as one of the key enzymes in the breakdown of articular cartilage and bone in rheumatoid arthritis (*Arthritis and Rheumatism,* 20, 1231–1239,1977). Potent inhibitors of collagenase and other metalloproteases involved in tissue degradation are useful in the treatment of rheumatoid arthritis and related diseases in which collagenolytic activity is important. Inhibitors of metalloproteases of this type can therefore be used in treating or preventing conditions which involve tissue breakdown; they are therefore useful in the treatment of arthropathy, dermatological conditions, bone resorption, inflammatory diseases and tumour invasion and in the promotion of wound healing. Specifically, compounds of the present invention may be useful in the treatment of osteopenias such as osteoporosis, rheumatoid arthritis, osteoarthritis, periodontitis, gingivitis, corneal ulceration and tumour invasion.

C. Therapeutic Uses of Oxytocin

A conjugated oxytocin may be used to aid lactation and help relax the pelvis prior to birth. It could also be used to prevent post partum uterine hemorrage.

D. Therapeutic Uses of Cholecystokinin (CCK)

A conjugated CCK could be used in diagnostic studies of the gall bladder or in chronic cholecystisis.

E. Therapeutic Uses of Antihypertensive Agents

Antihypertensive agents are used to treat hypertension.

F. Therapeutic Uses of Methylprednisolone

Methylprednisolone is used to treat a wide range of disorders such as asthma and arthritis. In gastroenterology, it is effective in the treatment of several inflammatory conditions such as ulcerative and microscopic colitis, Crohn's disease and autoimmune hepatitis. A newer usage is for reduction of post-traumatic spinal cord edema.

G. Therapeutic Uses of GP-41 Peptides

GP-41, an HIV transmembrane protein, can be used to create therapeutic and diagnostic agents against HIV. For example, antibodies can be constructed to recognize epitopes of gp41. The structure of this antibody will provide important information regarding antibody/antigen interaction, guide chemists in the selection of superior antigenic peptides for HIV detection, and will provide important information for future recombinant experiments with genetically engineered antibodies.

H. Therapeutic Uses of Blood Brain Barrier (BBB) Peptides

As BBB peptides can traverse the blood brain barrier through protein transduction, these peptides can be covalently linked to compounds, peptides, antisense peptide nucleic acids or 40-nm iron beads, or as in-frame fusions with full-length proteins, to allows these compounds to enter any cell type in a receptor- and transporter-independent fashion. This effectively delivers these compounds past the blood brain barrier.

I. Therapeutic Uses of Modified Cell Adhesion (RGD) peptides

The RGD peptides of the invention and their derivatives and analogs find multiple uses including use as a treatment for neoplastic diseases and inflammatory diseases such as rheumatoid arthritis, lupus.

1. Anti-neoplastic Treatments

The modified cell adhesion peptides of the invention or their derivatives or analogs generally will target directly to cancer cells via peptide-specific receptors. It has been shown that receptors for these peptides are expressed at elevated levels on the surface of tumor cells. Thus, the modified peptides or their derivatives or analogs can be used to preferentially target drugs to metastatic tumor cells. Therefore, the modified cell adhesion peptides or their derivatives or analogs are useful as agents for the treatment of different types of cancers such as breast carcinoma, melanoma, and fibrosarcoma.

The use of an effective amount of modified cell adhesion peptides or their derivatives or analogs as a treatment for cancer has the advantage of being more potent than non modified cell adhesion peptides. Since the modified cell adhesion peptides or their derivatives or analogs are more stable in vivo, smaller amounts of the molecule can be administered for effective treatment.

The derivatives and conjugates of the modified cell adhesion peptides and their analogs may be used in several different ways and to achieve several different ends. As mentioned above, these materials may be used in place of typical cell adhesion peptide drugs as an anti-adhesive agent. As compared with cell adhesion peptide drugs currently available, the materials of this invention can reduce clot formation with less side effects and are available for reducing clot formation for a substantially longer time than conventionally administered cell adhesion peptide drugs. In addition, the derivatized cell adhesion peptides of this invention may be utilized (in accordance with U.S. Pat. Nos. 5,443,827; 5,439,88 and 5,433,940 and PCT application number WO/97/01093 which are hereby incorporated by reference) in conjunction with various other anti-adhesive or anti-cancer therapies. Such anti-cancer therapies include the use of radiation or treatment with antineoplastic agents such as, for example, vinca alkaloids, alkylating agents, doxorubicin, etoposide, methotrexate, tamoxifen, vinblastine, asparaginase, biclutamide, bleomycin, carboplatin, carmustine, chlorambucil, cisplatin, cladribine, cyclophosphamide, cytarabine, dacarbazine, dactinomycin, daunorubisin, docetaxel, floxuridine, fludarabine, fluorouracil, gemcitabine, hydroxyurea, idarubicin, ifosfamide, interferon alpha, irnotecan, leuprolide, mechlorethamine, megestrol, melphalan, mercaptopurine, mitomycin, mitoxantrone, paclitaxel, plicamycin, porfirmer, procarbazine, streptozocin, teniposide, thioguanine, thiotepa, topotecan, trastuzumab, vincristine, vinorelbine, and the like.

The present invention also provides for a method for treating cancer in an individual, wherein said method comprises providing an amount of modified cell adhesion peptide sufficient to treat cancer; where the composition contains a modified cell adhesion peptide.

2. Treatment of Inflammatory Disease

The modified cell adhesion peptides of the invention and their derivatives and analogs also find use as antiinflammatories. In one aspect of the invention, there is provided a method of treating a mammalian subject with an abnormality resulting in increased inflammation of the joints or tissues using the modified cell adhesion peptides of the invention or their derivatives or analogs. The method comprises administering a modified cell adhesion peptide or its derivative or analog to the subject in an amount sufficient to produce an anti-inflammatory effect on the subject. The modified cell adhesion peptide may be administered intracerebroventricularly, orally, subcutaneously, intramuscularly, or intravenously.

The peptides of the present invention, their derivatives, analogs, and conjugates can be used to treat acute or chronic inflammatory disorders involving ischemia, infection, tissue swelling, and/or bone and cartilage degradation. Inflammatory disease refers to a condition in which activation of leukocytes leads to an impairment of normal physiologic function. Examples of such conditions include acute and chronic inflammation such as osteoarthritis, sepsis, ARDS, immune and autoimmune disorders, rheumatoid arthritis, IBD (inflammatory bowel disease), lupus, MS, graft rejection, cirrhosis, sarcoidosis, granulomatous lesions, periodontitis/gingivitis, graft-vs.-host disease, contact dermatitis, and the like. Included among autoimmune disorders which may be treated using the present method are chronic active hepatitis, Graves' disease, insulin-dependent diabetes mellitus (type I), and Hasshimoto's thyroiditis. Included among inflammatory disorders which may be treated using the present method are inflammatory brain disease, inflammatory demyelinating disease, inflammatory vasculitis, inflammatory myopathies, osteomyelitis, Crohn's disease and interstitial cystitis. Additional examples of inflammatory diseases include myocardial diseases, infectious diseases, pulmonary diseases and graft rejection.

J. Therapeutic Uses of Modified Insulinotropic Peptides such as GLP-1

The modified insulinotropic peptides (ITPs) such as GLP-1 of the invention find multiple uses including use as a treatment for diabetes, a sedative, a treatment of nervous system disorders, use to induce an anxiolytic effect on the CNS, use to activate the CNS, use for post surgery treatment and as a treatment for insulin resistance.

1. Diabetes Treatments

The modified ITPs of the invention generally will normalize hyperglycemia through glucose-dependent, insulin-dependent and insulin-independent mechanisms. As such, the modified ITPs are useful as primary agents for the treatment of type II diabetes mellitus and as adjunctive agents for the treatment of type I diabetes mellitus.

The use of an effective amount of modified ITPs as a treatment for diabetes mellitus has the advantage of being more potent than non modified ITPs. Since the modified ITPs are move stable in vivo, smaller amounts of the molecule can be administered for effective tratment. The present invention is especially suited for the treatment of patients with diabetes, both type I and type II, in that the action of the peptide is dependent on the glucose concentration of the blood, and thus the risk of hypoglycemic side effects are greatly reduced over the risks in using current methods of treatment.

The present invention also provides for a method for treating diabetes mellitus in an individual, wherein said method comprises providing an amount of modified ITP sufficient to treat diabetes; where the composition contains a modified ITP.

2. Treatment of Nervous System Disorders

The modified ITPs of the invention also find use as a sedative. In one aspect of the invention. there is provided a method of sedating a mammalian subject with an abnormality resulting in increased activation of the central or peripheral nervous system using the modified ITPs of the invention. The method comprises administering a modified ITP to the subject in an amount sufficient to produce a sedative or anxiolytic effect on the subject. The modified ITP may be administered intracerebroventricularly, orally, subcutaneously, intramuscularly, or intravenously. Such methods are useful to treat or ameliorate nervous system conditions such as anxiety, movement disorder, aggression, psychosis, seizures, panic attacks, hysteria and sleep disorders.

In a related aspect, the invention encompasses a method of increasing the activity of a mammalian subject, comprising administering a modified ITP to the subject in an amount sufficient to produce an activating effect on the subject. Preferably, the subject has a condition resulting in decreased activation of the central or peripheral nervous system. The modified ITPs find particular use in the treatment or amelioration of depression, schizoaffective disorders, sleep apnea, attention deficit syndromes with poor concentration, memory loss, forgetfulness, and narcolepsy, to name just a few conditions in which arousal of the central nervous system may be advantageous.

The modified ITPs of the invention may be used to induce arousal for the treatment or amelioration of depression, schizoaffective disorders, sleep apnea, attention deficit syndromes with poor concentration, memory loss, forgetfulness, and narcolepsy. The therapeutic efficacy of the modified ITP treatment may be monitored by patient interview to assess their condition, by psychological/neurological testing, or by amelioration of the symptoms associated with these conditions. For example, treatment of narcolepsy may be assessed by monitoring the occurrence of narcoleptic attacks. As another example, effects of modified ITPs on the ability of a subject to concentrate, or on memory capacity, may be tested using any of a number of diagnostic tests well known to those of skill in art.

3. Post Surgery Treatment

The modified ITPs of the invention may be utilized for post surgery treatments. A patient is in need of the modified ITPs of the present invention for about 1–16 hours before surgery is performed on the patient, during surgery on the patient, and after the patient's surgery for a period of not more than about 5 days.

The modified ITPs of the present invention are administered from about sixteen hours to about one hour before surgery begins. The length of time before surgery when the compounds used in the present invention should be administered in order to reduce catabolic effects and insulin resistance is dependent on a number of factors. These factors are generally known to the physician of ordinary skill, and include, most importantly, whether the patient is fasted or supplied with a glucose infusion or beverage, or some other form of sustenance during the preparatory period before surgery. Other important factors include the patient's sex, weight and age, the severity of any inability to regulate blood glucose, the underlying causes of any inability to regulate blood glucose, the expected severity of the trauma caused by the surgery, the route of administration and bioavailability, the persistence in the body, the formulation, and the potency of the compound administered. A preferred time interval within which to begin administration of the modified ITPs used in the present invention is from about one hour to about ten hours before surgery begins. The most preferred interval to begin administration is between two hours and eight hours before surgery begins.

Insulin resistance following a particular type of surgery, elective abdominal surgery, is most profound on the first post-operative day, lasts at least five days, and may take up to three weeks to normalize Thus, the post-operative patient may be in need of administration of the modified ITPs used in the present invention for a period of time following the trauma of surgery that will depend on factors that the physician of ordinary skill will comprehend and determine. Among these factors are whether the patient is fasted or supplied with a glucose infusion or beverage, or some other form of sustenance following surgery, and also, without limitation, the patient's sex, weight and age, the severity of any inability to regulate blood glucose, the underlying causes of any inability to regulate blood glucose, the actual severity of the trauma caused by the surgery, the route of administration and bioavailability, the persistence in the body, the formulation, and the potency of the compound administered. The preferred duration of administration of the compounds used in the present invention is not more than five days following surgery.

4. Insulin Resistance Treatment

The modified ITPs of the invention may be utilized to treat insulin resistance independently from their use in post surgery treatment. Insulin resistance may be due to a decrease in binding of insulin to cell-surface receptors, or to alterations in intracellular metabolism. The first type, characterized as a decrease in insulin sensitivity, can typically be overcome by increased insulin concentration. The second type, characterized as a decrease in insulin responsiveness, cannot be overcome by large quantities of insulin. Insulin resistance following trauma can be overcome by doses of insulin that are proportional to the degree of insulin resistance, and thus is apparently caused by a decrease in insulin sensitivity.

The dose of modified ITPs effective to normalize a patient's blood glucose level will depend on a number of factors, among which are included, without limitation, the patient's sex, weight and age, the severity of inability to regulate blood glucose, the underlying causes of inability to regulate blood glucose, whether glucose, or another carbohydrate source, is simultaneously administered, the route of administration and bioavailability, the persistence in the body, the formulation, and the potency.

K. Therapeutic Uses of Modified Krincile 5 Peptides

As described earlier, angiogenesis includes a variety of processes involving neovascularization of a tissue including "sprouting", vasculogenesis, or vessel enlargement. With the exception of traumatic wound healing, corpus leuteum formation and embryogenesis, it is believed that the majority of angiogenesis processes are associated with disease processes and therefore the use of the present therapeutic methods are selective for the disease and do not have deleterious side effects.

There are a variety of diseases in which angiogenesis is believed to be important, which may be treatable with the modified peptides of the invention. These diseases include, but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

The modified kringle 5 peptides of the invention find use in methods which inhibit angiogenesis in a diseased tissue ameliorates symptoms of the disease and, depending upon the disease, can contribute to cure of the disease. The modified peptides of the invention are more stable in vivo and, as such, smaller amounts of the modified peptide can be administered for effective treatment In one embodiment, the invention contemplates inhibition of angiogenesis, per se, in a tissue. The extent of angiogenesis in a tissue, and therefore the extent of inhibition achieved by the present methods, can be evaluated by a variety of method, for detecting $\forall_5\#_3$-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

In one related embodiment, a tissue to be treated with the modified kringle 5 peptides of the invention is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient." In this context, a mammal is understood to include any mammalian species in which treatment of diseases associated with angiogenesis is desirable, particularly agricultural and domestic mammalian species.

In another related embodiment, a tissue to be treated with the modified kringle 5 peptides of the invention is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated with the modified kringle 5 peptides of the invention is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

The present invention thus provides for a method of inhibiting tumor neovascularization by inhibiting tumor angiogenesis according to the present methods using the modified kringle 5 peptides of the invention. Similarly, the invention provides a method of inhibiting tumor growth by practicing the angiogenesis-inhibiting methods. The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of the modified kringle 5 peptides of the invention is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the modified kringle 5 peptides after surgery where solid tumors have been removed as a prophylaxis against metastases. Insofar as the present methods apply to inhibition of tumor neovascularization, the methods can also apply to inhibition of tumor tissue growth, to inhibition of tumor metastases formation, and to regression of established tumors using the modified kringle 5 peptides of the invention.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the modified kringle 5 peptides of the present invention. Therefore, the invention also contemplates inhibition of restenosis by inhibiting angiogenesis in a patient following angioplasty procedures. For inhibition of restenosis, the modified kringle 5 peptide is typically administered after the angioplasty procedure for from about 2 to about 28 days, and more typically for about the first 14 days following the procedure.

The present method for inhibiting angiogenesis in a tissue comprises contacting a tissue in which angiogenesis is occurring, or is at risk for occurring, with a composition comprising a therapeutically effective amount of a modified kringle 5 peptide. The dosage ranges for the administration of the modified kringle 5 peptide depend upon the form of the peptide, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

As angiogenesis inhibitors, such modified kringle 5 peptides are useful in the treatment of both primary and metastatic solid tumors and carcinomas of the breast; colon; rectum; lung; oropharynx; hypopharynx; esophagus, stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas; prophylaxis of autoimmune diseases including rheumatoid, immune and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids) and diseases which have angiogenesis as a pathologic consequence including cat scratch disease (Rochele minalia quintosa) and ulcers (Helicobacter pylori). Another use is as a birth control agent which inhibits ovulation and establishment of the placenta.

The modified kringle 5 peptides of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, the modified kringle 5 peptides of the present invention may be administered with chemotherapeutic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. For example, a tumor may be treated conventionally with surgery, radiation or chemotherapy and kringle 5 administration with subsequent kringle 5 administration to extend the dormancy of micrometastases and to stabilize and inhibit the growth of any residual primary tumor.

L. Therapeutic Uses of Modified Opioid Molecules and Analgesic Agents

The derivatives and conjugates of the opioid molecules and analgesic agents may be used in several different ways and to achieve several different ends. These materials may be used in place of typical antinociceptive agents for alleviating pain. As compared with drugs currently available, the materials of this invention can alleviate pain without central mediated side effects or potential of addiction or loss of efficacy, and are available for alleviating pain for a substantially longer time than conventionally administered drugs. Opioid derivatives and conjugates of this invention also may be utilized (in accordance with U.S. Pat. No. 5,482,930) as anti-inflammatory and/or anti-irritation agents or in general to inhibit vascular leakage from tissues. In addition, as is known in the art, these materials may be used to treat hosts which are or have become tolerant to morphine (or to treat patients undergoing methadone treatment programs), as well as treatment of narcotics withdrawal in general.

M. Therapeutic Uses of Modified Immuno-suppressants

A variety of immuno-suppressant agents such as cyclosporin and derivatives, corticosteroids, sulfasalazine, thalidomide, methotrexate, OKT3, peptide-T, or agents that inhibit T-cell activation or adhesion would be useful to prior to transplantation to mask immune responsiveness and organ rejection. Such agents could be applied at the time of tissue harvest (e.g. heart, lung, liver harvest) or immediately prior to restitution of blood flow in the recipient. Such immuno-suppressant agents would prevent the recognition of foreign antigen from the donor tissue that would facilitate short term acceptance and facilitate longer term ability for the host to accommodate the transplanted organ.

N. Therapeutic Uses of Modified Antibiotics:

The modified antibiotics of the invention find use in treating infections.

O. Therapeutic Uses of Modified Antidepressants

The modified antidepressants of the invention are useful for treating depression.

P. Therapeutic Uses of Modified Anti-Viral and Anti-Fusogenic Peptides HIV and anti-HIV peptides:

The human immunodeficiency virus (HIV), which is responsible for acquired immune deficiency syndrome (AIDS), is a member of the lentivirus family of retroviruses. There are two prevalent types of HIV, HIV-1 and HIV-2, with various strain of each having been identified. HIV targets CD-4+ cells, and viral entry depends on binding of the HIV protein gp41 to CD4+ cell surface receptors.

Modified anti-viral or anti-fusogenic peptides of the invention may be used as a therapeutic agent in the treatment of patients who are suffering from HIV infection, and can be administered to patients according to the methods described below and other methods known in the art. Effective therapeutic dosages of the modified peptides may be determined through procedures well known by those in the art and will take into consideration any concerns over potential toxicity of the peptide.

The modified peptides can also be administered prophylactically to previously uninfected individuals. This can be advantageous in cases where an individual has been subjected to a high risk of exposure to a virus, as can occur when individual has been in contact with an infected individual where there is a high risk of viral transmission. This can be expecially advantageous where there is no known cure for the virus, such as the HIV virus. As a example, prophylactic administration of a modified anti-HIV peptide would be advantageous in a situation where a health care worker has been exposed to blood from an HIV-infected individual, or in other situations where an individual engaged in high-risk activities that potentially expose that individual to the HIV virus.

1. SIV and anti-SIV peptides:

Simian immunodeficiency viruses (SIV) are lentiviruses that cause acquired immunodeficiency syndrome (AIDS)-like illnesses in susceptible monkeys. Modified anti-viral peptides according to the invention can be used for the treatment of infected animals or as a prophylactic in a similar fashion as for HIV.

2. RSV:

Respiratory syncytial virus (RSV) is a respiratory pathogen, especially dangerous in infants and small children where it can cause bronchiolitis (inflammation of the small air passages) and pneumonia. RSVs are negative sense, single stranded RNA viruses and are members of the Paramyxoviridae family of viruses. The route of infection of RSV is typically through the mucous membranes by the respiratory tract, i.e., nose, throat, windpipe and bronchi and bronchioles. Antiviral peptides according to the invention can be used for prevention and treatment of RSV related diseases.

3. HPV:

Human parainfluenza virus (HPIV or HPV), like RSV, is another leading cause of respiratory tract disease, and like RSVs, are negative sense, single stranded RNA viruses that are members of the Paramyxoviridae family of viruses. There are four recognized serotypes of HPIV—HPIV-1, HPIV-2, HPIV-3 and HPIV-4. HPIV-1 is the leading cause of croup in children, and both HPIV-1 and HPIV-2 cause upper and lower respiratory tract illnesses. HPIV-3 is more often associated with bronchiolitis and pneumonia. Antiviral peptides according to the invention can be used for treatment of HPV related diseases.

4. MeV:

Measles virus (MV or MeV) is an enveloped negative, single-stranded RNA virus belonging to the Paramyxoviridae family of viruses. Like RSV and HPV, MeV causes respiratory disease, and also produces an immunosuppression responsible for additional, opportunistic infections. In some cases, MeV can establish infection of the brain leading to severe neurlogical complications. Antiviral peptides according to the invention can be used for treatment of RSV related diseases.

Q. Therapeutic Uses of Modified Antihistamine Agents

Modified anthistamine agents find use in treating excess histamine formed in body tissues including allergic reactions.

R. Therapeutic Uses of Modified Anti-angina Agents

Modified anthi-angina agents find use in treating angina including treatment of choking and suffocating sensations.

Angina results from insufficient blood supply to the heart, and is often caused by blockages in the arteries that feed the heart muscle with blood (coronary artery stenoses due to atherosclerosis). "Unstable" angina conditions, can develop into acute coronary syndromes (ACS), including myocardial infarction. Antianginal therapies include treatment with nitroglycerin and the use of aspirin and heparin.

Platelet activation and aggregation play an important and essential role in the formation of intracoronary thrombus in acute coronary syndromes (ACS). Glycoprotein IIb/IIIa receptor inhibitors are currently used in connection with heparin and aspirin in ACS. Glycoprotein IIb/IIIa receptor inhibitors block the final step for platelet aggregation and fibrinogen binding, thus preventing thrombus formation. Tirofiban is a potent, synthetic, non-peptide and specific glycoprotein IIb/IIIa receptor inhibitor and has shown to be well tolerated and to reduce the risk of ischaemic complications in patients with unstable angina, non-Q-wave myocardial infarction and high-risk patients undergoing revascularisation when used in combination with aspirin and heparin. Other GP IIb/IIIa receptor inhibitors include abciximab and eptifibatide.

S. Use of Modified Thyroxine Molecules

Thyroxine, an amino acid of the thyroid gland (Merck Index, 1989, 9348:1483) and thyroxine analogues are well-known in the art. It is well established in the literature that thyroid hormones, specifically thyroxines T3 and T4, have two distinct types of biological actions: one on cell metabolism, the second on cell differentiation and development (Jorgensen, 1978, "Thyroid Hormones and Analogues II. Structure-Activity Relationships," In: Hormonal Proteins and Peptides, Vol. VI, pp. 107–204, C. H. Li, ed., Academic Press, New York). For example, thyroxine suppresses uptake of iodine by the thyroid (Money et al., 1959, "The Effect of Various Thyroxine Analogues on Suppression of Iocline-131 Uptake by the Rat Thyroid," Endocrinology 64:123–125) and induces cell differentiation as studied by tadpole metamorphosis (Money et al., 1958, "The Effect of Change in Chemical Structure of Some Thyroxine Analogues on the Metamorphosis of Rana Pipiens Tadpoles," Endocrinology 63:20–28). Additionally, thyroxine and certain thyroxine analogues depress growth of non-malignant mouse pituitary thyrotropic tumors (Kumaoka et al., 1960, "The Effect of Thyroxine Analogues on a Transplantable Mouse Pituitary Tumor," Endocrinology 66:32–38; Grinberg et al., 1962, "Studies with Mouse Pituitary Thyrotropic Tumors. V. Effect of Various Thyroxine Analogs on Growth and Secretion," Cancer Research 22:835–841).

The structural requirements of thyroxine and thyroxine analogues for metabolic stimulation and induction of cell differentiation are not identical (see Jorgensen, 1978, "Thyroid Hormones and Analogues II. Structure-Activity Relationships," In: Hormonal Proteins and Peptides, Vol. VI, p. 150, C. H. Li, ed., Academic Press, New York). For example, Money et al. have found that there is no correlation between suppression of thyroid iodine uptake and induction of tadpole metamorphosis (Money et al., 1958, "The Effect of Change in Chemical Structure of Some Thyroxine Analogues on the Metamorphosis of Rana Pipiens Tadpoles," Endocrinology 63:20–28). Based on these observations, it was conceived that as yet unidentified cellular responses may be altered or induced by certain thyroxine analogues which do not exhibit either mode of action (metabolic or differentiating) exhibited by thyroxine T3 and T4.

Deficiency of thyroid activity, whether occurring spontaneously or resulting from surgical removal of thyroid gland, thyroiditis, or decreased function secondary to pituitary degeneration results in clinical hypothyroidism. Whatever the cause, the symptom is treated by replacement therapy using the modified thyroxine molecules of the invention.

The present invention also relates to a method for the treatment of anemia which is associated with rheumatoid arthritis and of the anemia present in patients having a viral or bacterial infection wherein symptoms of rheumatoid arthritis are additionally present using the modified thyroxine molecules of the invention. According to the invention, the associated anemia which is characterized as being moderately hypochromic and normocytic is treated by administering to a patient in need of treatment a composition for increasing the thyroxine in the blood stream and thereby increasing the ceiling on the number of red cells maturing from the stem cells in the blood stream. The composition can include the presence of an anti-inflammatory agent so as to treat the inflammation present and reduce any pain.

T. Use of Modified Bronchodialators and Anti-Asthmatic Agents

Anti-asthmatic agents find use in the treatment of asthma and other lung diseases. Such anti-asthmatic agents include, bronchodialators like albuterol (Proventil or Ventolin) and maleimidoethyl-1 theobromineacetamide.

U. Uses of Modified Diagnostic Agents

The diagnostic agent employed and the vascular protein or proteins targeted will depend upon whether one wishes to diagnostically image the anatomic compartment over an extended period of time, whether one wishes to preferentially image only a specific cell type or compartment, or both. Applications for covalently bonding a diagnostic agent of interest to a long-lived vascular protein for diagnostic imaging of the vascular space over an extended period of time are numerous and include enhancing the ability to detect abnormalities in blood flow throughout the entire mammalian vascular system, including the detection of internal injury causing abnormal bleeding or, alternatively, the presence of thromboses. For example, one may wish to image the vascular space over an extended period of time to detect the effects of a particular treatment while they occur, i.e., detecting the disappearance of an embolism, the stoppage of internal bleeding, or the like.

Diagnostically imaging the vascular space over an extended period of time also allows for the detection of various diseases associated with the vascular system, i.e., such as arterial blockage in the heart. Thus, diagnostically imaging the vascular system over an extended period of time may be employed to non-invasively detect a consistently reduced blood flow to the heart. Such a method also provides a means for quantitatively measuring cardiac efficiency and ventricular output volume over an extended period of time, i.e., during extended periods of exercise, or the like.

Other applications for such a method arise from the ability to non-invasively visualize anatomical structures of the mammalian vascular system and the effects on those anatomical structures over time of the administration of various drugs, such as vasodilators, vasoconstrictors, or the like. Such may allow for the early detection of developmental vascular abnormalities, injuries, or the like.

Additional applications arising from the ability to diagnostically image the vascular space over an extended period of time include functional assessment of the cardiovascular system as routinely utilized in nuclear medicine for single measurements.

Applications for preferentially bonding a diagnostic agent of interest to a specific protein or proteins present in the vascular system so as to diagnostically image only a specific cell type or compartment are also numerous. For example, having the ability to preferentially direct a diagnostic. agent of interest to a specific cell type in the vascular system can allow for the non-invasive and early detection of lesions or various tumors associated with the mammalian vascular system by directing the bifunctional anchor molecule to a tumor specific cell surface protein.

Additionally, diagnostic agents can be directed to cell surface proteins of specific cell types predominantly associated with specific anatomic compartments, allowing one to preferentially diagnostically image such compartments as lymph nodes, Peyer's patches, kidney glomeruli, liver, pancreas, tonsil, or any other organ to which mobile cells in the vasculature will migrate.

Other applications for preferentially diagnostic imaging a specific cell type or compartment of the vascular system include diagnosis and treatment of stenosis or plaque, vascular shunt reendothelialization or shunt failure due to tissue growths, or organ rejection due to tissue migration.

The diagnostic agents of the invetion may be delivered to a local site via a local delivery device. Delivery devices include catheters, syringes, trocars and endoscopes. Delivery of the agent to a local site allows imaging of the specific area of delivery. The agents that find particular use in localized delivery are the non-specific diagnostic agents such as NHS-derivatives.

The invention can be more clearly illustrated by the following non-limiting examples.

EXAMPLE 1

Preparation of Modified RGD Peptide AGYKPEGKRGDAK

RGD peptide AGYKPEGKRGDAK (SEQ ID NO:1) was synthesized and modified to include a linking group and a maleimide group according to the synthesis scheme set forth below.

Solid phase peptide synthesis on a 100 µmole scale was performed using manual solid-phase synthesis, a Symphony Peptide Synthesizer and Fmoc protected Ramage Resin. The following protected amino acids were sequentially added to resin: Fmoc-Lys(Boc)-OH, Fmoc-Ala-OH, Fmoc-Asp(tBu)-OH, Fmoc-Gly-OH, Fmoc-Arg(Pbf)-OH, Fmoc-Lys(Boc)-OH, Fmoc-Gly-OH, Fmoc-Glu(tBu)-OH, Fmoc-Asp(tBu)-OH, Fmoc-Pro-OH, Fmoc-Lys(Boc)-OH, Fmoc-Tyr(tBu)-OH, Fmoc-Gly-OH, Fmoc-Ala-OH. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). In last elongation step, the synthesis was then re-automated for the addition of the 3-maleimidopropionic acid (Step 2). Between every coupling, the resin was washed 3 times with N,N-dimethyltormamide (DMF) and 3 times with isopropanol. The peptide was cleaved from the resin using 85% TFA/5% TIS/5% thioanisole and 5% phenol, followed by precipitation by dry-ice cold $Et_2O$ (Step 3). The product was purified by preparative reversed phased HPLC using a Varian (Rainin) preparative binary HPLC system: gradient elution of 30–55% B (0.045% TFA in $H_2O$ (A) and 0.045% TFA in $CH_3CN$ (B)) over 180 min at 9.5 mL/min using a Phenomenex Luna 10µ phenyl-hexyl, 21 mm×25 cm column and UV detector (Varian Dynamax UVD II) at λ214 and 254 nm to afford the desired molecule in >95% purity, as determined by RP-HPLC.

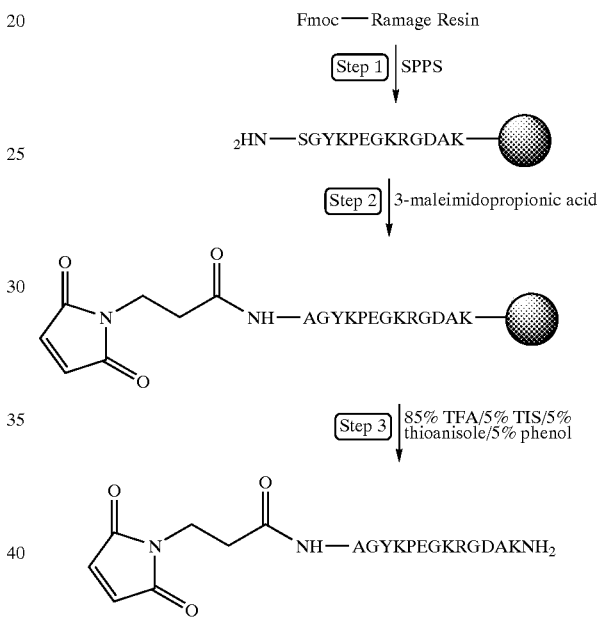

EXAMPLE 2

Preparation of Modified RGD Peptide KRGDACEGDSGGPFC

RGD peptide KRGDACEGDSGGPFC (SEQ ID NO:2) was synthesized and modified to include a linking group and a maleimide group according to the synthesis scheme set forth below.

Solid phase peptide synthesis on a 100 µmole scale was performed using manual solid-phase synthesis, a Symphony Peptide Synthesizer and Fmoc protected Ramage Resin. The following protected amino acids were sequentially added to resin: Fmoc-Cys(Acm)-OH (C), Fmoc-Phe-OH, Fmoc-Pro-OH, Fmoc-Gly-OH, Fmoc-Gly-OH, Fmoc-Ser(tBu)-OH, Fmoc-Asp(tBu)-OH, Fmoc-Gly-OH, Fmoc-Glu(tBu)-OH, Fmoc-Cys(Acm)-OH (C), Fmoc-Ala-OH, Fmoc-Asp(tBu)-OH, Fmoc-Gly-OH, Fmoc-Arg(Pbf)-OH, Fmoc-Lys(Boc)-OH They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). C are cyclized cysteine. The cyclisation was achieved by ,cyclization by treatment with Tl(TFA)₃ (3 equiv. on 175 ummol scale) when the coupling was paused at last lysine residue (step 2). After cyclization, In last elongation step, the synthesis was then re-automated for the addition of the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et₂O (Step 4). The product was purified by preparative reversed phased HPLC using a Varian (Rainin) preparative binary HPLC system: gradient elution of 30–55% B (0.045% TFA in H₂O (A) and 0.045% TFA in CH₃CN (B)) over 180 min at 9.5 mumin using a Phenomenex Luna 10μ phenyl-hexyl, 21 mm×25 cm column and UV detector (Varian Dynamax UVD II) at λ214 and 254 nm to afford the desired protein in >95% purity, as determined by RP-HPLC.

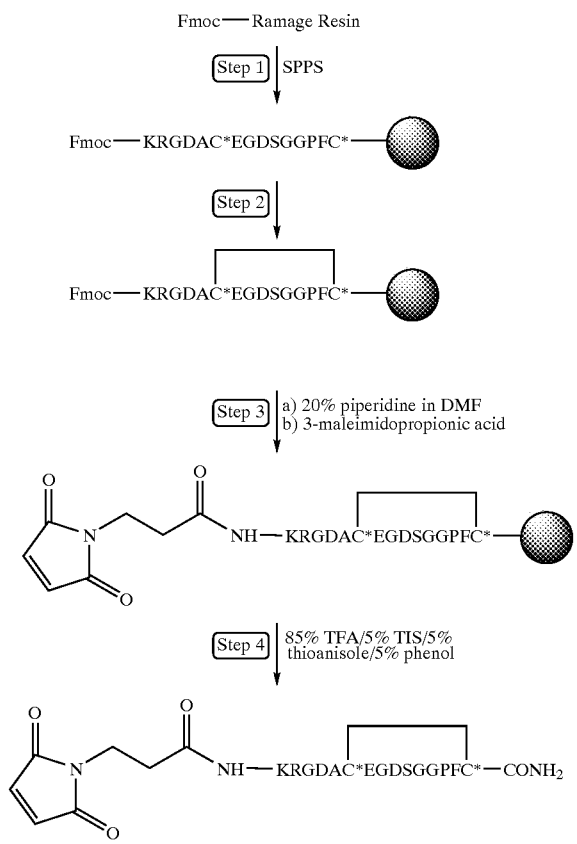

EXAMPLE 3

Preparation of Modified RGD Peptide KRGDACEGDSFFPFC

RGD peptide KRGDACEGDSFFPFC (SEQ ID NO:3) was synthesized and modified to include a linking group and a maleimide group according to the synthesis scheme set forth below.

Solid phase peptide synthesis on a 100 μmole scale was performed using manual solid-phase synthesis, a Symphony Peptide Synthesizer and Fmoc protected Ramage Resin. The following protected amino acids were sequentially added to resin: Fmoc-Cys(Acm)-OH (C), Fmoc-Phe-OH, Fmoc-Pro-OH, Fmoc-Gly-OH, Fmoc-Gly-OH, Fmoc-Ser(tBu)-OH, Fmoc-Asp(tBu)-OH, Fmoc-Gly-OH, Fmoc-Glu(tBu)-OH, Fmoc-Cys(Acm)-OH (C), Fmoc-Ala-OH, Fmoc-Asp(tBu)-OH, Fmoc-Gly-OH, Fmoc-Arg(Pbf)-OH, Fmoc-Lys(Boc)-OH, Fmoc-AEEA-OH, Fmoc-AEEA-OH, They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). C are cyclized cysteine. The cyclisation was achieved by, cyclization by treatment with Tl(TFA)₃ (3 equiv. on 175 ummol scale) when the coupling was paused at last lysine residue (step 2). After cyclization, In last elongation step, the synthesis was then re-automated for the addition of the linking group s and the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et₂O (Step 4). The product was purified by preparative reversed phased HPLC using a Varian (Rainin) preparative binary HPLC system: gradient elution of 30–55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired peptidein >95% purity, as determined by RP-HPLC.

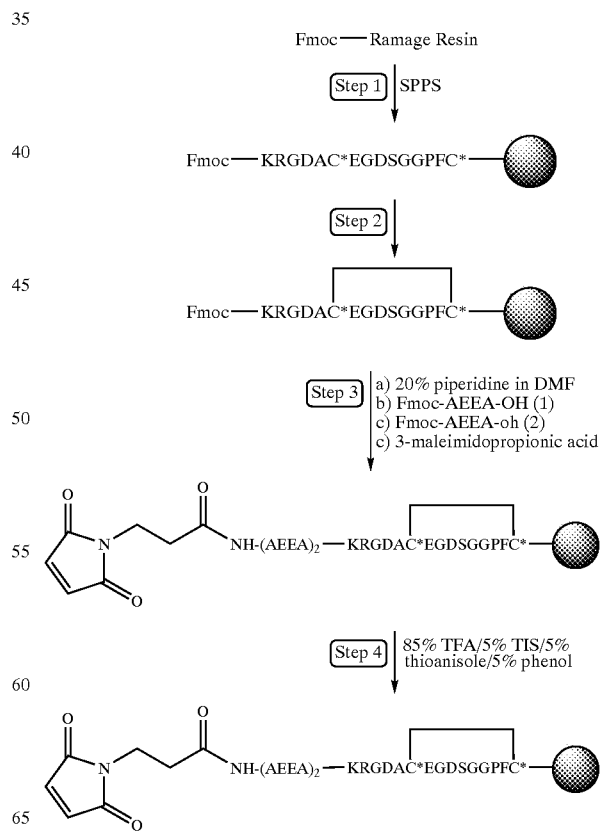

EXAMPLE 4

Preparation of Modified GP-41A Peptide YTSLIHSLIEESQNQQEKNEQELLELDKWASLWNWF

GP-41A peptide YTSLIHSLIEESQNQQEKNEQEL-LELDKWASLWNWF (SEQ ID NO:4) was synthesized and modified to include a linking group and a maleimide group according to the synthesis scheme set forth below.

precipitation by dry-ice cold Et$_2$O (Step 3). The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm to afford the desired molecule in >95% purity, as determined by RP-HPLC.

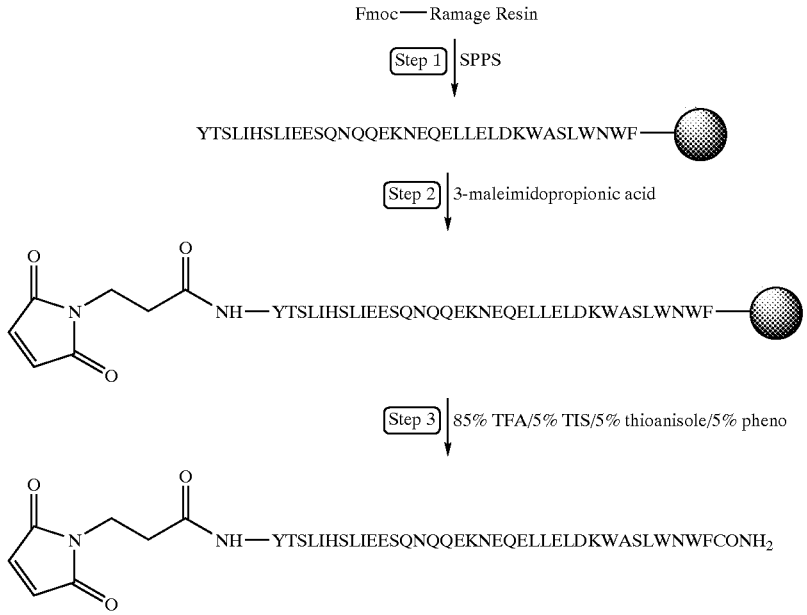

Solid phase peptide synthesis on a 100 µmole scale was performed using manual solid-phase synthesis, a Symphony Peptide Synthesizer and Fmoc protected Ramage Resin. The following protected amino acids were sequentially added to resin: Fmoc-Phe-OH, Fmoc-Trp(Boc)-OH, Fmoc-Asn(Trt)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Boc)-OH, Fmoc-Asp(tBu)-OH, Fmoc-Leu-OH, Fmoc-Glu(tBu)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-His(Boc)-OH, Fmoc-Ile-OH, Fmoc-Leu-OH, Fmoc-Ser(tBu)-OH, Fmoc-Thr(tBu)-OH, Fmoc-Tyr(tBu)-OH. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropyl-ethylamine (DIEA). Removal of the Fmoc protecting group was achieved using a solution of 20% (V/V) piperidine in N,N-dimethylformamide (DMF) for 20 minutes (step 1). In the last elongation step, the synthesis was automated for the addition of the 3-maleimidopropionic acid (Step 2). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by

EXAMPLE 5

Preparation of Modified GP-41 B Peptide YTSLIHSLIEESQNQQEKNEQELLELDK WASLWNWF GP-41B peptide YTSLIHSLIEESQNQQEKNEQEL-LELDKWASLWNWF (SEQ ID NO:5) was synthesized and modified to include a linking group and a maleimide group according to the synthesis scheme set forth below.

Solid phase peptide synthesis on a 100 µmole scale was performed using manual solid-phase synthesis, a Symphony Peptide Synthesizer and Fmoc protected Ramage Resin. The following protected amino acids were sequentially added to resin: Fmoc-Phe-OH, Fmoc-Trp(Boc)-OH, Fmoc-Asn(Trt)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Aloc)-OH, Fmoc-Asp(tBu)-OH, Fmoc-Leu-OH, Fmoc-Glu(tBu)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-His(Boc)-OH, Fmoc-Ile-OH, Fmoc-Leu-OH, Fmoc-Ser(tBu)-OH, Fmoc-Thr(tBu)-OH, Fmoc-Tyr(tBu)-OH.

They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

In the last elongation step, the synthesis was automated for the addition of the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et$_2$O (Step 4). The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

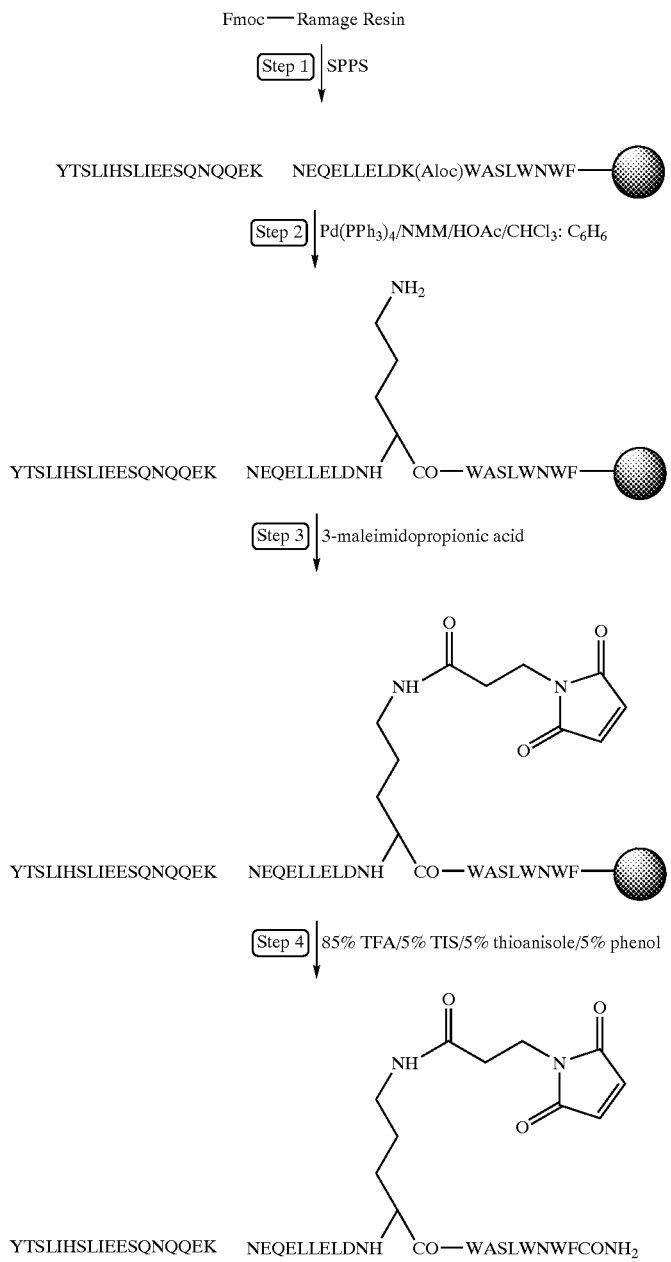

EXAMPLE 6

Preparation of Modified GP-41C Peptide
YTSLIHSLIEESQNQQEKNEQELLELDK
WASLWNWF

GP-41C peptide YTSLIHSLIEESQNQQEKNEQEL-LELDKWASLWNWF (SEQ ID NO:6) was synthesized and modified to include a linking group and a maleimide group according to the synthesis scheme set forth below.

Solid phase peptide synthesis on a 100 μmole scale was performed using manual solid-phase synthesis, a Symphony Peptide Synthesizer and Fmoc protected Ramage Resin. The following protected amino acids were sequentially added to resin: Fmoc-Phe-OH, Fmoc-Trp(Boc)-OH, Fmoc-Asn(Trt)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Aloc)-OH, Fmoc-Asp(tBu)-OH, Fmoc-Leu-OH, Fmoc-Glu(tBu)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-His(Boc)-OH, Fmoc-Ile-OH, Fmoc-Leu-OH, Fmoc-Ser(tBu)-OH, Fmoc-Thr(tBu)-OH, Fmoc-Tyr(tBu)-OH, They were dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

The selective deprotection of the Lys (Aloc) group is performed manually and accomplished by treating the resin with a solution of 3 eq of $Pd(PPh_3)_4$ dissolved in 5 mL of $C_6H_6$ $CHCl_3$ (1:1): 2.5% NMM (v:v): 5% AcOH (v:v) for 2 h (Step 2). The resin is then washed with $CHCl_3$ (6×5 mL), 20% AcOH in DCM (6×5 mL), DCM (6×5 mL), and DMF (6×5 mL).

In the last elongation step, the synthesis was automated for the addition of the Fmoc-AEEA-OH and finally 3-maleimidopropionic acid (Step 2). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold $Et_2O$ (Step 3). The product was purified by preparative reversed phased HPLC using a Varian (Rainin) preparative binary HPLC system: gradient elution of 30–55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

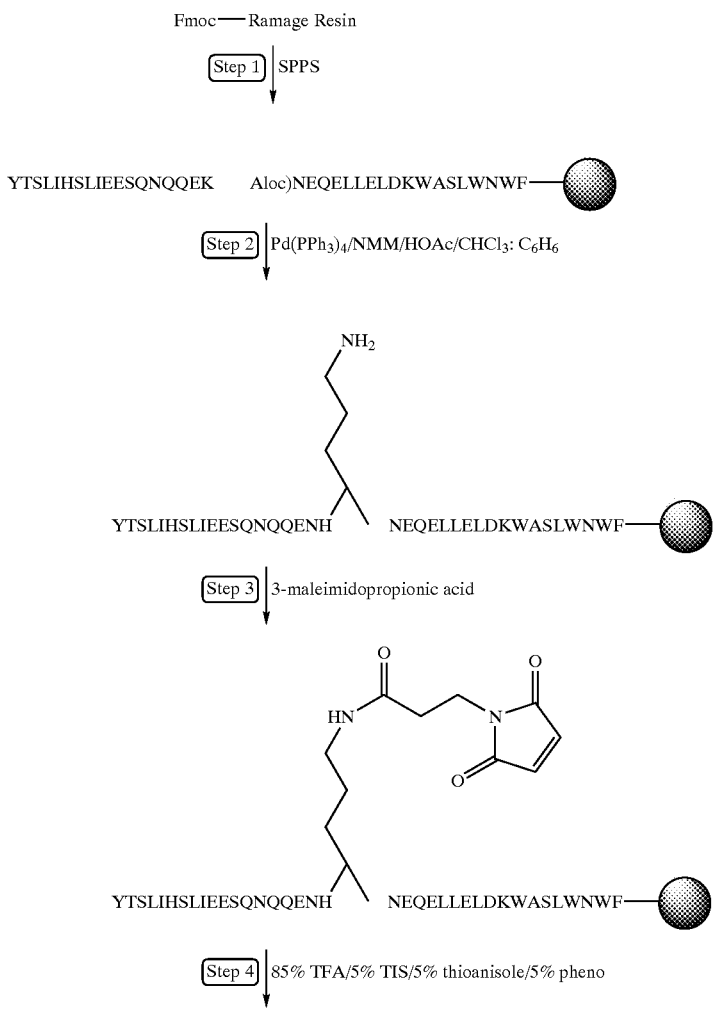

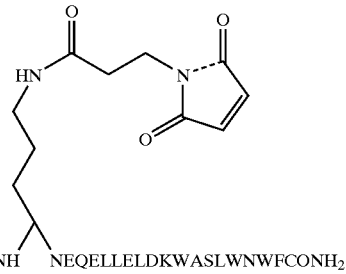

YTSLIHSLIEESQNQQENH    NEQELLELDKWASLWNWFCONH₂

EXAMPLE 7

Preparation of Modified RSV Peptide VYPSDEYDASISQVNEEINQALAYIRKADELLENV

RSV peptide VYPSDEYDASISQVNEEINQALAYIRK-ADELLENV (SEQ ID NO:7) was synthesized and modified to include a linking group and a maleimide group according to the synthesis scheme set forth below.

Solid phase peptide synthesis on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Val-OH, Fmoc-Asn(Trt)-OH, Fmoc-Glu(tBu)-OH, Fmoc-Leu-OH, Fmoc-Leu-OH, Fmoc-Glu(tBu)-OH, Fmoc-Asp(tBu)-OH, Fmoc-Ala-OH, Fmoc-Lys(Boc)-OH, Fmoc-Arg(Pbf)-OH, Fmoc-Ile-OH, Fmoc-Tyr(tBu)-OH, Fmoc-Ala-OH, Fmoc-Leu-OH, Fmoc-Ala-OH, Fmoc-Gln(Trt)-OH, Fmoc-Asn(Trt)-OH, Fmoc-Ile-OH, Fmoc-Glu(tBu)-OH, Fmoc-Glu(tBu)-OH, Fmoc-Asn(Trt)-OH, Fmoc-Val-OH, Fmoc-Gln(Trt)-OH, Fmoc-Ser(tBu)-OH, Fmoc-Ile-OH, Fmoc-Ser(tBu)-OH, Fmoc-Ala-OH, Fmoc-Asp(tBu)-OH, Fmoc-Tyr(tBu)-OH, Fmoc-Glu(tBu)-OH, Fmoc-Asp(tBu)-OH, Fmoc-Ser(tBu)-OH, Fmoc-Pro-OH, Fmoc-Tyr(tBu)-OH, Fmoc-Val-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1).

The amino group of the final amino acid is acetylated using Acetic Acid activated using O-benzotriazol-1-yl-N,N,N',N'-tetramethyl-uronium hexafluorophosphate (HBTU) and Diisopropylethylamine (DIEA). The selective deprotection of the Lys (Aloc) group is performed manually and accomplished by treating the resin with a solution of 3 eq of Pd(PPh₃)₄ dissolved in 5 mL of CHCl₃:NMM:HOAc (18:1:0.5) for 2 h (Step 2). The resin is then washed with CHCl₃ (6×5 mL), 20% HOAc in DCM (6×5 mL), DCM (6×5 mL), and DMF (6×5 mL). The synthesis is then re-automated for the addition of the 3-maleimidopropionic acid (Step 3).

Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et₂O (Step 4). The product is purified by preparative reversed phased HPLC using a Varian (Rainin) preparative binary HPLC system: gradient elution of 30–55% B (0.045% TFA in H₂O (A) and 0.045% TFA in CH₃CN (B) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

Fmoc—Ramage Resin

[Step 1] | SPPS

Ac—VYPSDEYDASISQVNEEINQALAYIRKADELLENV-Aloc)—

[Step 2] | Pd(PPh₃)₄/NMM/HOAc/CHCl₃: C₆H₆

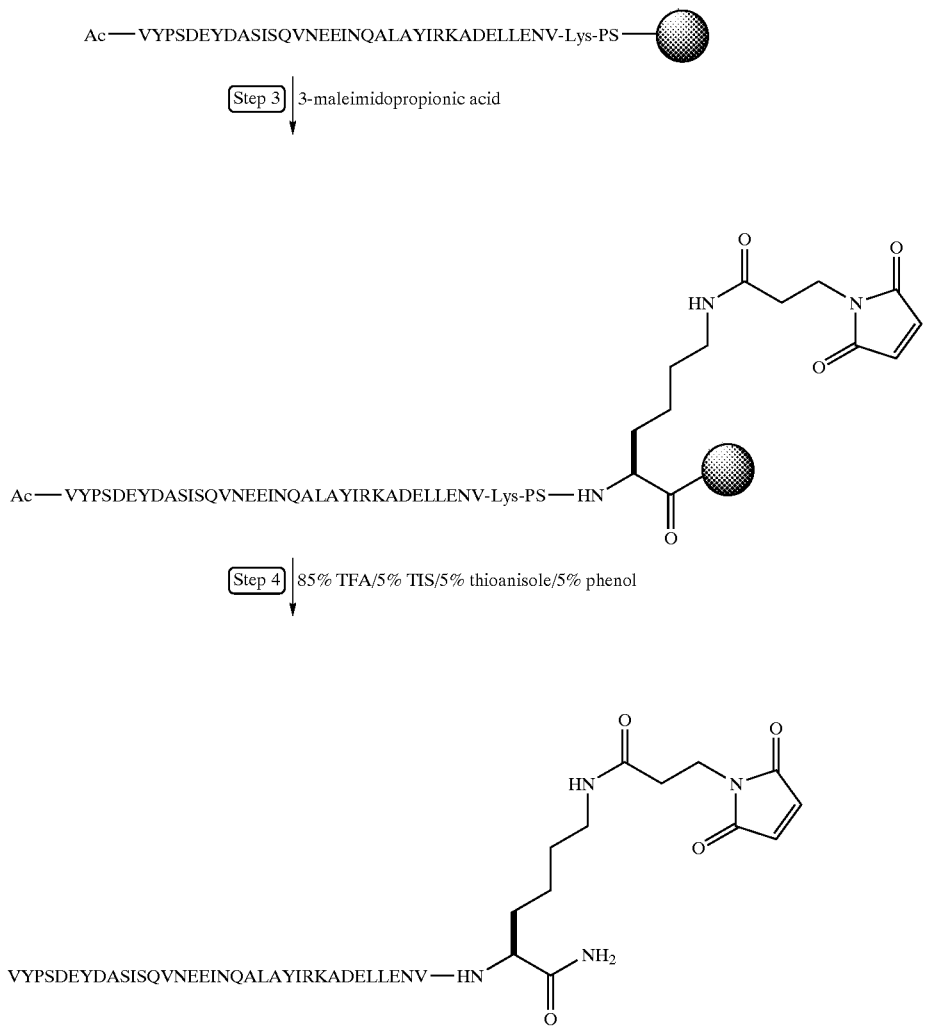

EXAMPLE 8

Preparation of Modified RSV Peptide VYPSDEYDASISQVNEEINQALAYIRKADELLENV

RSV peptide VYPSDEYDASISQVNEEINQALAYIRK-ADELLENV (SEQ ID NO:8) was synthesized and modified to include a linking group and a maleimide group to produce the modified peptide depicted below.

Solid phase peptide synthesis on a 100 μmole scale is performed using manual solid-phase synthesis, a Symphony Peptide Synthesizer and Fmoc protected Rink Amide MBHA. The following protected amino acids are sequentially added to resin: Fmoc-Val-OH, Fmoc-Asn(Trt)-OH, Fmoc-Glu(tBu)-OH, Fmoc-Leu-OH, Fmoc-Leu-OH, Fmoc-Glu(tBu)-OH, Fmoc-Asp(tBu)-OH, Fmoc-Ala-OH, Fmoc-Lys(Boc)-OH, Fmoc-Arg(Pbf)-OH, Fmoc-Ile-OH, Fmoc-Tyr(tBu)-OH, Fmoc-Ala-OH, Fmoc-Leu-OH, Fmoc-Ala-OH, Fmoc-Gln(Trt)-OH, Fmoc-Asn(Trt)-OH, Fmoc-Ile-OH, Fmoc-Glu(tBu)-OH, Fmoc-Glu(tBu)-OH, Fmoc-Asn(Trt)-OH, Fmoc-Val-OH, Fmoc-Gln(Trt)-OH, Fmoc-Ser(tBu)-OH, Fmoc-Ile-OH, Fmoc-Ser(tBu)-OH, Fmoc-Ala-OH, Fmoc-Asp(tBu)-OH, Fmoc-Tyr(tBu)-OH, Fmoc-Glu(tBu)-OH, Fmoc-Asp(tBu)-OH, Fmoc-Ser(tBu)-OH, Fmoc-Pro-OH, Fmoc-Tyr(tBu)-OH, Fmoc-Val-OH, Fmoc-Lys(Aloc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The amino group of the final amino acid is acetylated using Acetic Acid, activated using O-benzotriazol-1-yl-N,N,N',N'-tetramethyl-uronium hexafluorophosphate (HBTU) and Diisopropylethylamine (DIEA). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAC in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30–55% B (0.045% TFA in H$_2$O (A) and 0.045% TFA in CH$_3$CN (B) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

(tBu)-OH, Fmoc-Asp(tBu)-OH, Fmoc-Ser(tBu)-OH, Fmoc-Pro-OH, Fmoc-Tyr(tBu)-OH, Fmoc-Val-OH. They are dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The amino group of the final amino acid is acetylated using Acetic Acid activated using O-benzotriazol-1-yl-N,N,N',N'-tetramethyl-uronium hexafluorophosphate (HBTU) and Diisopropylethylamine (DIEA). The selective

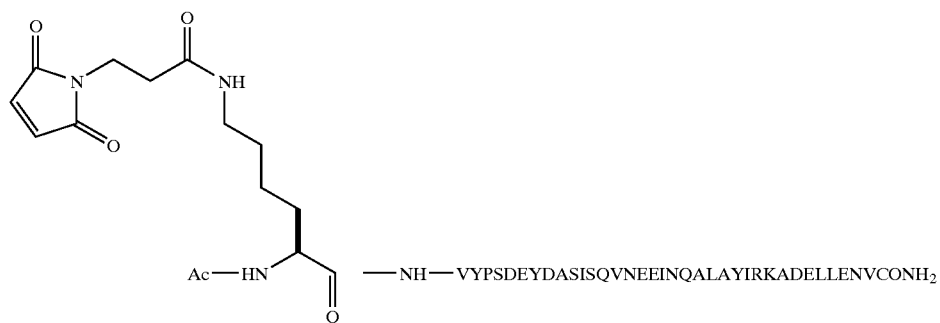

EXAMPLE 9

Preparation of Modified RSV Peptide VYPSDEYDASISQVNEEINQALAYIRKADELLENV

RSV peptide VYPSDEYDASISQVNEEINQALAYIRK-ADELLENV (SEQ ID NO:9) was synthesized and modified to include a linking group and a maleimide group according to the synthesis scheme set forth below.

Solid phase peptide synthesis on a 100 μmole scale is performed using manual solid-phase synthesis, a Symphony Peptide Synthesizer and Fmoc protected Rink Amide MBHA. The following protected amino acids are sequentially added to resin: Fmoc-Val-OH, Fmoc-Asn(Trt)-OH, Fmoc-Glu(tBu)-OH, Fmoc-Leu-OH, Fmoc-Leu-OH, Fmoc-Glu(tBu)-OH, Fmoc-Asp(tBu)-OH, Fmoc-Ala-OH, Fmoc-Lys(Aloc)-OH, Fmoc-Arg(Pbf)-OH, Fmoc-Ile-OH, Fmoc-Tyr(tBu)-OH, Fmoc-Ala-OH, Fmoc-Leu-OH, Fmoc-Ala-OH, Fmoc-Gln(Trt)-OH, Fmoc-Asn(Trt)-OH, Fmoc-Ile-OH, Fmoc-Glu(tBu)-OH, Fmoc-Glu(tBu)-OH, Fmoc-Asn(Trt)-OH, Fmoc-Val-OH, Fmoc-Gln(Trt)-OH, Fmoc-Ser(tBu)-OH, Fmoc-Ile-OH, Fmoc-Ser(tBu)-OH, Fmoc-Ala-OH, Fmoc-Asp(tBu)-OH, Fmoc-Tyr(tBu)-OH, Fmoc-Glu deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30–55% B (0.045% TFA in H$_2$O (A) and 0.045% TFA in CH$_3$CN (B) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

Fmoc—Ramage Resin
Step 1 | SPPS

Ac—VYPSDEYDASISQVNEEINQALAYIRK(Aloc)ADELLENV-PS

Step 2 | Pd(PPh$_3$)$_4$/NMM/HOAc/CHCl$_3$: C$_6$H$_6$

Ac—VYPSDEYDASISQVNEEINQALAYIRKADELLENV—

Step 3 | 3-maleimidopropionic acid

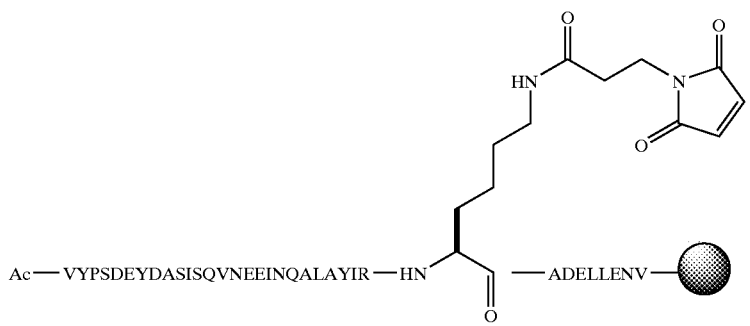

Step 4 | 85% TFA/5% TIS/5% thioanisole/5% phenol

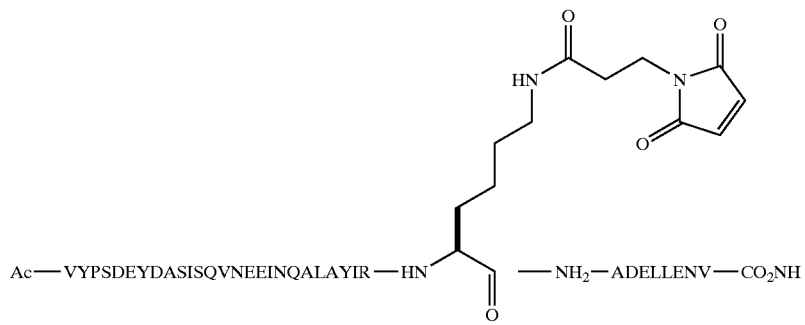

EXAMPLE 10

Preparation of Modified GLP-1 Peptide HAEGTFTSDVSSYLEGQAAKEFIAWLVKGRK

GLP-1 peptide HAEGTFTSDVSSYLEGQAAKEFI-AWLVKGRK (SEQ ID NO:10) was synthesized and modified to include a linking group and a maleimide group according to the synthesis scheme set forth below.

Solid phase peptide synthesis on a 100 µmole scale was performed using manual solid-phase synthesis, a Symphony Peptide Synthesizer and Fmoc protected Ramage Resin: Fmoc-Lys(Aloc)-OH, Fmoc-Arg(Pbf)-OH, Fmoc-Gly-OH, Fmoc-Lys(Boc)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(tBu)-OH, Fmoc-Lys(Boc)-OH, Fmoc-Ala-OH, Fmoc-Ala-OH, Fmoc-Gln(Trt)-OH, Fmoc-Gly-OH, Fmoc-Glu(tBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(tBu)-OH, Fmoc-Ala-OH, Fmoc-His(Boc)-OH, The following protected amino acids were sequentially added to resin: They were dissolved in N,N-dimethylformamide (DMF) and, according to the sequence, activated using O-benzotriazol-1-yl-N,N,N',N'-tetramethyl-uronium hexafluorophosphate (HBTU) and Diisopropyl-ethylamine (DIEA). Removal of the Fmoc protecting group was achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL). The synthesis was then re-automated for the addition of the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et$_2$O (Step 4). The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

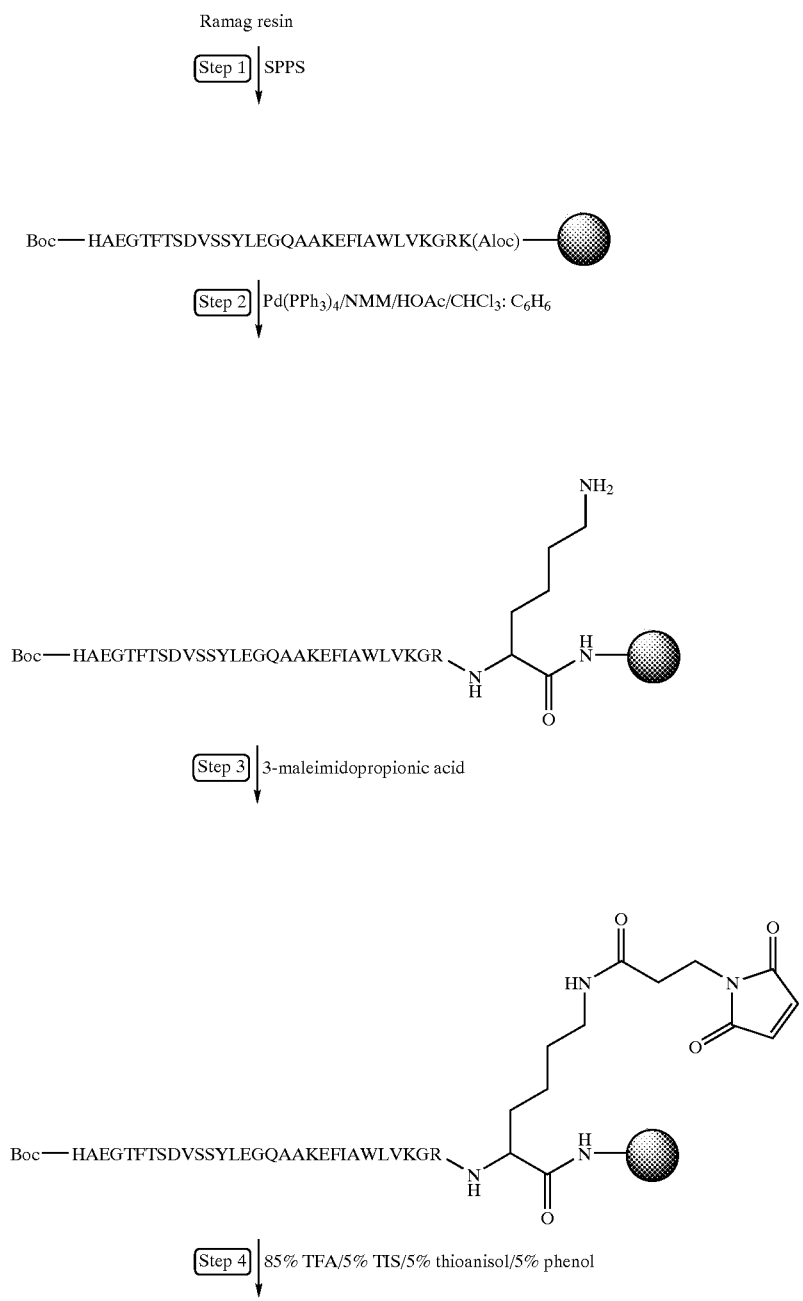

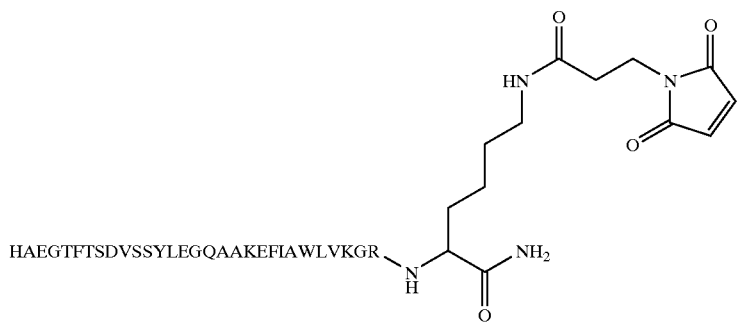

EXAMPLE 11

Preparation of Modified GLP-1 Peptide HAEGTFTSDVSSYLEGQAAKEFIAWLVKGRK

GLP-1 peptide HAEGTFTSDVSSYLEGQAAKEFI-AWLVKGRK (SEQ ID NO:11) was synthesized and modified to include a linking group and a maleimide group, as described below.

Solid phase peptide synthesis on a 100 μmole scale was performed using manual solid-phase synthesis, a Symphony Peptide Synthesizer and Fmoc protected Ramage Resin: Fmoc-Arg(Pbf)-OH, Fmoc-Gly-OH, Fmoc-Lys(Boc)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(tBu)-OH, Fmoc-Lys(Aloc)-OH, Fmoc-Ala-OH, Fmoc-Ala-OH, Fmoc-Gln(Trt)-OH, Fmoc-Gly-OH, Fmoc-Glu(tBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(tBu)-OH, Fmoc-Ala-OH, Fmoc-His(Boc)-OH, The following protected amino acids were sequentially added to resin: They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL). The linking group Fmoc-AEEA-OH was added and then the Fmoc was removed in the usual fashon. This procedure was redone to add a second AEEA linking group.

The synthesis was then re-automated for the addition of the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et$_2$O (Step 4).

The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

EXAMPLE 12

Preparation of Modified K5 Peptide PRKLYDYK

K5 peptide PRKLYDYK (SEQ ID NO:12) was synthesized and modified to include a linking group and a maleimide group according to the synthesis scheme set forth below.

Using automated peptide synthesis, the following protected amino acids were sequentially added to Rink Amide MBHA resin (0.48 mmol/mg) (250 μmol scale): Fmoc-Lys (Aloc)OH, Fmoc-Tyr(tBu)OH, Fmoc-Asp(tBu)-OH, Fmoc-Tyr(tBu)OH, Fmoc-Leu-OH, Fmoc-Lys(Boc)-OH, Fmoc-Arg(Pbf)-OH, Fmoc-Pro-OH. Each coupling was accomplished using 2 equivalents of amino acid, 1 equivalent HBTU, and 2 equivalents DIEA and performed twice for 30 min. The Fmoc group of the N-terminal amino acid (Pro) was removed using 20% piperidine/DMF (3×10min).

The resin was subsequently washed with 6×4 mL DMF, 3×3 mL EtOH and 6×4 mL DMF. Acetylation of the N-terminus was accomplished manually on the Symphony by adding 4 mL of 15 equivalents HOAc, 2 equivalents DIEA and 4 equivalents HBTU in DMF. Acetic capping was performed 2×30 min. The resin was subsequently washed with 3×4 mL CH$_2$Cl$_2$, 6×4 mL 0.5% DIEA/CH$_2$Cl$_2$, 3×4 mL EtOH and 6×4 mL DMF.Selective deprotection of the Lys (Aloc) group was performed manually on the Symphony by treating the resin with a solution of 3 equivalents of Pd(PPh$_3$)$_4$ dissolved in 5 mL of CHCl$_3$:Benzene (1:1) with 2.5% NMM (v/v) and 5% HOAc for 2 h. The resin was then washed with CHCl$_3$ (6×5 mL), 0.5% DIEA in CH$_2$Cl$_2$ (6×5 mL), 0.02 M sodium diethylthiocarbamate in DMF (6×5 mL), EtOH (3×4 mL) and DMF (6×5 mL).

Coupling of 3-maleimidoproprionic acid (MPA) was performed by resuming automation on the Symphony, which involves delivery of 2 equivalents of MPA, 2 equivalents DIEA and 1 equivalent HBTU to the reaction vessel. The coupling was carried out twice at 30 min. Washing was conducted using 6×4 mL DMF, 3×3 mL EtOH and 6×4 mL DMF. Cleavage from the resin was performed by automation using 10 mL of the following cleavage mixture: 85% TFA/ 5% triisopropyl silane/5% thioanisol/5% phenol. After the peptide was cleaved from the resin for 2 hrs, the resin was washed with TFA and $CH_2Cl_2$. The combined cleavage and washing liquors concentrated to 1–2 mL using a rotovap with mild heating (30° C.) and the peptide was precipitated with $Et_2O$. The precipitate was collected by filtration using a SPPS manifold and washed with 10 mL of ethyl acetate and 30 mL of $Et_2O$. The precipitate was subsequently dissolved in 10 mL of water containing 5% acetonitrile (0.04% TFA) in water (0.04% TFA) for chromatographic purification.

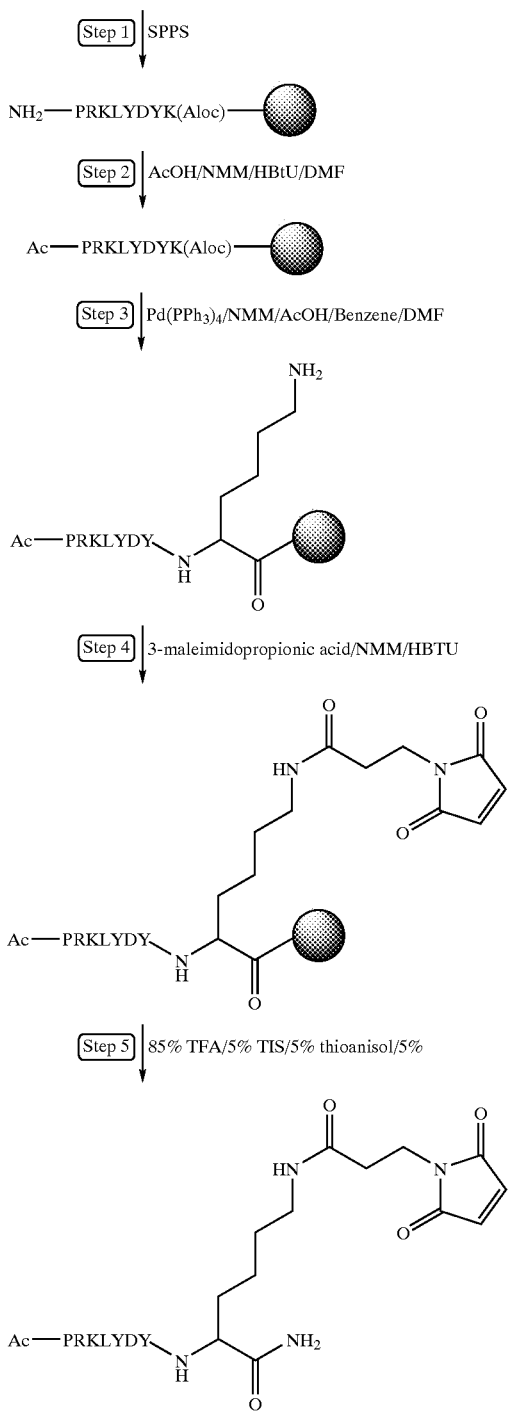

EXAMPLE 13

Preparation of Modified K5 Peptide RNPDGDVGGPWAWTTAPRKLYDY

K5 peptide RNPDGDVGGPWAWTTAPRKLYDY (SEQ ID NO:13) was synthesized and modified to include a linking group and a maleimide group according to the synthesis scheme set forth below.

Using automated peptide synthesis, the following protected amino acids were sequentially added to Rink Amide MBHA resin (0.48 mmol/mg) (100 μmol scale): Fmoc-Tyr(tBu)OH, Fmoc-Asp(tBu)-OH, Fmoc-Tyr(tBu)OH, Fmoc-Leu-OH Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu)OH, Fmoc-Ala-OH, Fmoc-Trp-OH, Fmoc-Pro-OH, Fmoc-Gly-OH, Fmoc-Gly-OH, Fmoc-Val-OH, Fmoc-Asp(tBu)-OH, Fmoc-Gly-OH, Fmoc-Asp(tBu)-OH, Fmoc-Pro-OH, Fmoc-Asn(Trt)-OH, Fmoc-Arg(Pbf)-OH, MPA.

Each coupling was accomplished using 5 equivalents of amino acid, 1 equivalent HBTU, and 2 equivalents DIEA and performed twice for 30 min. Cleavage from the resin was performed by automation using 10 mL of the following cleavage mixture: 85% TFA/5% triisopropyl silane/5% thioanisol/5% phenol. After the peptide was cleaved from the resin for 2 hrs, the resin was washed with TFA and $CH_2Cl_2$.

The combined cleavage and washing liquors concentrated to 1–2 mL using a rotovap with mild heating (30° C.) and the peptide was precipitated with $Et_2O$. The precipitate was collected by filtration using a SPPS manifold and washed with 10 mL of ethyl acetate and 30 mL of $Et_2O$. The precipitate was subsequently dissolved in 10 mL of water containing 5% acetonitrile (0.04% TFA) in water (0.04% TFA) for chromatographic purification. Purification of all the peptides was performed using a Phenomenex Luna 10μ phenyl-hexyl, 21 mm×250 mm column equilibrated with a water/TFA mixture (0.045% TFA in $H_2O$; Solvent A).

Elution was achieved at 18 mL/min by running a 10–30% acetonitrile gradient over 60 min (0.045% TFA in $CH_3CN$; Solvent B). Peptides were detected by UV absorbance (Varian Dynamax UVD II) at 214 and 254 nm. Fractions were collected in 9 mL aliquots. Fractions containing the desired product were identified by mass after direct injection onto LC/MS. The selected fractions were subsequently analyzed by analytical HPLC (10–40% solvent B over 20 min; Phenomenex Luna 5μ phenyl-hexyl, 10 mm×250 mm column, 0.5 mL/min) to identify fractions with ≧95% purity for pooling. The pool was freeze-dried using dry ice and acetone and subsequently lyophilized for at least 2 days to yield a white powder.

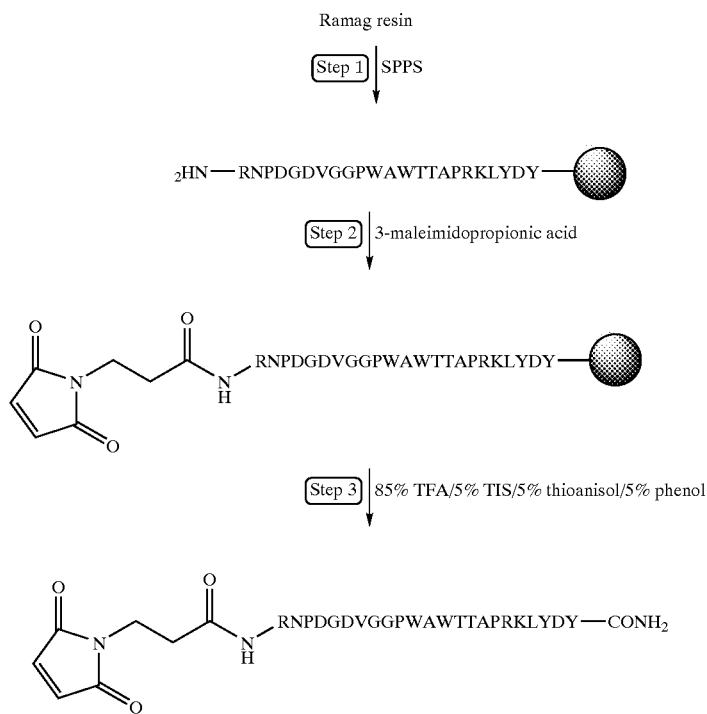

EXAMPLE 14

Preparation of Modified BBB Peptide YGRKKRRQRRRL

BBB peptide YGRKKRRQRRRL (SEQ ID NO:14) was synthesized and modified to include a linking group and a maleimide group according to the synthesis scheme set forth below.

Solid phase peptide synthesis on a 100 μmole scale was performed using manual solid-phase synthesis, a Symphony Peptide Synthesizer and Fmoc protected Ramage Resin. The following protected amino acids were sequentially added to resin: Fmoc-Lys(Aloc)-OH, Fmoc-Arg(Pbf)-OH, Fmoc-Arg(Pbf)-OH, Fmoc-Arg(Pbf)-OH, Fmoc-Gln(Trt)-OH, Fmoc-Arg(Pbf)-OH, Fmoc-Arg(Pbf)-OH, Fmoc-Lys(Boc)-OH, Fmoc-Lys(Boc)-OH, Fmoc-Arg(Pbf)-OH, Fmoc-Gly-OH, Fmoc-Tyr(tBu)-OH, They were dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

After the tyrosine deprotection, Biotin was anchored at the N-terminus via regular activation and coupling conditions. The selective deprotection of the Lys (Aloc) group is performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL). The synthesis was then re-automated for the addition of the 3-maleimidopropionic acid (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et$_2$O (Step 4). The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired molecule in >95% purity, as determined by RP-HPLC.

-continued
Step 2 | Biotin
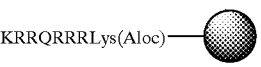
Step 3 | Pd(PPh$_3$)$_4$/NMM/HOAc/CHCl$_3$: C$_6$H$_6$
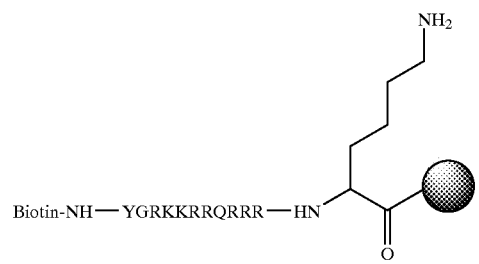
Step 4 | 3-maleimidopropionic acid
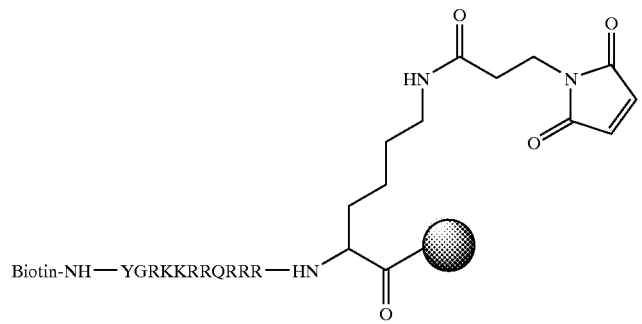
Step 5 | 85% TFA/5% TIS/5% thioanisole/5% pheno
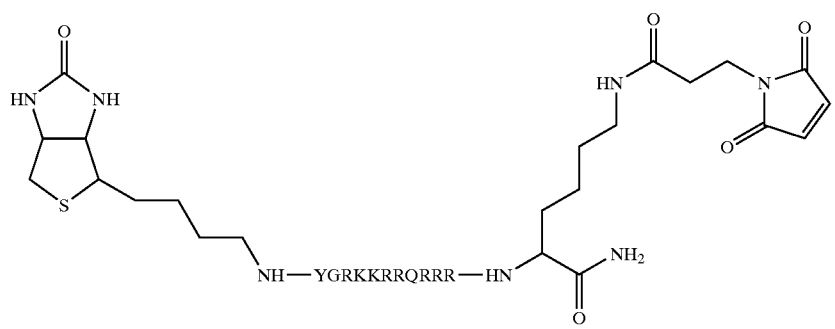

EXAMPLE 15

Preparation of Modified BBB Peptide YGRKKRRQRRRL

BBB peptide YGRKKRRQRRRL (SEQ ID NO:15) was synthesized and modified to include a linking group and a maleimide group according to the synthesis scheme set forth below.

Solid phase peptide synthesis on a 100 µmole scale was performed using manual solid-phase synthesis, a Symphony Peptide Synthesizer and Fmoc protected Ramage Resin. The following protected amino acids were sequentially added to resin: Fmoc-Lys(Aloc)-OH, Fmoc-Arg(Pbf)-OH, Fmoc-Arg(Pbf)-OH, Fmoc-Arg(Pbf)-OH, Fmoc-Gln(Trt)-OH, Fmoc-Arg(Pbf)-OH, Fmoc-Arg(Pbf)-OH, Fmoc-Lys(Boc)-OH, Fmoc-Lys(Boc)-OH, Fmoc-Arg(Pbf)-OH, Fmoc-Gly-OH, Fmoc-Tyr(tBu)-OH, They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL). After the aloc deprotection, Biotin was anchored at the ε-N terminal of the deprotected lysine via regular activation and coupling conditions. The Fmoc removal of the N-terminus was then achieved with standard conditions. The synthesis was then re-automated for the addition of the 3-maleimidopropionic acid at the end terminus (Step 3). Between every coupling, the resin was washed 3 times with N,N-dimethylformamide (DMF) and 3 times with isopropanol. The peptide was cleaved from the resin using 85% TFA/5% TIS/5% thioanisole and 5% phenol, followed by precipitation by dry-ice cold Et$_2$O (Step 4). The product was purified by preparative reversed phased HPLC using a Varian (Rainin) preparative binary HPLC system: gradient elution of 30–55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm to afford the desired molecule in >95% purity, as determined by RP-HPLC.

EXAMPLE 16

Preparation of Modified Dynorphin Peptide YGGFLRRIRPKLK

Dynorphin peptide YGGFLRRIRPKLK (SEQ ID NO:16) was synthesized and modified to include a linking group and a maleimide group according to the synthesis scheme set forth below.

Solid phase peptide synthesis on a 100 µmole scale is performed using manual solid-phase synthesis, a Symphony Peptide Synthesizer and Fmoc protected Ramage Resin. The following protected amino acids are sequentially added to resin: Fmoc-Lys(Aloc)-OH, Fmoc-Leu-OH, Fmoc-Lys(Boc)-OH, Fmoc-Pro-OH, Fmoc-Arg(Pbf)-OH, Fmoc-Ile-OH, Fmoc-Arg(Pbf)-OH, Fmoc-Arg(Pbf)-OH, Fmoc-Leu-OH, Fmoc-Phe-OH, Fmoc-Gly-OH, Fmoc-Gly-OH, Boc-Tyr(tBu)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The amino group of the final amino acid is acetylated using Acetic Acid activated using O-benzotriazol-1-yl-N,N,N',N'-tetramethyl-uronium hexafluorophosphate (HBTU) and Diisopropylethylamine (DIEA). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30–55% B (0.045% TFA in H$_2$O (A) and 0.045% TFA in CH$_3$CN (B) over 180 min at 9.5 mL/min using a Phenomenex Luna 10µ phenyl-hexyl, 21 mm×25 cm column and UV detector (Varian Dynamax UVD II) at λ214 and 254 nm to afford the desired molecule in >95% purity, as determined by RP-HPLC.

EXAMPLE 17

2-[2-[4-[(4-chloropheny)phenylmethyl[-1-piperazinyl]ethoxy]-maleimidopropionylacetamide. (Modified Cetirizine)

A mixture of 1-[(4-chlorophenylmethyl]-piperazine 1, methyl (2-chloroethoxy)-acetate 2 and sodium carbonate in anydrous xylene is heated under reflux with good stirring as indicated in the schematic below. The reaction mixture is then cooled and filtered and the solid is washed with benzene, the washed solid being discarded. The filtrate is evaporated to dryness and the evaporation residue is purified by chromatography on a column of silica (eluent: chloroform:methanol 97:3 v/v). This generated methyl 2-[2-[4-[(4-chlorophenyl)phenylmethyl]-1-piperazinyl]ethoxy]-acetate 3. The compound is dissolved in of absolute ethanol. 1 N ethanolic solution of potassium hydroxide is then added thereto and the reaction mixture is heated under reflux for 4 hours. It is cooled and the precipitate removed by filitration, after washing with diethyl ether. The filtrate is evaporated to dryness and the evaporation residue is triturated with diethyl ether and left to crystallize. The compound potassium 2-[2-[4-[(4-chlorophenyl)phenylmethyl]-1-piperazinyl]ethoxy]-acetate is then obtained. The potassium salt is dissolved in water and adjusted with 10% hydrochloric acid to a pH of 4. The solution is extracted with chloroform and the organic phase is dried over anhydrous magnesium sulfate, whereafter it is evaporated to dryness. The evaporation residue is triturated with diethyl ether and left to crystallize to produce 2-[2-[4-[(4-chloropheny)phenylmethyl[-1-piperazinyl]ethoxy]-acetic acid 4. 2-[2-[4-[(4-chloropheny)phenylmethyl[-1-piperazinyl]ethoxy]-acetic acid 4 is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropylamine. The reaction is stirred for 3 hours. The organic phase is then washed with water and brine, dried over MgSO$_4$, triturated with cold ether and left to crystallize. This last step generated 5 2-[2-[4-[(4-chloropheny)phenylmethyl[-1-piperazinyl]ethoxy]-maleimidopropionylacetamide, a modified antihistamine molecule.

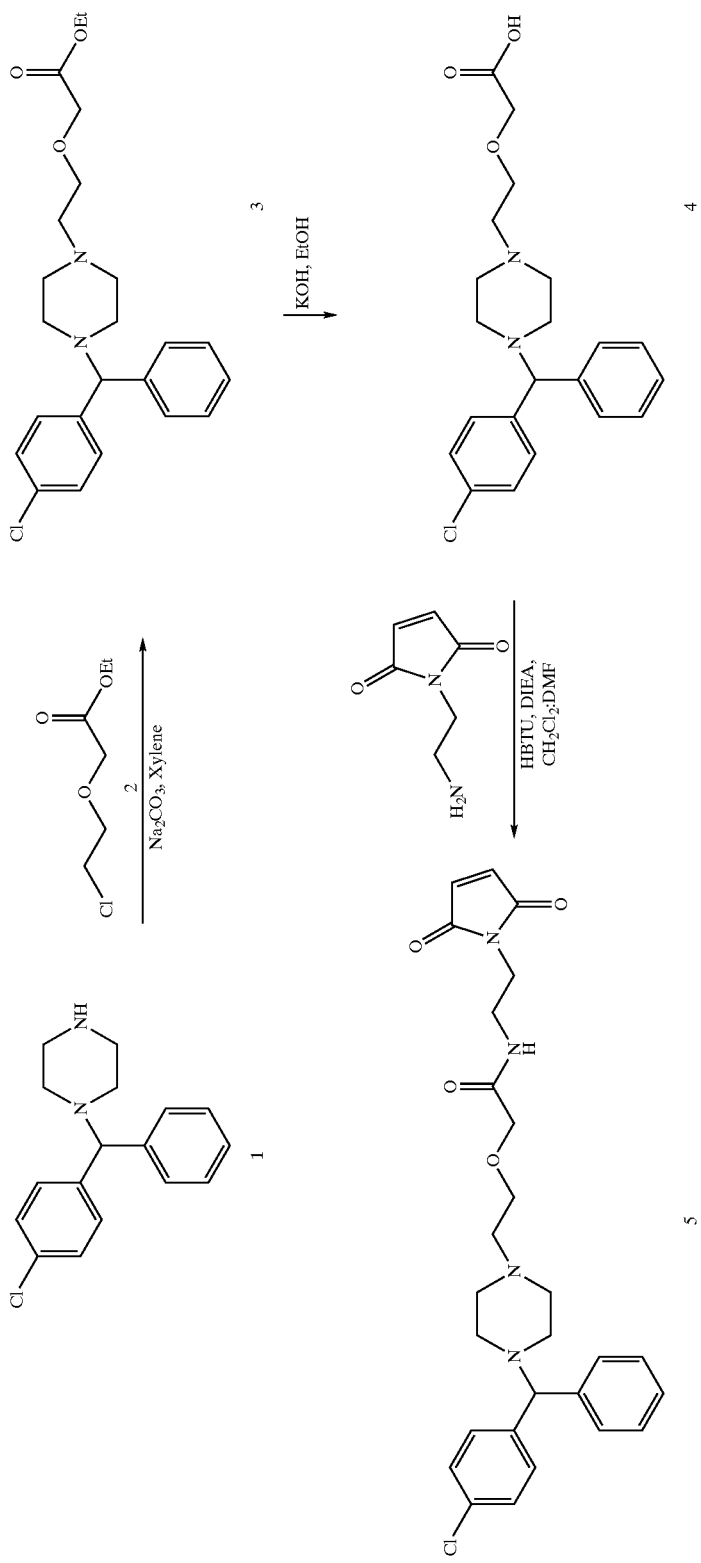

EXAMPLE 18

11-(N-maleimidopropionyl-4-piperidylidene)-8-chloro-6,11-dihydro-5H-benzo-[5,6]-cyclohepta-[1,2-b]-pyridine (Modified Loratidine)

11-(N-8-chloro-4-piperidylidene)-6,11-dihydro-5H-benzo-[5,6]-cyclohepta-[1,2-b]-pyridine 1 is placed is placed in DMF and activated with and O-(benzotriazol-1-yl)-N,N',N',N',-tetramethyluronium hexafluorophosphate (HBTU) and Diisopropylethylamine (DIEA) as indicated in the schematic below. To the reaction mixture is added 3-maleimidopropionic acid. The reaction is stirred for 3 hours. The organic phase is then washed with water and brine, dried over MgSO$_4$, chromatographied triturated with cold ether and left to crystallize to generate 2, 11-(N-maleimidopropionyl-4-piperidylidene)-8-chloro-6,11-dihydro-5H-benzo-[5,6]-cyclohepta-[1,2-b]-pyridine, a modified antihistamine molecule.

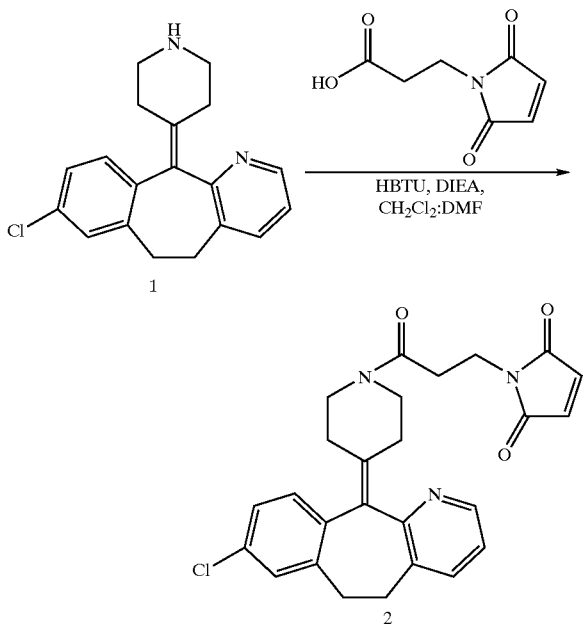

EXAMPLE 19

Modified Tirofiban

A four-neck round bottom flask equipped with a mechanical stirrer, condenser, nitrogen inlet, HCl trap, heating unit and a thermometer probe is purged with nitrogen overnight and then charged with L-tyrosine 1, CH$_3$CN, N,O-bis-trimethylsilyl-trifluoromethyl-acetamide. The suspension is heated to gentle reflux for 2 h. The resulting clear solution O,O'-bis-trimethylsilyl-(L)-tyrosine 2, is cooled pyridine and n-BuSO$_2$Cl are slowly added over 30 minutes as indicated in the schematic below. The reaction mixture is then stirred at room temperature. Almost all the solvent is removed in a batch concentrator, and the resulting oily residue is treated with 15%/KHSO4 and stirred vigorously for 1 hour. The mixture is extracted with i-propyl acetate. The combined organic layer is treated with Ecosorb TM S-402 and stirred at room temperature overnight. Ecosorb TM is removed by filtration and the filter cake is washed with i-propyl acetate. The filtrate is evaporated to dryness and the resulting yellow oil is dissolved in hot EtOAc. Hexane is added slowly to the stirring solution and the resulting slurry is stirred at room temperature overnight. The solid is collected by filtration and the filter cake is washed with EtOAc/hexane. After drying under vacuum is obtained as a white solid.

To a four-neck round bottom flask equipped with a mechanical stirrer, condenser, nitrogen inlet and a thermometer probe is charged N-n-butanesulfonyl-(L)-tyrosine 3, 4-(4-pyridinyl)-butyl chloride.HCl 4 and DMSO. With vigorous stirring, 3 N aq. KOH is added over 15 min.

The temperature is maintained in the 30–40° C. range for this operation using cooling water. Potassium iodide is added, and the mixture is heated for 36 h. After cooling to room temperature, the mixture is diluted with 0.25 N NaOH and extracted once with t-butyl methyl ether. The aqueous layer is treated with Ecosorb S-402 and Nuchar SA and the resulting mixture is mechanically stirred for 1 h. The mixture is filtered through a coarse-porosity sintered funnel and the filtered cake is washed with water. The combined filtrate is placed in a vessel equipped with a pH meter probe and a mechanical stirrer. With vigorous stirring, NaCl is added, stirred for 30 min, and then 50% aq. acetic acid wash added until pH 4.80, and stirring continued for 2–3 h. The resulting slurry is filtered through a coarse-porosity sintered funnel, and the cake is washed with water. The crude product is dried under house-vacuum under a positive nitrogen pressure to give beige solid 5 having a wt % purity of 95%.

Selective hydrogenation of the pyridine ring to piperidine ring is accomplished by using 5 wt % of 10% Pd/C in AcOH at 60 C. to give the target product cleanly without reduction of the phenolic ring. Filtration of the reaction mixture, evaporation of acetic acid followed by crystallizing the product 6 from 6% AcOH/water.

To a RB flask equipped with a thermometer probe and addition funnel is charged the crude and 0.25 N NaOH. After complete dissolution, the solution is cooled to room temperature, and adjusted to pH 7 by slow additon of 1 N HCl. The solution is further brought down to pH 5.5 by slow addition of 0.5 N HCl. Stirring is continued for 1 h, then the slurry is filtered through a coarse funnel padded with a sheet of shark-skin paper and a polypropylene pad (10 mu m) and the cake is washed with water. The solid is dried under house vacuum with nitrogen sweep to give a beige solid. The compound is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropylamine. The reaction is stirred for 3 hours. The organic phase is then washed with water and brine, dried over MgSO$_4$, triturated with cold ether and left to crystallize to generate the modfied tirofiban 7. Tirofiban is an anti-angina agent.

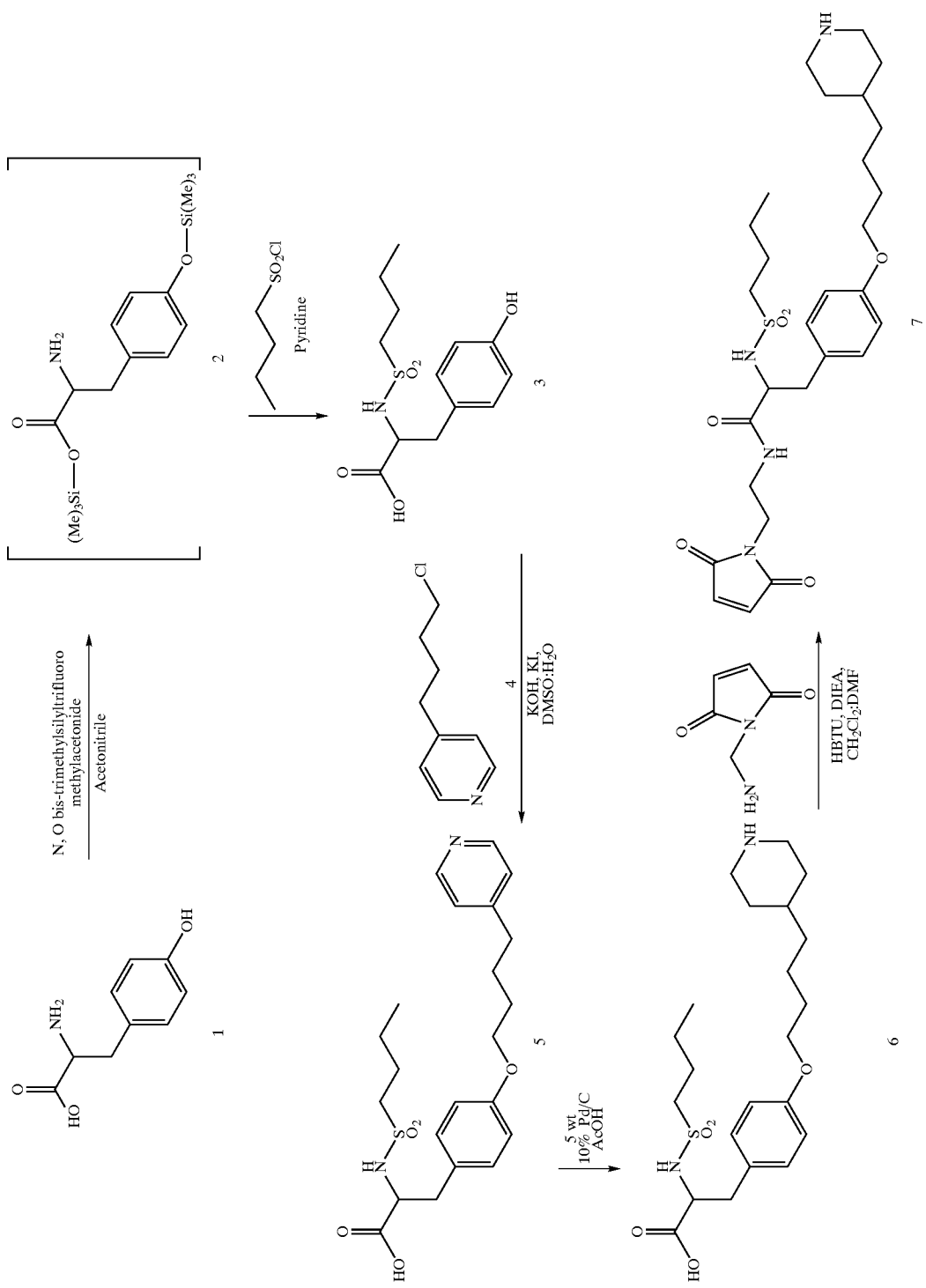

EXAMPLE 20

N-(2-maleimidoethyl)-(1(S)-Ethoxycarbonyl-3-phenylpropyl)-L-alanyl-L-prolinylamide Ethyl 2-oxo-4-phenylbutyrate 1 and L-alanyl-L-proline 2 are dissolved in a 1:1 ethanol-water solvent as indicated in the schematic below. A solution of sodium cyanoborohydride in ethanol-water is added dropwise at room temperature over the course of two hours. When reaction is complete, the product is absorbed on strong acid ion-exchange resin and eluted with 2% pyridine in water. The product-rich cuts are freeze dried to give crude N-(1-ethoxycarbonyl-3-phenylpropyl)-L-alanyl-L-proline 4 and the compound is purified by chromatography to yield the desired isomer. The compound 4 is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropylamine. The reaction is stirred for 3 hours. The organic phase is then washed with water and brine, dried over MgSO$_4$, triturated with cold ether and left to crystallize to produce N-(2-maleimidoethyl)-(1(S)-Ethoxycarbonyl-3-phenylpropyl)-L-alanyl-L-prolinylamide, a modified anti-hypertensive agent.

EXAMPLE 21

N-[2-maleimidoethyl-$\epsilon$-(3,4,5-trimethoxybenzamido)-caproic amide 3,4,5-trimethoxybenzoyl chloride 1 is added along with amino-hexanoic acid 2 in a solution of 1 N NaOH as indicated in the schematic below. The resulting solution is preferably treated with char to decolorize it, the char is filtered, and the filtrate neutralized with dilute HCl to Congo red indicator end-point. The resulting precipitate is separated by filtration washed with water, dried, then recrystallized from ethanol to genarate 3. The compound is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropylamine. The reaction is stirred for 3 hours. The organic phase is then washed with water and brine, dried over MgSO$_4$, triturated with cold ether and left to crystallize in order to produce 4 N-[2-maleimidoethyl-$\epsilon$-(3,4,5-trimethoxybenzamido)-caproic amide, an anti-arrhthymetic agent.

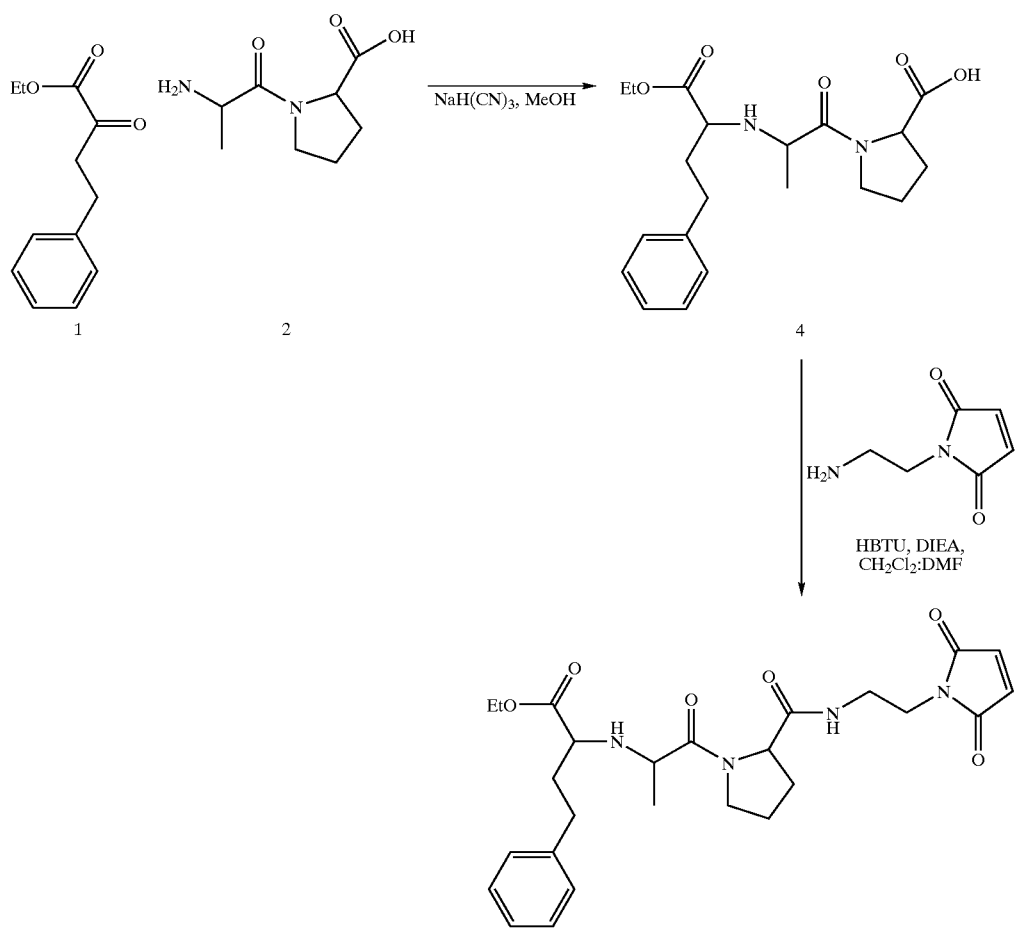

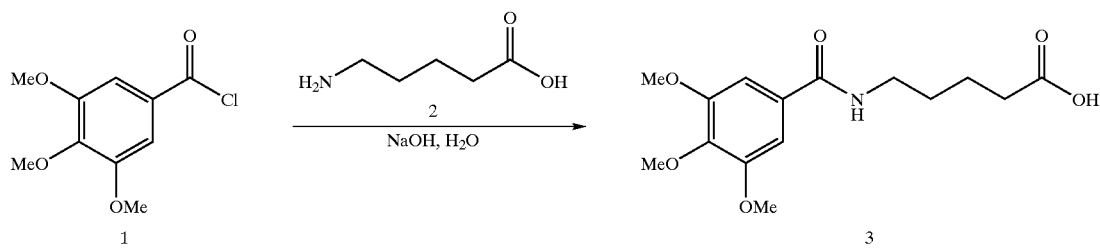

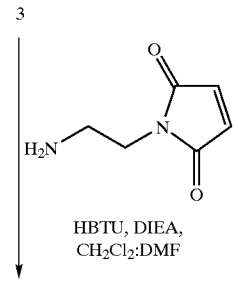

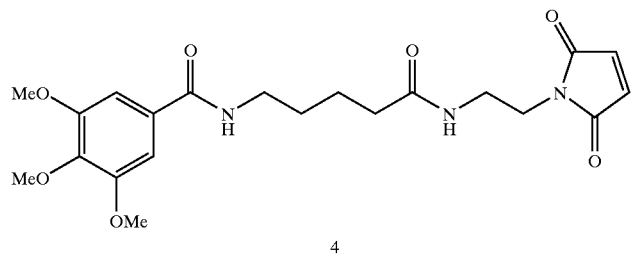

EXAMPLE 22

Maleimidoethyl-1-theobromineacetamide (Modified 1-theobromineacetic acid)

1-theobromineacetic acid 1 is placed in DMF and activated with O-(benzotriazol-1-yl)-N,N',N',N',-tetramethyluronium hexafluorophosphate (HBTU) and Diisopropylethylamine (DIEA) as indicated in the schematic below. To the reaction mixture is added 3-maleimido ethylamine. The reaction is stirred for 3 hours. The organic phase is then washed with water and brine, dried over MgSO$_4$, chromatographied, triturated with cold ether and left to crystallize to produce 2 Maleimidoethyl-1-theobromineacetamide, a modifed bronchodilator.

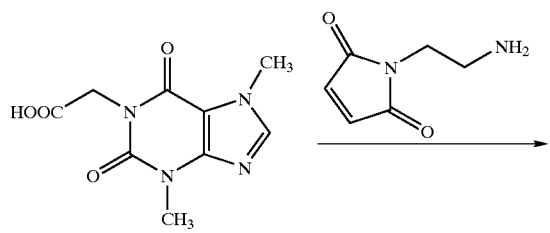

-continued

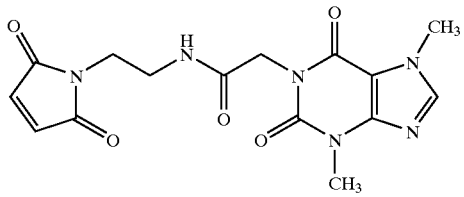

EXAMPLE 23

4-[N-phenyl-3-maleimidopropionamido]-1-(2-phenylethyl)piperidine (Modified-Fentanyl)

1-phenylethyl-4-piperidone 1 was placed in 1,2, dichloroethane along with aniline 2, sodiumcyanoborohydride and it is refluxed for 18 hours. The reaction is then cooled to RT and the reaction is extracted with brine to generate 3 as indicated in the schematic below. Finally The compound is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropionic acid. The reaction is stirred for 3 hours. The organic phase is then washed with water and brine, dried over MgSO$_4$, triturated with cold ether and left to crystallize to generate 4, a modified pain killer (opioid molecule).

EXAMPLE 24

N-(2-maleimidoethyl)-2-[4-(2-oxocyclopentan-1-ylmethyl)phenyl]-propionamide (Modified-Loxoprofen)

Ethyl 2 cyclopentanonecarboxylate 1 and ethyl 2-(4-iodomethylphenyl)propionate 2 are placed in N,N,dimethylformamide along with potassium hydroxyde as indicated in the schematic below. The solution is stirred at room temperature for 5 hours and at 50° C. for 1 hour. The reaction is cooled and acidified with acetic acid and N,N,dimethylformamide is removed by vacuum. The residue is extracted with ether and the organic phase is washed with water and dried on $Mg_2SO_4$ to afford 3 Finally, the compound 3 is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropylamine. The reaction is stirred for 3 hours. The organic phase is then washed with water and brine, dried over $MgSO_4$, chromatographied, triturated with cold ether and left to crystallize to generate 4 Maleimidopropamyl 2-[4-(2-oxocyclopentan-1-ylmethyl)phenyl]propionamide to produce the modified anti-inflammatory agent.

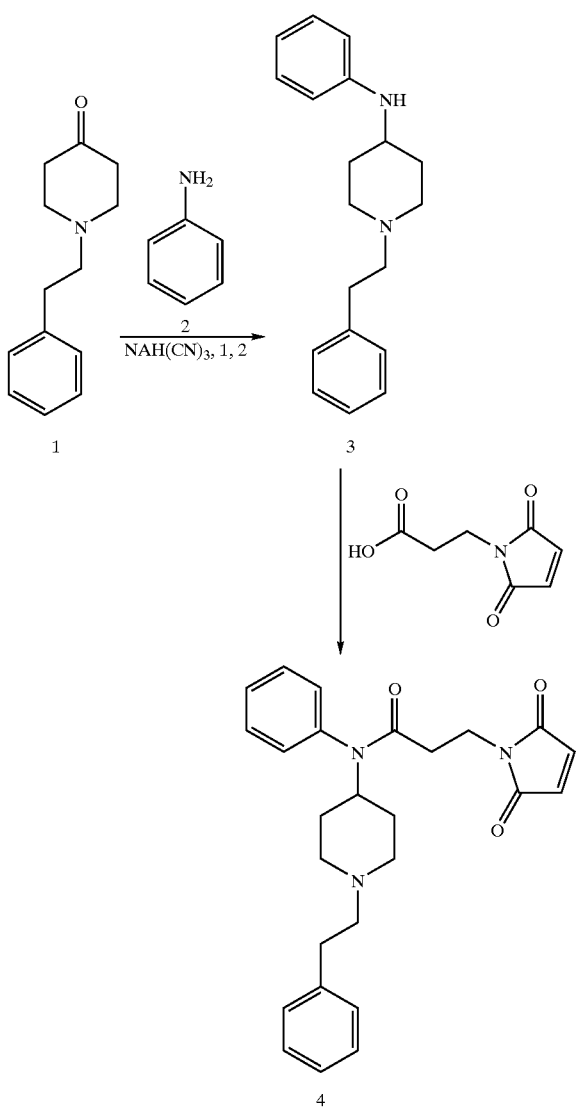

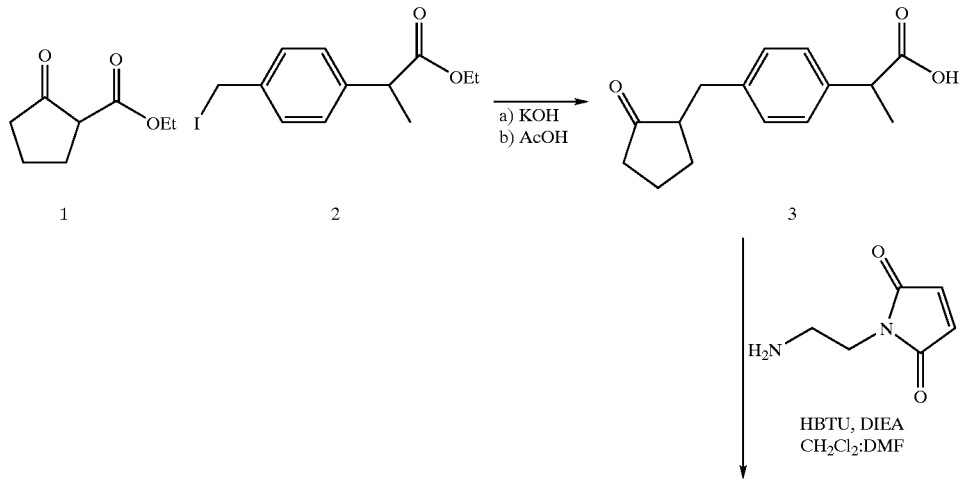

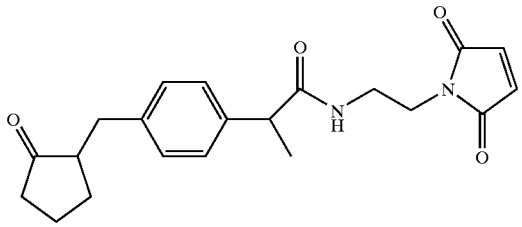

4

EXAMPLE 25

N-maleimidopropionyl-N-methyl 3-(p-trifluoromethylphenoxy)-3-phenylpropylamine (Modified Fluoxetine)

β-dimethylaminopropiophenone hydrochloride 1 is converted to the corresponding free base by the action of aqueous sodium hydroxide. The liberated free base is taken up in ether, the ether layer separated and dried, and the ether removed therefrom in vacuo. The residual oil comprising β-dimethylaminopropiophenone is dissolved in tetrahydrofuran, and the resulting solution added in dropwise fashion with stirring to a solution of diborane in tetrahydrofuran. The reaction mixture is stirred overnight at room temperature. Next, aqueous hydrochloric acid is added to decompose any excess diborane present. The tetrahydrofuran is removed by evaporation. The acidic solution is extracted twice with benzene, and the benzene extracts are discarded. The acidic solution is then made basic with an excess of 5 N aqueous sodium hydroxide. The basic solution is extracted three times with benzene. The benzene extracts are separated and combined, and the combined extracts washed with a saturated aqueous sodium chloride and then dried to produce 2. A solution containing N,N,-dimethyl 3-phenyl-3-hydroxypropylamine 2 in chloroform is saturated with dry gaseous hydrogen chloride. Thionyl chloride is then added to the chloroform solution at a rate sufficient to maintain reflux. The solution is refluxed an additional 5 hours. Evaporation of the chloroform and other volatile constituents in vacuo yielded N,N-dimethyl 3-phenyl-3-chloropropylamine hydrochloride 3 which is collected by filtration, and the filter cake washed twice with acetone. P-trifluoromethylphenol 4, solid sodium hyroxide and methanol are placed in a round-bottom flask equipped with magnetic stirrer, condenser and drying tube. The reaction mixture is stirred until the sodium hydroxide had dissolved. Next, N,N-dimethyl 3-phenyl-3-chloropropylamine hydrochloride is added. The resulting reaction mixture is refluxed for about 5 days and then cooled. The methanol was then removed by evaporation, and the resulting residue taken up in a mixture of ether and 5 N aqueous sodium hydroxide. The ether layer is separated and washed twice with 5 N aqueous sodium hydroxide and three times with water. The ether layer is dried, and the ether removed by evaporation in vacuo to yield as a residue N,N-dimethyl 3-(p-trifluoromethylphenoxy)-3-phenylpropylamine 5. A solution containing cyanogen bromide in benzene and toluene is placed in a three-neck round-bottom flask equipped with thermometer, addition funnel, drying tube and inlet tube for nitrogen. The solution is cooled and nitrogen gas is bubbled thru the solution. Next, a solution of N,N-dimethyl 3-(p-trifluoromethylphenoxy)-3-phenylpropylamine 5 dissolved in benzene is added in dropwise fashion. The temperature of the reaction mixture is allowed to rise slowly to room temperature, at which temperature stirring is continued overnight while still maintaining a nitrogen atmosphere. The reaction mixture is washed twice with water, once with 2 N aqueous sulfuric acid and then with water until neutral. The organic layer is dried, and the solvents removed therefrom by evaporation in vacuo to yield N-methyl-N-cyano 3-(p-trifluoromethylphenoxy)-3-phenylpropylamine 6. A solution of potassium hydroxide, water, ethylene glycol and of N-methyl-N-cyano 3-(p-trifluoromethylphenoxy)-3-phenylpropylamine is placed in a three-neck, round-bottom flask equipped with magnetic stirrer and condenser. The reaction mixture is heated to refluxing temperature for 20 hours, and is then cooled. The reaction mixture is extracted with ether. The ether extracts are combined, and the combined extracts washed with water. The water wash is discarded. The ether solution is next contacted with 2 N aqueous hydrochloric acid. The acidic aqueous layer is separated. A second aqueous acidic extract with 2 N hydrochloric acid is made followed by three aqueous extracts and an extract with saturated aqueous sodium chloride. The aqueous layers are all combined and made basic with 5 N aqueous sodium hydroxide. N-methyl 3-(p-trifluoromethylphenoxy)-3-phenylpropylamine 7, formed in the above reaction, is insoluble in the basic solution and separated. The amine is extracted into ether. The ether extracts are combined, and the combined extracts washed with saturated aqueous sodium chloride and then dried. Evaporation of the ether in vacuo yielded N-methyl 3-(p-trifluoromethylphenoxy)-3-phenylpropylamine 7. Finally, the compound 7 is then placed in DMF and activated with and O-(benzotriazol-1-yl)-N,N',N',N',-tetramethyluronium hexafluorophosphate (HBTU) and Diisopropylethylamine (DIEA). To the reaction mixture is added 3-maleimidopropionic acid. The reaction is stirred for 3 hours. The organic phase is then washed with water and brine, dried over $MgSO_4$, chromatographied, triturated with cold ether and left to crystallizeto produce 8 to produce the modified anti-depressant molecule

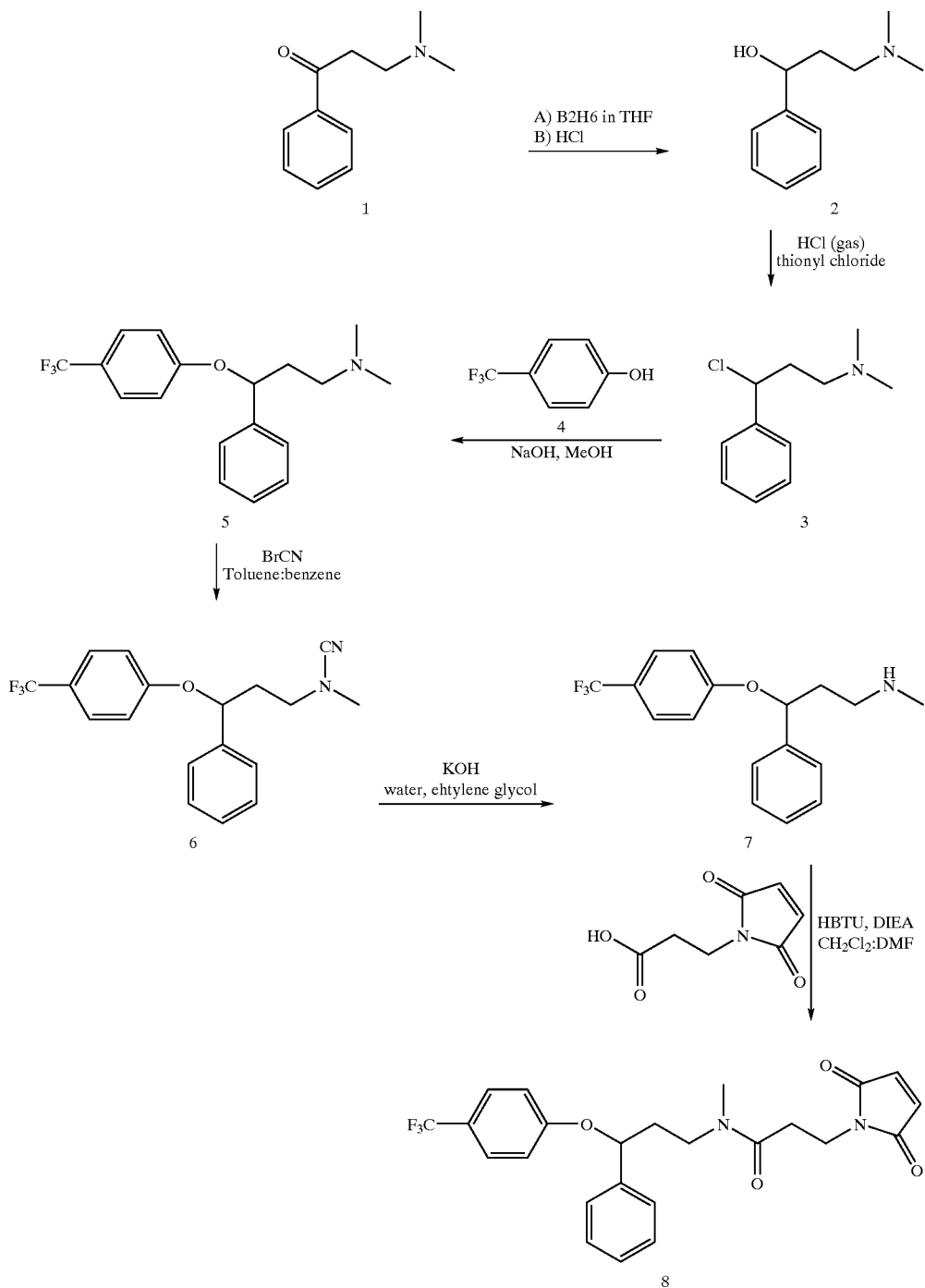

EXAMPLE 26

N-(2-maleimidoethyl-3,5-3',5' tetraiodothyronamide (Modified-Thyroxine)

N-t-Boc-3,5-3',5' tetraiodothyronine 1 is placed in DMF and activated with and O-(benzotriazol-1-yl)-N,N',N',N',-tetramethyluronium hexafluorophosphate (HBTU) and Diisopropylethylamine (DIEA) as indicated in the schematic below. To the reaction mixture is added 3-maleimidopropylamine. The reaction is stirred for 3 hours. The organic phase is then washed with water and brine, dried over $MgSO_4$, triturated with cold ether and left to crystallize to produce 2. Finally the compound is placed in a 25% solution of TFA in $CH_2Cl_2$ for 15 minutes and the $CH_2Cl_2$ is removed invacuo. The oily residue is then lyophilized to yield the desired compound 3, a modified thyroxine for treament of thyroid deficiency, i.e., an anti-thyroid deficiency agent.

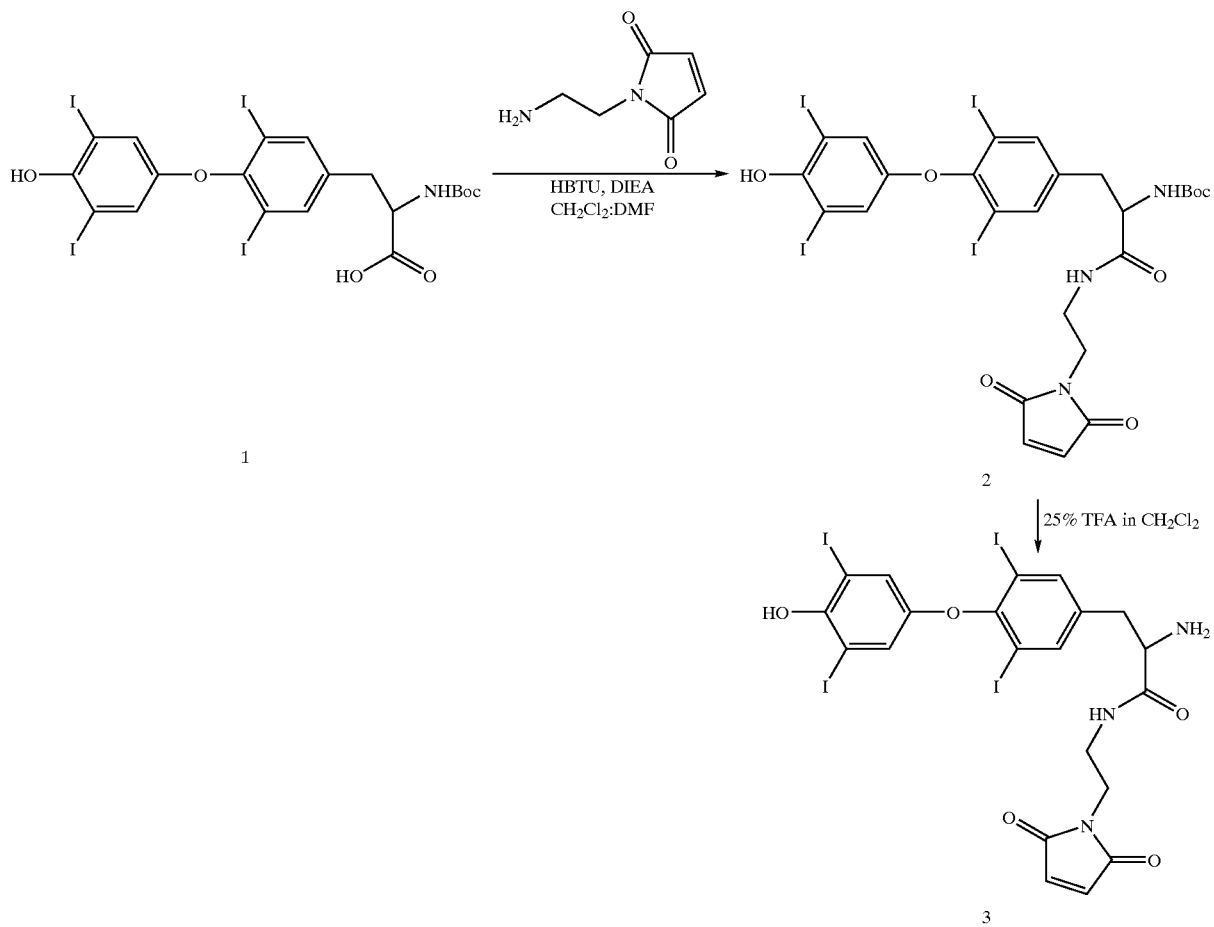

EXAMPLE 27

2S-hydroxy-3R-[1S-(MEEA-EDA-carbonyl)-2 2-dimethyl-propylcarbamoyl]-5-methylhexanohydroxamic acid (Modified MMPI)

The compound 1 and 3,4-dihydro-2H-pyran in $CH_2Cl_2$ and pyridinium p-toluenesulfonate are stirred at room temperature for 12 h as indicated in the schematic below. Then the solution is diluted with EtOAc and washed with half-saturated brine to remove the catalyst. The solvent is evaporated and the residue is treated with NaOH(1N) and EtOH for 30 min. The solution is acidified with AcOH, and the product is extracted with EtOAc. The EtOAc solution is dried, evaporated to give the THP ether 2. The compound 2, DCC and HOBT in $CH_2Cl_2$ are stirred at room temperature for 60 min. Then MEEA-EDA HCl (N-(2-aminoethyl)[2-(2-maleiimidoethoxy)ethoxy]acetamide) and N-methylmorpholine are added. The reaction is stirred for 2 h., and then quenched by addition of AcOH. The precipitate is removed by filtration. The filtrate is washed with diluted HCl, $NaHCO_3$, and dried. The crude product is used for the next step. The crude product is treated with 2N HCl $H_2O$/EtOH 1:1) for 30 min. EtOH is evaporated. The product is extracted with $CH_2Cl_2$. The combined $CH_2Cl_2$ layers are washed with $NaHCO_3$, and dried. Evaporation of the solvent gives a residue, which is purified by flash column chromatography to afford 3. This compound can be purified further by HPLC on a reverse phase column and lyophilized to produce the modified MMPI.

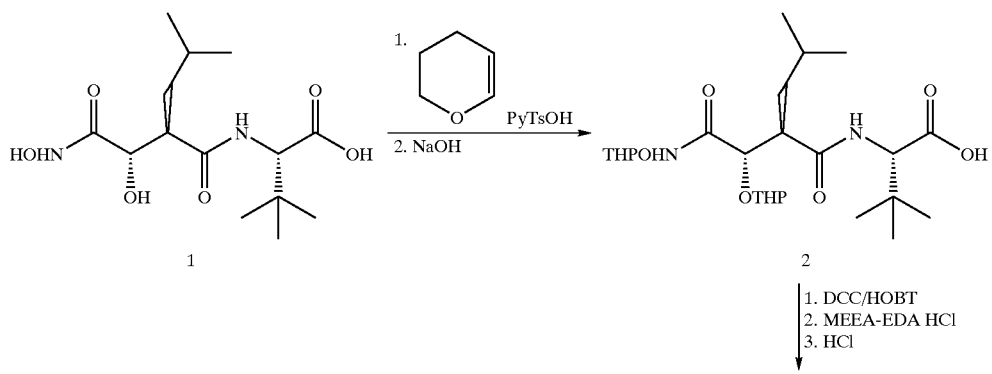

-continued

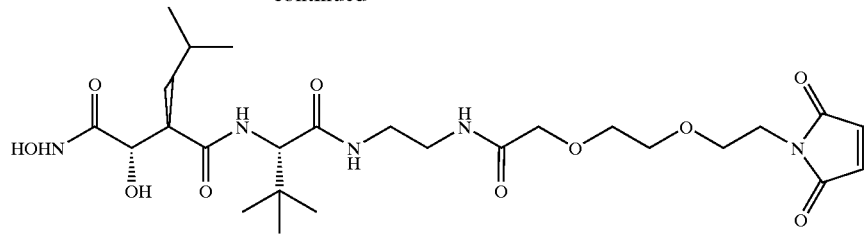

3

EXAMPLE 28

Preparation of Rhodamine NHS Ester

Rhodamine Green™-X, succinimidyl ester, hydrochloride mixed isomers is commercially available from Molecular Probes (Eugene Oreg.) as illustrated below:

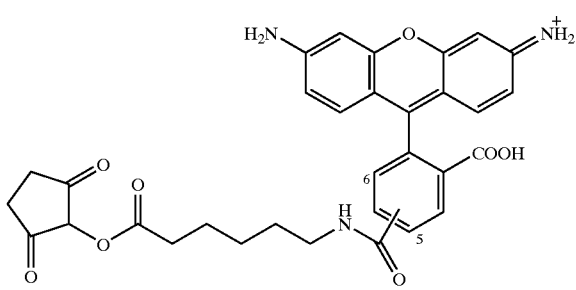

EXAMPLE 29

In vivo Addition of NHS-rhodamine

New Zealand rabbits (2 Kg), male or female, were intramuscularly anesthetized with Xylazine (20 mg/kg), Ketamine (50 mg/kg) and Acepromazine (0.75 mg/kg) prior to surgical exposure of left carotid artery. Both carotid arteries were isolated and blood flows were measured. A catheter (22G) was inserted in the arterial segment and rinsed with 0.9% sodium chloride via catheter until there was no more visible evidence of blood in the segment.

A 1-cm incubation chamber was created by ligatures in the segment area. The incubation chamber was flushed three times with 1 mL of 0.9% sodium chloride. A solution of 100 μl of 500 μM NHS-Rhodamine was prepared and incubated in the incubation chamber for 3 minutes. The excess of rhodamine was withdrawn with a 1 mL syringue. The incubation chamber was washed once again with 3 times 100 mL of 0.9% sodium chloride. The incubation chamber was then removed from the rabbit, cut in three pieces and dipped in 10% formalin for further evaluation. The NHS-Rhodamine treated arteries exhibited dramatic levels of fluorescence whereas those arteries treated solely with Rhodamine exhibited little fluorescence over background. These results demonstrate that Rhodamine was covalently bonded to a local delivery site.

EXAMPLE 30

Preparation of [$^3$H]-NHS-propionate

[$^3$H ]-NHS-propionate is available from Amersham Canada Ltd. (Oakville, Ontario, Canada) and can be prepared from the tritiated propionic acid through known to the art condensation of N-hydrosuccinimide in presence of EDC in DMF or methylene chloride.

EXAMPLE 31

In vivo Pharmacokinetics Studies of [$^3$H]-NHS-propionate

New Zealand rabbits (2 kg), male or female, were intramuscularly anesthetized with Xylazine (20 mg/kg), Ketamine (50 mg/kg) et Acepromazine (0.75 mg/kg) prior to surgical exposure of left carotid artery. Segments of 10 mm of carotids, were transiently isolated by temporary ligatures and rinsed with 0.9% sodium chloride via a cannula until there was no more visible evidence of blood components.

A catheter (18G) was inserted in the arterial segment and served to introduce the angioplasty balloon (2.5 mm of diameter, over the wire/Boston Scientific Inc.). A vascular damage (angioplasty) was performed on the isolated segment in order to eliminate the layer of endothelial cells. The angioplasty balloon was serially inflated at different atmospheres (4, 6, 8 and 10) during 1 minute, with 45 seconds of delay between inflations. At 4 atmospheres a balloon traction was performed 5 times and 1000 U/kg of heparin were infused in the blood circulation.

The angioplasty balloon was then retrieved from the artery and the catheter was reintroduced. The arterial segment was rinsed 3 times with saline, and 100 μM of [$^3$H]-NHS-propionate was incubated within the isolated segment of the artery for either 30 seconds, 3 minutes or 30 minutes. At the end, the excess of incubation liquid was withdrawn from the artery, and the segment was rinsed 5 times with saline. The treated artery was immediately harvested, and incorporation of [$^3$H]-labeled compounds within the artery was evaluated by scintillation counting. After 30 seconds of incubation, we recorded an association efficiency of 2.55%. At 3 min and 30 min, we recorded an association efficiency of 5.5 and 6.5%, respectively. We decided that a 3 min incubation time was sufficient to treat the artery in an efficient way.

When evaluating the retention levels, 100 μM of [$^3$H ]-NHS-propionate or [$^3$H ]-propionate were incubated with the artery for a period of 3 minutes, after which the segment has been rinsed 5 times with saline. The catheter was then removed and the arteriotomy site was closed with microsutures, thus reestablishing the blood flow within the carotid. Finally, the neck wound was closed with sutures, and animals are allowed to recuperate. Three days following the treatment, the animals are sacrificed with an overdose of sodium pentobarbital, the carotid segments are removed and examined for compound's presence by scintillation counting. 10.94% retention of [$^3$H]-NHS-propionate was monitored after three days following a 3 minute incubation period based on residual radioactivity in the artery. The difference in retention efficiency between covalently and non covalently bound propionate after a 3 minutes incubation period was determined. An outstanding 12 fold enhancement in retention was recorded (0.6% of total amount incubated against 0.046% for the non covalently bound) in favor of the NHS-propionate. This indicates that the tissue association of a compound is dramatically enhanced by the covalent attachment in vivo. Subsequent restitution of blood flow demonstrated retention [$^3$H]-NHS-propionate of approximately 10% of the material 72 hours after injury. This represents excessive tissue retention using the embodied technology of agents markedly beyond that seen with all drug delivery technologies as exemplified in the literature for standard non covalent agents (*Circulation* 1994 89 (4) 1518–1524).

EXAMPLE 32

Synthesis of [$^{32}$P]NHS Derivative

To a solution of protected R and R' (both R and R' can be alkyl, phenyl or alkoxy groups, and X is either O or S, alkoxy, alkyl and any other functionality stable under these conditions) phosphodiester (0.1 mmol) and N-hydroxysuccinimide (0.2 mmol) is added diisopropylethylamine 0.11 mmol), followed by addition of HBTU (0.22 mmol). The reaction mixture is stirred at room temperature for 36 hours. DMF is removed by vacuum distillation and the residue is dissolved in MeOH (10 mL). The MeOH solution is filtered to remove the insolubles, the filtrate is concentrated in vacuo, and the residue is dissolved in a minimum amount of MeOH. Water is then added to induce precipitation and the precipitate is dried on vacuum to give the desired compound.

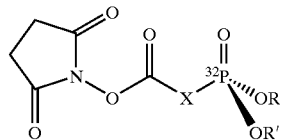

The yield of the reaction can usually be improved by using EDC as the coupling reagent, as exemplified below. To a solution of R and R' phosphodiester (0.054 mmol) and N-hydroxysuccinimide (0.115 mmol) in anhydrous DMF (3 mL), is added EDC (31 mg, 0.162 mmol). The solution is stirred at room temperature for 24 hours. DMF is removed by vacuum distillation and the residue is further dried on high vacuum. The residue is then dissolved in a minimum amount of MeOH (0.12 mL) and H$_2$O (3.2 mL) is added to induce precipitation. The precipitates are washed with H$_2$O (3×0.8 mL) and dried on vacuum to give a solid product.

Any protected phosphonate derivatives may undergo similar transformation.

EXAMPLE 33

New Zealand rabbits (2 kg), male or female, were anesthetized with xylazine (20 mg/kg), ketamine (50 mg/kg) and acepromazine (0.75 mg/kg) intramuscularly prior to surgical exposure of left carotid artery. Carotid arteries were surgically dissected and segments of approximately 10 mm length were isolated. The vessels were cannulated and rinsed with 0.9% sodium chloride until there was no more visible evidence of blood components.

A catheter (18G) was inserted in the arterial segment and served to introduce the angioplasty balloon (2.5 mm of diameter, over the wire/Boston Scientific Inc.). Vascular damage (angioplasty) was performed on the isolated segment in order to eliminate the layer of endothelial cells. The angioplasty balloon was serially inflated at different atmospheres (4, 6, 8 and 10) for 1 minute, with 45 seconds of delay between inflations. At 4 atmospheres a balloon traction was performed 5 times and 1000 U/kg of heparin were infused in the blood circulation.

The angioplasty balloon was then retrieved from the artery and the catheter was reintroduced. The arterial segment was rinsed 3 times with saline, and 100 μM of [$^{32}$P]-NHS-[linking group] was incubated within the isolated segment of the artery for 3 minutes. At the end, the excess of incubation liquid was withdrawn from the artery, and the segment was rinsed 5 times with saline. The vessel was sutured closed, blood flow restored and surgical wounds repaired. Animals were returned to the vivarium for periods up to four weeks. Tissue retention of [$^{32}$P]-NHS-[linking group] was evaluating using whole animal radiography at selected periods of time after injury.

EXAMPLE 34

Synthesis of [$^{131}$I]-NHS Derivative

To a solution of protected amino protected [$^{131}$I]-iodotyrosine (0.1 mmol) and N-hydroxysuccinimide (0.2 mmol) is added diisopropylethylamine (0.11 mmol), followed by addition of HBTU (0.22 mmol). The reaction mixture is stirred at room temperature for 12 hours. DMF is removed by vacuum distillation and the residue is dissolved in MeOH (10 mL). The MeOH solution is filtered to remove the insolubles, the filtrate is concentrated in vacuo, and the residue is dissolved in a minimum amount of MeOH. Water is then added to induce precipitation and the precipitate is dried on vacuum to give the desired compound.

The yield of the reaction can usually be improved by using EDC as the coupling reagent, as exemplified below. To a solution of [$^{131}$I]-iodotyrosine (0.054 mmol) and N-hydroxysuccinimide (0.115 mmol) in anhydrous DMF (3 mL), is added EDC (31 mg, 0.162 mmol). The solution is stirred at room temperature for 24 hours. DMF is removed by vacuum distillation and the residue is further dried on high vacuum. The residue is then dissolved in a minimum amount of MeOH (0.12 mL) and water (3.2 mL) is added to induce precipitation. The precipitates are washed with H$_2$O (3×0.8 mL) and dried on vacuum to give a solid product.

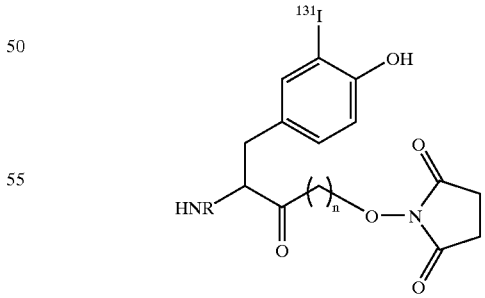

EXAMPLE 35

In vivo Pharmacology of $^{131}$I Derivative

New Zealand rabbits (2 Kg), male or female, were anesthetized with xylazine (20 mg/kg), ketamine (50 mg/kg) and acepromazine (0.75 mg/kg) intramuscularly prior to surgical exposure of left carotid artery. Carotid arteries were surgically dissected and segments of approximately 10 mm length were isolated. The vessels were cannulated and rinsed with 0.9% sodium chloride until there was no more visible evidence of blood components.

A catheter (18G) was inserted in the arterial segment and served to introduce the angioplasty balloon (2.5 mm of diameter, over the wire/Boston Scientific Inc.). Vascular damage (angioplasty) was performed on the isolated segment in order to eliminate the layer of endothelial cells. The angioplasty balloon was serially inflated at different atmospheres (4, 6, 8 and 10) for 1 minute, with 45 seconds of delay between inflations. At 4 atmospheres a balloon traction was performed 5 times and 1000 U/kg of heparin were infused in the blood circulation.

The angioplasty balloon was then retrieved from the artery and the catheter was reintroduced. The arterial segment was rinsed 3 times with saline, and 100 $\mu$M of [$^{131}$-]-NHS-[linking group] was incubated within the isolated segment of the artery for 3 minutes. At the end, the excess of incubation liquid was withdrawn from the artery, and the segment was rinsed 5 times with saline. The vessel was sutured closed, blood flow restored and surgical wounds repaired. Animals were returned to the vivarium for periods up to four weeks. Tissue retention of [$^{131}$I]-NHS-[linking group] was evaluated using whole animal radiography at selected periods of time after injury

EXAMPLE 36

2-[2-[4-[(4-chlorophenyl)phenylmethyl[-1-piperazinyl]ethoxy]-maleimido-ethylacetamide (Modified-Cetirizine)

A Bird Micronebulizer in line with a Bird Mark 7 respirator may be charged with 5–10 ml of a solution of 12 mg/ml 2-[2-[4-[(4-chloropheny)phenylmethyl[-1-piperazinyl] ethoxy]-maleimidopropionylacetamide in mannitol/ phosphate buffer. The Micronebulizer may then bes used to simultaneously ventilate and dose a patient at 22 cm H$_2$O at a rate of 1.8 mg/min for 30 min. At this pressure the patient shouldl ventilate at approximately normal inspiratory volume. The patient should be allowed to exhale normally after each ventilated breath. In addition, the patient should be positioned supine for dosing. After the first dosing period the patient should be allowed to breathe normally for another 20 minutes. After the 20 minute period, a second dosing should be performed in the same way as the first. Blood plasma samples should be taken at the initiation time of the first dose and thereafter to monitor the levels of 2-[2-[4-[(4-chlorophenyl)phenylmethyl[-1-piperazinyl]ethoxy]-maleimido-ethylacetamide.

EXAMPLE 37

Intrapulmonary Delivery of 2-[2-[4-[(4-chloropheny)phenylmethyl[-1-piperazinyl]ethoxy]-maleimidopropionylacetamide (Modified-Cetirizine) Using the Spiros DPI System The Spiros DPI is an aerosol generation system that is largely independent of the inspiratory flow rate and its use is described in U.S. Pat. No. 6,060,069.

A modified beclomethasone dipropionate (BDP) formulation may be prepared by first micronizing through conventional means (e.g., a jet mill) to produce a range of particle sizes that are likely to undergo sedimentation in the human airway. Generally, fine particles in the range of 0.5 to 5.8 microns in diameter are thought to undergo sedimentation between the oropharynx and small bronchioles. Particles within this general size category are thought to be in the "respirable range." Such micronized materials have excessive surface free energy, and as a result have a tendency to adhere strongly to many surfaces, most especially to themselves.

Lactose particles in the size range of 20 to 100 microns may be mixed with the smaller diameter micronized drug particles to create a homogenous blend. Each lactose particle will generally bind to a number of smaller drug particles in the blend. The blend flows more easily during the packaging and dose metering process.

The formulation may be then filled into cassettes, each containing 30 individual doses. The cassettes may then packaged in sealed foil pouches.

The following steps using the Spiros BPI system may be used to deliver a dose of inhaled drug: 1. The Spiros DPI does not need to be primed; 2. The blue plastic cap is removed from the mouthpiece; 3. The inhaler is held level; 4. The lid of the DPI is opened as far back as possible (The lid will click when it has reached the correct angle); 5. The lid is then closed completely; 6. Before bringing the inhaler up to the mouth, the patient breathes out, making sure not to breathe into the inhaler.; 7. The inhaler is brought up to the mouth in a level position; 8. The lips are sealed fully around the mouthpiece, making sure there is no gap between the mouthpiece and the lips; 9. The patient breathes in through the mouth for about 4 seconds, preferably at a flow rate of about 20 LPM. The motor will turn on and the patient may taste/feel the drug as it is inhaled; 10. The patient holds their breath for as long as possible, up to 10 seconds. 11. The Spiros DPI is held in a level position during loading and dosing.

---

We claim:

1. A pharmaceutical composition comprising a compound selected from the group consisting of:

a) 2-[2-[4-[(4-chlorophenyl)phenylmethyl[-1-piperazinyl]ethoxy]-maleimido-ethylacetamide;
b) 11-(N-maleimidopropionyl-4-piperidylidene)-8-chloro-6,11-dihydro-5H-benzo-[5,6]-cyclohepta-[1,2-b]-pyridine;
c) N-(2-maleimidoethyl)-(1(S)-Ethoxycarbonyl-3-phenylpropyl)-L-alanyl-L-prolinylamide;
d) N-[2-maleimidoethyl-ε-(3,4,5-trimethoxybenzamido)-caproic amide;
e) Maleimidoethyl-1-theobromineacetamide;
f) N-(2-maleimidoethyl)-2-[4-(2-oxocyclopentan-1-ylmethyl)phenyl]-propionamide;
g) N-maleimidopropionyl-N-methyl-3-(p-trifluoromethylphenoxy)-3-phenylpropylamine;
h) 4-[N-phenyl-3-maleimidopropionamido]-1-(2-phenylethyl)piperidine; and
i) N-(2-maleimidoethyl-3,5-3',5' tetraiodothyroninamide.

2. The composition of claim 1, wherein the compound is N-(2-maleimidoethyl)-3,5-3',5' tetraiodothyroninamide.

3. A compound selected from the group consisting of:

a) 2-[2-[4-[(4-chlorophenyl)phenylmethyl[-1-piperazinyl]ethoxy]-maleimido-ethylacetamide;
b) 11-(N-maleimidopropionyl-4-piperidylidene)-8-chloro-6,11-dihydro-5H-benzo-[5,6]-cyclohepta-[1,2-b]-pyridine;
c) N-(2-maleimidoethyl)-(1(S)-Ethoxycarbonyl-3-phenylpropyl)-L-alanyl-L-prolinylamide;
d) N-[2-maleimidoethyl-ε-(3,4,5-trimethoxybenzamido)-caproic amide;
e) Maleimidoethyl-1-theobromineacetamide;
f) N-(2-maleimidoethyl)-2-[4-(2-oxocyclopentan-1-ylmethyl)phenyl]-propionamide;
g) N-maleimidopropionyl-N-methyl-3-(p-trifluoromethylphenoxy)-3-phenyl-propylamine;
h) 4-[N-phenyl-3-maleimidopropionamido]-1-(2-phenylethyl)piperidine; and
i) N-(2-maleimidoethyl)-3,5-3',5' tetraiodothyroninamide.

4. An aerosol composition for delivery of a compound as claimed in claim 1 to the pulmonary system of a host comprising an aerosolized aqueous solution containing the compound which reacts with thiol groups on pulmonary or blood components to form a stable covalent bond.

5. The aerosol composition as claimed in claim 3 further comprising a pharmaceutically acceptable carrier.

6. A particulate formulation for delivery of a compound as claimed in claim 3 to the pulmonary system of a host comprising a dispersable dry powder containing the compound which reacts with thiol groups on pulmonary components to form a stable covalent bond.

7. A composition as claimed in claim 4 wherein the blood component is serum albumin.

8. A composition for treating excess histamine formed in body tissues, comprising a compound as claimed in claim 3 which is selected from the group consisting of 2-[2-[4-[(4-chlorophenyl)phenylmethyl[-1-piperazinyl]ethoxy]-maleimido-ethylacetamide and 11-(N-maleimidopropionyl-4-piperidylidene)-8-chloro-6,11-dihydro-5H-benzo-[5,6]-cyclohepta-[1,2-b]-pyridine, or mixtures thereof.

9. A composition for treating hypertension comprising a compound as claimed in claim 3 which is N-(2-maleimidoethyl)-(1(S)-ethoxycarbonyl-3-phenylpropyl)-L-alanyl-L-prolinylamide.

10. A composition for treating arrhythmia comprising a compound as claimed in claim 3 which is N-[2-maleimidoethyl-ϵ-(3,4,5-trimethoxybenzamido)-caproic amide.

11. A bronchodilating composition comprising a compound as claimed in claim 3 which is maleimidoethyl-1-theobromineacetamide.

12. A composition for treating inflammation comprising a compound as claimed in claim 3 which is N-(2-maleimidoethyl)-2-[4-(2-oxocyclopentan-1-ylmethyl) phenyl]-propionamide.

13. A composition for treating depression comprising a compound as claimed in claim 3 which is N-maleimidopropionyl-N-methyl-3-(p-trifluoromethylphenoxy)-3-phenyl-propylamine.

14. A composition for alleviating pain comprising a compound as claimed in claim 3 which is 4-[N-phenyl-3-maleimidopropionamido]-1-(2-phenylethyl)piperidine.

15. A composition for treating anemia comprising a compound as claimed in claim 3 which is N-(2-maleimidoethyl)-3,5-3',5' tetraiodothyroninamide.

16. A method for treating excess histamine formed in body tissues, comprising administering to a patient an effective amount of a compound as claimed in claim 3 which is selected from the group consisting of 2-[2-[4-[(4-chlorophenyl)phenylmethyl[-1-piperazinyl]ethoxy]-maleimido-ethylacetamide and 11-(N-maleimidopropionyl-4-piperidylidene)-8-chloro-6,11-dihydro-5H-benzo-[5,6]-cyclohepta-[1,2-b]-pyridine, or mixtures thereof.

17. A method for treating hypertension comprising administering to a patient an effective amount of a compound as claimed in claim 3 which is N-(2-maleimidoethyl)-(1(S)-Ethoxycarbonyl-3-phenylpropyl)-L-alanyl-L-prolinylamide.

18. A method for treating arrhythmia comprising administering to a patient an effective amount of a compound as claimed in claim 3 which is N-[2-maleimidoethyl-ε-(3,4,5-trimethoxybenzamido)-caproic amide.

19. A method for providing a bronchodilation effect comprising administering to a patient an effective amount of a compound as claimed in claim 3 which is maleimidoethyl-1-theobromineacetamide.

20. A method for treating inflammation comprising administering to a patient an effective amount of a compound as claimed in claim 3 which is N-(2-maleimidoethyl)-2-[4-(2-oxocyclopentan-1-ylmethyl)phenyl]-propionamide.

21. A method for treating depression comprising administering to a patient an effective amount of a compound as claimed in claim 3 which is N-maleimidopropionyl-N-methyl-3-(p-trifluoromethylphenoxy)-3-phenyl-propylamine.

22. A method for alleviating pain comprising administering to a patient an effective amount of a compound as claimed in claim 3 which is 4-[N-phenyl-3-maleimidopropionamido]-1-(2-phenylethyl)piperidine.

23. A method for treating anemia comprising administering to a patient an effective amount of a compound as claimed in claim 3 which is N-(2-maleimidoethyl)-3,5-3',5' tetraiodothyroninamide.

24. A conjugate comprising a compound as claimed in claim 3 covalently bonded to a pulmonary or blood component.

25. A conjugate as claimed in claim 24 wherein the blood component is serum albumin.

26. The compound of claim 3, wherein the compound is 2-[2-[4-[(4-chlorophenyl)phenylmethyl[-1-piperazinyl]ethoxy]-maleimido-ethylacetamide.

27. The compound of claim 3, wherein the compound is 11-(N-maleimidopropionyl-4-piperidylidene)-8-chloro-6,11-dihydro-5H-benzo-[5,6]-cyclohepta-[1,2-b]-pyridine.

28. The compound of claim 3, wherein the compound is N-(2-maleimidoethyl)-(1(S)-Ethoxycarbonyl-3-phenylpropyl)-L-alanyl-L-prolinylamide.

29. The compound of claim 3, wherein the compound is N-[2-maleimidoethyl-ε-(3,4,5-trimethoxybenzamido)-caproic amide.

30. The compound of claim 3, wherein the compound is maleimidoethyl-1-theobromineacetamide.

31. The compound of claim 3, wherein the compound is N-(2-maleimidoethyl)-2-[4-(2-oxocyclopentan-1-ylmethyl)phenyl]-propionamide.

32. The compound of claim 3, wherein the compound is N-maleimidopropionyl-N-methyl-3-(p-trifluoromethylphenoxy)-3-phenyl-propylmine.

33. The compound of claim 3, wherein the compound is 4-[N-phenyl-3-maleimidopropionamido]-1-(2-phenylethyl)piperidine.

34. The compound of claim 3, wherein the compound is N-(2-maleimidoethyl)-3,5-3,5' tetraiodothyroninamide.

* * * * *

SEQUENCE LISTING

```
<160> NUMBER OF SEQ ID NOS:  16

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 1
```

```
Ala Gly Tyr Lys Pro Glu Gly Lys Arg Gly Asp Ala Lys
  1               5                  10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 2

Lys Arg Gly Asp Ala Cys Glu Gly Asp Ser Gly Gly Pro Phe Cys
  1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 3

Lys Arg Gly Asp Ala Cys Glu Gly Asp Ser Gly Gly Pro Phe Cys
  1               5                  10                  15

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 4

Tyr Thr Ser Leu Ile His Ser Leu Ile Glu Glu Ser Gln Asn Gln Gln
  1               5                  10                  15

Glu Lys Asn Glu Gln Glu Leu Leu Glu Leu Asp Lys Trp Ala Ser Leu
             20                  25                  30

Trp Asn Trp Phe
         35

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 5

Tyr Thr Ser Leu Ile His Ser Leu Ile Glu Glu Ser Gln Asn Gln Gln
  1               5                  10                  15

Glu Lys Asn Glu Gln Glu Leu Leu Glu Leu Asp Lys Trp Ala Ser Leu
             20                  25                  30

Trp Asn Trp Phe
         35

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence:Synthetic
```

Peptide

<400> SEQUENCE: 6

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 7

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

Glu Asn Val Lys
        35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 8

Lys Val Tyr Pro Ser Asp Glu Tyr Asp Ala Ser Ile Ser Gln Val Asn
 1               5                  10                  15

Glu Glu Ile Asn Gln Ala Leu Ala Tyr Ile Arg Lys Ala Asp Glu Leu
            20                  25                  30

Leu Glu Asn Val
        35

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 9

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

Glu Asn Val
        35

<210> SEQ ID NO 10
<211> LENGTH: 31
<212> TYPE: PRT
<213> ORGANISM: Artificial Sequence
<220> FEATURE:

```
<223> OTHER INFORMATION: Description of Artificial Sequence:Synthetic
      Peptide

<400> SEQUENCE: 10

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys
             20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 11

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 12

Pro Arg Lys Leu Tyr Asp Tyr Lys
  1               5

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 13

Arg Asn Pro Asp Gly Asp Val Gly Gly Pro Trp Ala Trp Thr Thr Ala
  1               5                  10                  15

Pro Arg Lys Leu Tyr Asp Tyr
             20

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 14

Tyr Gly Arg Lys Lys Arg Arg Gln Arg Arg Lys
  1               5                  10

<210> SEQ ID NO 15
<211> LENGTH: 12
<212> TYPE: PRT
<213> ORGANISM: Artificial Sequence
<220> FEATURE:
```

-continued

```
<223> OTHER INFORMATION: Description of Artificial Sequence:Synthetic
      Peptide

<400> SEQUENCE: 15

Tyr Gly Arg Lys Lys Arg Arg Gln Arg Arg Lys
 1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 16

Tyr Gly Gly Phe Leu Arg Arg Ile Arg Pro Lys Leu Lys
 1               5                   10
```